(12) United States Patent
Swantner et al.

(10) Patent No.: US 11,291,766 B2
(45) Date of Patent: Apr. 5, 2022

(54) SYSTEM AND METHOD FOR FLUID ENGAGEMENT WITH A PRESSURE JACKET AND SYRINGE CAP

(71) Applicant: BAYER HEALTHCARE LLC, Whippany, NJ (US)

(72) Inventors: Michael J. Swantner, Saxonburg, PA (US); Richard A. Seman, Delmont, PA (US); Barry L. Tucker, Verona, PA (US); Arthur E. Uber, III, Pittsburgh, PA (US); Kevin P. Cowan, Allison Park, PA (US); James A. Dedig, Pittsburgh, PA (US); Christopher D. Capone, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 722 days.

(21) Appl. No.: 15/769,550

(22) PCT Filed: Oct. 28, 2016

(86) PCT No.: PCT/US2016/059245
§ 371 (c)(1),
(2) Date: Apr. 19, 2018

(87) PCT Pub. No.: WO2017/075302
PCT Pub. Date: May 4, 2017

(65) Prior Publication Data
US 2018/0304007 A1 Oct. 25, 2018

Related U.S. Application Data

(60) Provisional application No. 62/247,534, filed on Oct. 28, 2015.

(51) Int. Cl.
*A61M 5/145* (2006.01)
*A61M 5/315* (2006.01)

(52) U.S. Cl.
CPC .... *A61M 5/14546* (2013.01); *A61M 5/14566* (2013.01); *A61M 5/31515* (2013.01);
(Continued)

(58) Field of Classification Search
CPC ............ A61M 5/14546; A61M 5/4566; A61M 5/31515; A61M 2005/14553;
(Continued)

(56) References Cited

U.S. PATENT DOCUMENTS

| 5,383,858 A | 1/1995 | Reilly et al. |
| 5,947,935 A | 9/1999 | Kazousky et al. |

(Continued)

FOREIGN PATENT DOCUMENTS

| EP | 2223713 A2 | 9/2010 |
| EP | 2412395 A1 | 2/2012 |

(Continued)

OTHER PUBLICATIONS

"Extended European Search Report from EP Application No. 16860849", dated Apr. 15, 2019.
(Continued)

*Primary Examiner* — Bhisma Mehta
*Assistant Examiner* — Larry R. Wilson
(74) *Attorney, Agent, or Firm* — Joseph L. Kent; David Schramm; James R. Stevenson

(57) ABSTRACT

A pressure jacket for use with a fluid injector may have a pressure jacket body having a proximal end, a distal end, and a circumferential sidewall extending between the proximal end and the distal end along a pressure jacket longitudinal axis. The pressure jacket may further have at least one resiliently deflectable retaining member having a first segment attached to the pressure jacket body and a second segment protruding from the first segment toward the distal end of the pressure jacket body and deflectable relative to the
(Continued)

first segment. The pressure jacket may further have at least one actuation member associated with the at least one resiliently deflectable retaining member. The at least one actuation member may interact with a housing of the fluid injector when the pressure jacket is connected to the housing to deflect the at least one resiliently deflectable retaining member upon rotation of the pressure jacket.

10 Claims, 57 Drawing Sheets

(52) U.S. Cl.
CPC ............ *A61M 2005/14553* (2013.01); *A61M 2005/14573* (2013.01); *A61M 2205/332* (2013.01)

(58) Field of Classification Search
CPC .. A61M 2005/14573; A61M 2205/332; A61M 5/007; A61M 5/1456; A61M 5/14566; A61M 39/10; A61M 2039/1027; A61M 2039/1033; A61M 5/31576; A61M 5/31578; A61M 5/31511
See application file for complete search history.

(56) References Cited

U.S. PATENT DOCUMENTS

| | | | |
|---|---|---|---|
| 6,322,535 B1 | 11/2001 | Hitchins et al. | |
| 6,652,489 B2 | 11/2003 | Trocki et al. | |
| 7,553,294 B2 | 6/2009 | Lazzaro et al. | |
| 7,666,169 B2 | 2/2010 | Cowan et al. | |
| 9,173,995 B1 | 11/2015 | Tucker et al. | |
| 9,199,033 B1 | 12/2015 | Cowan et al. | |
| 2002/0177811 A1* | 11/2002 | Reilly | A61M 5/14546 604/152 |
| 2004/0064041 A1* | 4/2004 | Lazzaro | A61M 5/14546 600/432 |
| 2006/0100581 A1 | 5/2006 | Mogensen | |
| 2013/0018357 A1* | 1/2013 | Adair | A61M 5/14244 604/506 |
| 2014/0027009 A1 | 1/2014 | Riley et al. | |

FOREIGN PATENT DOCUMENTS

| | | | | |
|---|---|---|---|---|
| JP | 2002528234 A | 9/2002 | | |
| WO | 0025852 A1 | 5/2000 | | |
| WO | 2009039050 A1 | 3/2009 | | |
| WO | WO-2009038955 A1 * | 3/2009 | ........ | A61M 5/14546 |
| WO | 2012155035 A1 | 11/2012 | | |
| WO | 2017075303 A1 | 5/2017 | | |

OTHER PUBLICATIONS

"International Search Report from PCT/US16/59245", dated Mar. 10, 2017.

* cited by examiner

SYSTEM AND METHOD FOR FLUID ENGAGEMENT WITH A PRESSURE JACKET AND SYRINGE CAP

CROSS-REFERENCE TO RELATED APPLICATIONS

The present application is a 371 national phase application of PCT International Application No. PCT/US2016/059245, filed Oct. 28, 2016, which claims priority to U.S. Provisional Patent Application No. 62/247,534, filed on Oct. 28, 2015 and entitled "System and Method for Fluid Injector Engagement with a Pressure Jacket and Syringe Cap", the disclosure of which is incorporated herein in its entirety.

BACKGROUND OF THE DISCLOSURE

Field of the Disclosure

The present disclosure relates generally to a system including a front-loading syringe for use with a fluid injector and, further, to a connection interface for securing a syringe plunger to a piston of the fluid injector and to a method for engaging and disengaging the syringe plunger to and from the piston of the fluid injector. The present disclosure also relates to a connection interface for securing a pressure jacket to a fluid injector housing, as well as a connection interface for securing a syringe cap to a pressure jacket.

Description of Related Art

In many medical diagnostic and therapeutic procedures, a medical practitioner, such as a physician, injects a patient with one or more medical fluids. In recent years, a number of injector-actuated syringes and fluid injectors for pressurized injection of fluids, such as a contrast solution (often referred to simply as "contrast"), a flushing agent, such as saline, and other medical fluids have been developed for use in procedures such as angiography, computed tomography (CT), ultrasound, magnetic resonance imaging (MRI), positron emission tomography (PET), and other imaging procedures. In general, these fluid injectors are designed to deliver a preset amount of fluid at a preset flow rate.

Various connection interfaces have been developed to facilitate the engagement of a syringe plunger to and from a piston of the fluid injector. In some aspects, the syringe having a retention feature is inserted into a syringe port on the fluid injector by aligning the syringe with a corresponding locking feature provided on the fluid injector. Such alignment also aligns the plunger in the syringe with the piston on the fluid injector such that the piston can engage the plunger and reciprocally drive the plunger through the syringe barrel to withdraw fluid into the syringe barrel or deliver fluid from the syringe barrel. In other aspects, upon initial engagement with the plunger, the piston is rotated, in a clockwise or counterclockwise direction, until the piston engages a catch on the plunger. In further aspects, the piston has one or more radially-extendable pins that engage a lip on the plunger.

Many of the existing connection interfaces have construction that requires a complex piston head with various sensor elements and active engagement structures. There is a need in the art for an improved connection interface that allows for a simpler and easier engagement and disengagement of the syringe plunger to and from the piston of the fluid injector. There is a further need in the art for reducing or eliminating the need for the operator to rotationally align the syringe with the fluid injector prior to engagement of the syringe plunger with the piston of the fluid injector. There is further a need in the art for an improved connection interface that allows for a simpler and easier engagement and disengagement of the pressure jacket with the fluid injector, and the pressure jacket to a syringe cap. While various syringe connection interfaces and methods are known in the medical field, improved connection interfaces between the syringe plunger and the piston of the fluid injector and methods for engaging and disengaging the syringe plunger to and from the piston of the fluid injector continue to be in demand.

SUMMARY OF DISCLOSURE

In view of the disadvantages of the existing connection interfaces between a syringe plunger and a piston of a fluid injector, there is a need in the art for an improved connection interface between a syringe plunger and a piston of a fluid injector that overcomes the deficiencies of the prior art. There is an additional need for improved methods for engaging and disengaging a syringe plunger to and from a piston of a fluid injector to allow easy loading or removal of a syringe to and from a fluid injector. There is an additional need an improved connection interface between a pressure jacket and a fluid injector, and an improved connection interface between a pressure jacket and a syringe cap, that overcomes the deficiencies of the prior art.

In accordance with some aspects, a pressure jacket for use with a fluid injector and syringe may have a pressure jacket body having a proximal end, a distal end, and a circumferential sidewall extending between the proximal end and the distal end along a pressure jacket longitudinal axis. The pressure jacket may further have at least one resiliently deflectable retaining member having a first segment attached to the pressure jacket body and a second segment protruding from the first segment toward the distal end of the pressure jacket body and deflectable relative to the first segment. The pressure jacket may further have at least one actuation member associated with the at least one resiliently deflectable retaining member. The at least one actuation member may interact with a housing of the fluid injector when the pressure jacket is connected to the housing to deflect the at least one resiliently deflectable retaining member upon rotation of the pressure jacket relative to the housing during disengagement of the pressure jacket from the housing.

In accordance with other aspects, the pressure jacket may further have at least one alignment member associated with the pressure jacket body or the at least one resiliently deflectable retaining member. The at least one alignment member may have an alignment surface for guiding the housing into self-orienting alignment with the pressure jacket during engagement of the pressure jacket with the housing.

In accordance with other aspects, the at least one alignment member may have a plurality of alignment members spaced apart around the pressure jacket longitudinal axis.

In accordance with other aspects, the plurality of alignment members may be spaced apart at equal radial intervals around the pressure jacket longitudinal axis.

In accordance with other aspects, the second segment of the at least one resiliently deflectable retaining member may be deflectable radially relative to the first segment away from the pressure jacket longitudinal axis.

In accordance with other aspects, the at least one resiliently deflectable retaining member may be linearly or curvilinearly contiguous between the first segment and the second segment.

In accordance with other aspects, the second segment of the at least one resiliently deflectable retaining member may be angled toward the pressure jacket longitudinal axis.

In accordance with other aspects, the at least one actuation member may be provided on a surface of the at least one resiliently deflectable retaining member.

In accordance with other aspects, the at least one actuation member may be at the second segment of the at least one resiliently deflectable retaining member.

In accordance with other aspects, a syringe cap for use with a pressure jacket may have a syringe cap body having a proximal end, a distal end, and a circumferential sidewall extending between the proximal end and the distal end along a syringe cap longitudinal axis. The syringe cap may further have at least one resiliently deflectable retaining member having a first segment attached to the syringe cap body and a second segment protruding from the first segment toward the distal end of the syringe cap body and deflectable relative to the first segment. The syringe cap may further have at least one actuation member associated with the at least one resiliently deflectable retaining member. The at least one actuation member may interact with the pressure jacket when the syringe cap is connected to the pressure jacket to deflect the at least one resiliently deflectable retaining member upon rotation of the syringe cap relative to the pressure jacket during disengagement of the syringe cap from the pressure jacket.

In accordance with other aspects, the syringe cap may further have at least one alignment member associated with the syringe cap body or the at least one resiliently deflectable retaining member. The at least one alignment member may have an alignment surface for guiding the pressure jacket into self-orienting alignment with the syringe cap during engagement of the syringe cap with the pressure jacket.

In accordance with other aspects, the at least one alignment member may have a plurality of alignment members spaced apart around the syringe cap longitudinal axis.

In accordance with other aspects, the plurality of alignment members may be spaced apart at equal radial intervals around the syringe cap longitudinal axis.

In accordance with other aspects, the second segment of the at least one resiliently deflectable retaining member may be deflectable radially relative to the first segment away from the syringe cap longitudinal axis.

In accordance with other aspects, the at least one resiliently deflectable retaining member may be linearly or curvilinearly contiguous between the first segment and the second segment.

In accordance with other aspects, the second segment of the at least one resiliently deflectable retaining member may be angled toward the syringe cap longitudinal axis.

In accordance with other aspects, the at least one actuation member may be provided on a surface of the at least one resiliently deflectable retaining member.

In accordance with other aspects a pressure jacket and syringe cap assembly may have a pressure jacket having a pressure jacket body having a proximal end, a distal end, and a circumferential sidewall extending between the proximal end and the distal end along a pressure jacket longitudinal axis. The pressure jacket and syringe cap assembly may further have a syringe cap having a syringe cap body having a proximal end, a distal end, and a circumferential sidewall extending between the proximal end and the distal end along a syringe cap longitudinal axis. The pressure jacket and syringe cap assembly may further have at least one connector assembly for releasably attaching the proximal end of the syringe cap to the distal end of the pressure jacket. The at least one connector assembly may have at least one resiliently deflectable retaining member having a first segment attached to one of the syringe cap body and the pressure jacket body, and a second segment protruding from the first segment and deflectable relative to the first segment. The at least one connector assembly may further have at least one actuation member associated with the at least one resiliently deflectable retaining member. The at least one connector assembly may further have a radial lip defined on the other of the syringe cap body and the pressure jacket body. The at least one actuation member may interact with the radial lip when the syringe cap is connected to the pressure jacket to deflect the at least one resiliently deflectable retaining member upon rotation of the syringe cap relative to the pressure jacket during disengagement of the syringe cap from the pressure jacket.

Various aspects of the present disclosure may be further characterized by one or more of the following clauses:

Clause 1. A pressure jacket for use with a fluid injector and syringe, the pressure jacket comprising:

a pressure jacket body having a proximal end, a distal end, and a circumferential sidewall extending between the proximal end and the distal end along a pressure jacket longitudinal axis;

at least one resiliently deflectable retaining member having a first segment attached to the pressure jacket body and a second segment protruding from the first segment toward the distal end of the pressure jacket body and deflectable relative to the first segment; and at least one actuation member associated with the at least one resiliently deflectable retaining member, wherein the at least one actuation member interacts with a housing of the fluid injector when the pressure jacket is connected to the housing to deflect the at least one resiliently deflectable retaining member upon rotation of the pressure jacket relative to the housing during disengagement of the pressure jacket from the housing.

Clause 2. The pressure jacket according to clause 1, further comprising at least one alignment member associated with the pressure jacket body or the at least one resiliently deflectable retaining member, the at least one alignment member having an alignment surface for guiding the housing into self-orienting alignment with the pressure jacket during engagement of the pressure jacket with the housing.

Clause 3. The pressure jacket according to clause 2, wherein the at least one alignment member comprises a plurality of alignment members spaced apart around the pressure jacket longitudinal axis.

Clause 4. The pressure jacket according to clause 3, wherein the plurality of alignment members are spaced apart at equal radial intervals around the pressure jacket longitudinal axis.

Clause 5. The pressure jacket according to any of clauses 1-4, wherein the second segment of the at least one resiliently deflectable retaining member is deflectable radially relative to the first segment away from the pressure jacket longitudinal axis.

Clause 6. The pressure jacket according to any of clauses 1-5, wherein the at least one resiliently deflectable retaining member is linearly or curvilinearly contiguous between the first segment and the second segment.

Clause 7. The pressure jacket according to any of clauses 1-6, wherein the second segment of the at least one resiliently deflectable retaining member is angled toward the pressure jacket longitudinal axis.

Clause 8. The pressure jacket according to any of clauses 1-7, wherein the at least one actuation member is provided on a surface of the at least one resiliently deflectable retaining member.

Clause 9. The pressure jacket according to clause 8, wherein the at least one actuation member is at the second segment of the at least one resiliently deflectable retaining member.

Clause 10. The pressure jacket according to any of clauses 1-9, wherein the at least one actuation member is angled relative to a plane defined by a body of the at least one resiliently deflectable retaining member.

Clause 11. A syringe cap for use with a pressure jacket, the syringe cap comprising:

a syringe cap body having a proximal end, a distal end, and a circumferential sidewall extending between the proximal end and the distal end along a syringe cap longitudinal axis;

at least one resiliently deflectable retaining member having a first segment attached to the syringe cap body and a second segment protruding from the first segment toward the distal end of the syringe cap body and deflectable relative to the first segment; and at least one actuation member associated with the at least one resiliently deflectable retaining member, wherein the at least one actuation member interacts with the pressure jacket when the syringe cap is connected to the pressure jacket to deflect the at least one resiliently deflectable retaining member upon rotation of the syringe cap relative to the pressure jacket during disengagement of the syringe cap from the pressure jacket.

Clause 12. The syringe cap according to clause 11, further comprising at least one alignment member associated with the syringe cap body or the at least one resiliently deflectable retaining member, the at least one alignment member having an alignment surface for guiding the pressure jacket into self-orienting alignment with the syringe cap during engagement of the syringe cap with the pressure jacket.

Clause 13. The syringe cap according to clause 12, wherein the at least one alignment member comprises a plurality of alignment members spaced apart around the syringe cap longitudinal axis.

Clause 14. The syringe cap according to clause 13, wherein the plurality of alignment members are spaced apart at equal radial intervals around the syringe cap longitudinal axis.

Clause 15. The syringe cap according to any of clauses 11-14, wherein the second segment of the at least one resiliently deflectable retaining member is deflectable radially relative to the first segment away from the syringe cap longitudinal axis.

Clause 16. The syringe cap according to any of clauses 11-15, wherein the at least one resiliently deflectable retaining member is linearly or curvilinearly contiguous between the first segment and the second segment.

Clause 17. The syringe cap according to any of clauses 11-16, wherein the second segment of the at least one resiliently deflectable retaining member is angled toward the syringe cap longitudinal axis.

Clause 18. The syringe cap according to any of clauses 11-17, wherein the at least one actuation member is provided on a surface of the at least one resiliently deflectable retaining member.

Clause 19. The syringe cap according to claim 18, wherein the at least one actuation member is at the second segment of the at least one resiliently deflectable retaining member.

Clause 20. A pressure jacket and syringe cap assembly comprising;

a pressure jacket comprising a pressure jacket body having a proximal end, a distal end, and a circumferential sidewall extending between the proximal end and the distal end along a pressure jacket longitudinal axis;

a syringe cap comprising a syringe cap body having a proximal end, a distal end, and a circumferential sidewall extending between the proximal end and the distal end along a syringe cap longitudinal axis; and at least one connector assembly for releasably attaching the proximal end of the syringe cap to the distal end of the pressure jacket, the at least one connector assembly comprising:

at least one resiliently deflectable retaining member having a first segment attached to one of the syringe cap body and the pressure jacket body, and a second segment protruding from the first segment and deflectable relative to the first segment;

at least one actuation member associated with the at least one resiliently deflectable retaining member; and a radial lip defined on the other of the syringe cap body and the pressure jacket body, wherein the at least one actuation member interacts with the radial lip when the syringe cap is connected to the pressure jacket to deflect the at least one resiliently deflectable retaining member upon rotation of the syringe cap relative to the pressure jacket during disengagement of the syringe cap from the pressure jacket.

These and other features and characteristics of syringes, syringe plungers, pressure jackets, and systems having syringes, syringe plungers, and/or pressure jackets, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

BRIEF DESCRIPTION OF THE DRAWINGS

FIG. 15C is front perspective view of the piston shown in FIG. 15A and a plunger removed from the piston;

DETAILED DESCRIPTION

Figure 1:
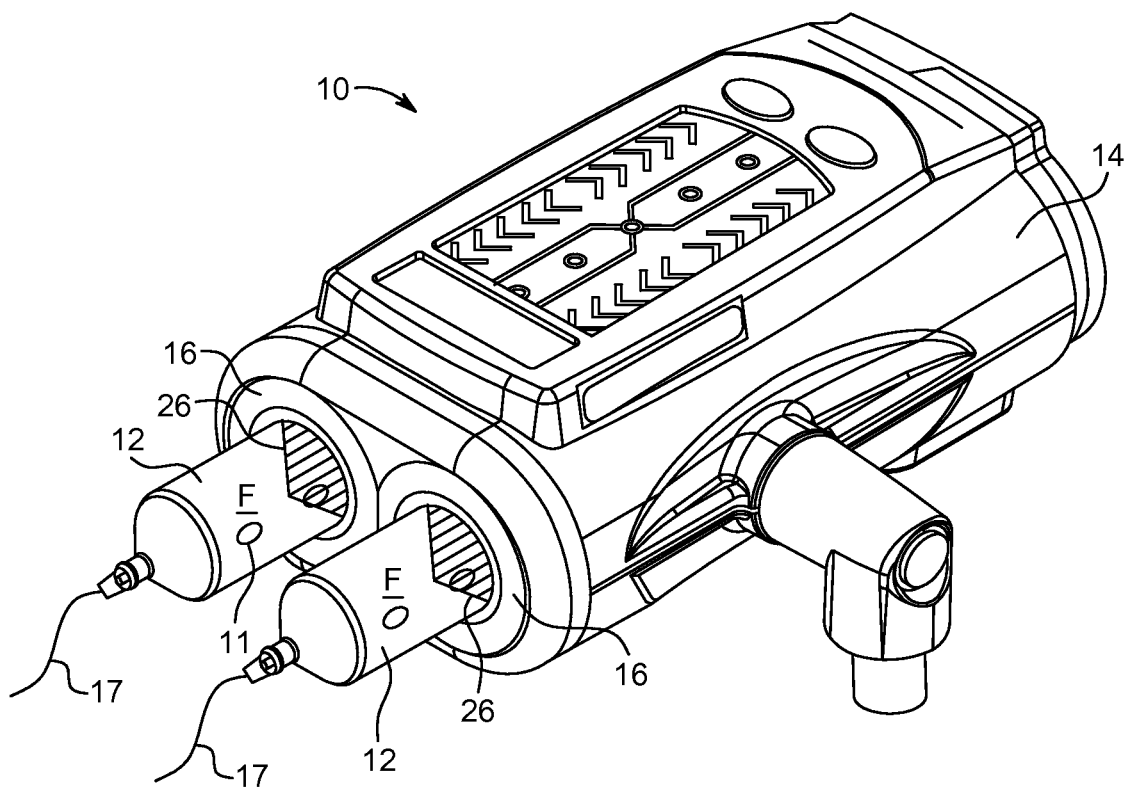
FIG. 1 is a top perspective view of a system including a fluid injector and a syringe according to an aspect of the present disclosure.

For purposes of the description hereinafter, the terms "upper", "lower", "right", "left", "vertical", "horizontal", "top", "bottom", "lateral", "longitudinal", and derivatives thereof shall relate to the components as they are oriented in the drawing figures. When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "self-orienting" means that a piston head or a plunger orients itself to a correct orientation relative to a plunger or piston head without a rotational effort by a technician or a fluid injector. It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

Referring to the drawings in which like reference characters refer to like parts throughout the several views thereof, the present disclosure is generally directed to syringe plunger and a connection interface for connecting the syringe plunger to a piston of a fluid injector. Various aspects are directed to syringe plungers that may be connected to and disconnected from the piston. In various aspects, such plungers may be manually, hydraulically, or electrically activated. Furthermore, the present disclosure provides a quick and easy solution for engaging and disengaging the syringe plunger to and from the piston without a specific orientation of the plunger relative to the piston. For example, the piston may be advanced forward until it engages with the plunger, regardless of orientation of the piston relative to the plunger along a longitudinal axis of the syringe, as will be described in greater detail herein. In addition, a simple angular rotation of the plunger relative to the piston at any orientation may allow for detachment of the two elements.

With reference to FIG. 1, a fluid injector 10 (hereinafter referred to as "injector 10"), such as an automated or powered fluid injector, is adapted to interface with and actuate at least one syringe 12, each of which may be independently filled with a medical fluid F, such as contrast media, saline solution, or any desired medical fluid. The injector 10 may be used during a medical procedure to inject the medical fluid into the body of a patient by driving a plunger 26 of the at least one syringe 12 with at least one piston. The injector 10 may be a multi-syringe injector, wherein several syringes 12 may be oriented in a side-by-side or other arrangement and include plungers 26 separately actuated by respective pistons associated with the injector 10. In aspects with two syringes arranged in a side-by-side relationship and filled with two different medical fluids, the injector 10 may deliver fluid from one or both of the syringes 12.

The injector 10 may be enclosed within a housing 14 formed from a suitable structural material, such as plastic or metal. The housing 14 may be of various shapes and sizes depending on the desired application. For example, the injector 10 may be a free-standing structure configured to be placed on the floor with a stationary or movable platform. Alternatively, the injector 10 may be configured for placement on a suitable table or support frame. The injector 10 includes at least one syringe port 16 for connecting the at least one syringe 12 to respective piston elements. As will be described hereinafter, in some aspects, the at least one syringe 12 includes at least one syringe retaining member for retaining the syringe 12 within the syringe port 16 of the injector 10. The at least one syringe retaining member operatively engages a locking mechanism provided on or in the syringe port 16 of the injector 10 to facilitate self-oriented loading and/or removal of the syringe 12 to and from the injector 10, as will be described herein. The syringe retaining member and the locking mechanism together define a connection interface for connecting the syringe 12 to the injector 10.

At least one fluid path set 17 may be fluidly connected with the at least one syringe 12 for delivering medical fluid F from the at least one syringe 12 to a catheter, needle, or other fluid delivery device (not shown) inserted into a patient at a vascular access site. Fluid flow from the at least one syringe 12 may be regulated by a fluid control module (not shown). The fluid control module may operate various, pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. One example of a suitable front-loading fluid injector that may be modified for use with the above-described system including at least one syringe and at least one syringe interface for self-oriented loading and releasable retaining of the at least one syringe with the fluid injector described herein with reference to FIG. 1 is disclosed in U.S. Pat. No. 5,383,858 to Reilly et al., which is incorporated by reference in its entirety. Another example of relevant multi-fluid delivery systems that may be modified for use with the present system are found in U.S. Pat. No. 7,553,294 to Lazzaro et al.; U.S. Pat. No. 7,666,169 to Cowan et al.; International Patent Publication No. WO 2012/155035; and United States Patent Application Publication No. 2014/0027009 to Riley et al.; the disclosures of which are incorporated herein by reference. Other aspects may include new fluid injector systems designed to include various aspects of the interface described herein.

Figure 2:
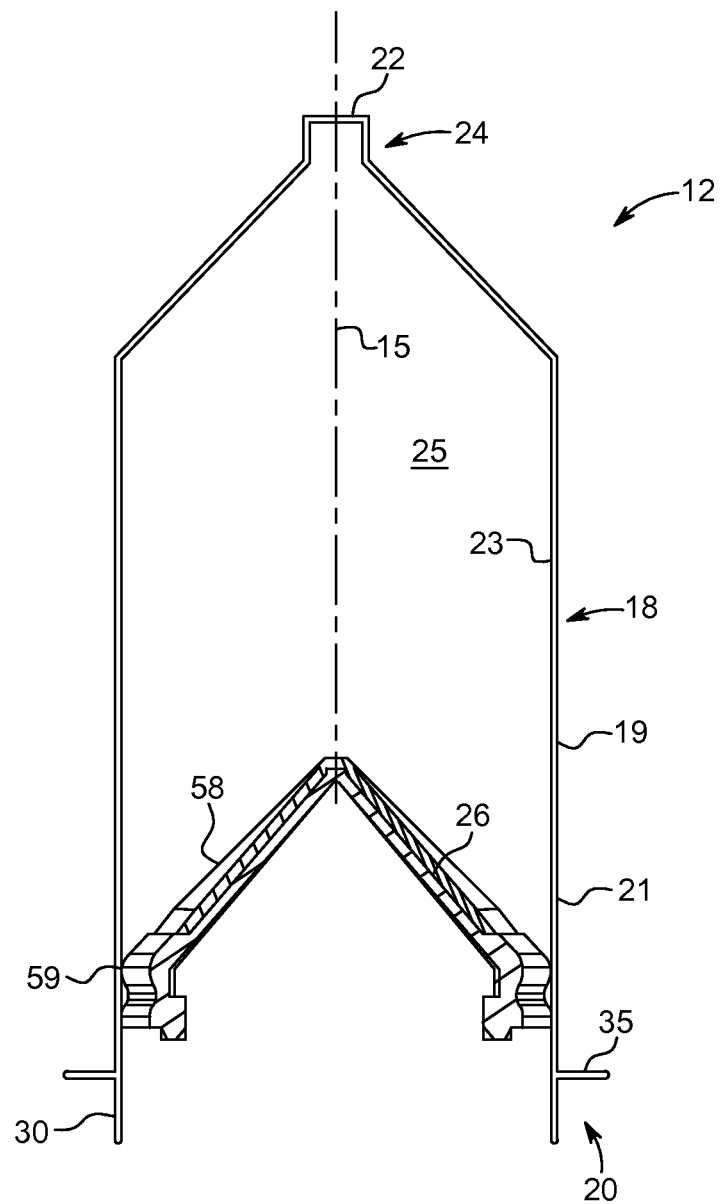
FIG. 2 is a side cross-sectional view of a syringe according to one aspect of the present disclosure.

Having described the general structure and function of the injector 10, the at least one syringe 12 will now by discussed in greater detail. With reference to FIG. 2, the syringe 12 generally has a cylindrical syringe barrel 18 formed from glass, metal, or a suitable medical-grade plastic. The barrel 18 has a proximal end 20 and a distal end 24, with a sidewall 19 extending therebetween along a length of a syringe longitudinal axis 15 extending through a center of the barrel 18. The barrel 18 may be made from a transparent or translucent material, and may include at least one fluid verification member 11 for verifying a presence of the fluid F within the syringe barrel 18. A nozzle 22 extends from the distal end 24 of the barrel 18. The barrel 18 has an outer surface 21 and an inner surface or wall 23 that defines an interior volume 25 for receiving the fluid therein. The proximal end 20 of the barrel 18 may be sealed with the plunger 26 that is slidable through the barrel 18. The plunger 26 forms a liquid-tight seal against the inner surface 23 of sidewall 19 of the barrel 18 as it is advanced therethrough.

A drip flange 35 may extend radially outwardly from the outer surface 21 of the syringe barrel 18 relative to the longitudinal axis 15. The drip flange 35 may extend around at least a portion of the outer circumference of the barrel 18. The drip flange 35 may prevent fluid that drips from the nozzle 22 from entering the syringe port 16 on the injector 10. In this manner, the drip flange 35 helps reduce the amount of fluid that may enter the syringe port 16 and jam or otherwise interfere with the connection interface and/or the interior mechanics and electronics of the injector 10. In some aspects, the drip flange 35 defines a stop surface that delimits the depth at which an insertion section 30 of the syringe 12 may be inserted into the syringe port 16 (shown in FIG. 1). The drip flange 35 may be formed integrally with the barrel 18 or it may be affixed or otherwise secured to the outer surface 21 of the barrel 18 using, for example, a frictional fit and/or an adhesive, welding, or by molding. In other aspects, the drip flange 35 may be formed on the outer surface 21 of the barrel 18 by etching, laser cutting, or machining.

With continued reference to FIG. 2, the proximal end 20 of the syringe 12 is sized and adapted for being removably inserted in the syringe port 16 of the injector 10 (shown in FIG. 1). In some aspects, the proximal end 20 of the syringe 12 defines the insertion section 30 that is removably inserteable into the syringe port 16 of the injector 10 while the remaining portion of the syringe 12 remains outside of the syringe port 16. In certain aspects, the proximal end 20 of the syringe 12 includes one or more syringe retaining members (not shown) adapted to form a locking engagement with a corresponding locking mechanism in the syringe port 16 of the injector 10 for releasably retaining the syringe 12 in the syringe port 16. Various retaining members for releasably locking the syringe 12 with the injector 10 are described in U.S. patent application Ser. No. 14/526,294, filed on Oct. 28, 2014 and entitled "Self-Orienting Syringe and Syringe Interface", and U.S. patent application Ser. No. 14/526,395, filed on Oct. 28, 2014 and entitled "Self-Orienting Syringe and Syringe Interface", the disclosures of which are incorporated herein by reference in their entirety.

Exemplary syringes suitable for use with the injector 10 depicted in FIG. 1 and which can be adopted for use with a fluid verification system are described in U.S. Pat. No. 5,383,858 to Reilly et al., which is assigned to the assignee of the present application, the disclosure of which is incorporated by reference in its entirety. Additional exemplary syringes are disclosed in U.S. Pat. No. 6,322,535 to Hitchins et al. and U.S. Pat. No. 6,652,489 to Trocki et al., each of which are assigned to the assignee of the present application, and the disclosures of which are both incorporated by reference in their entireties.

Figure 3A:
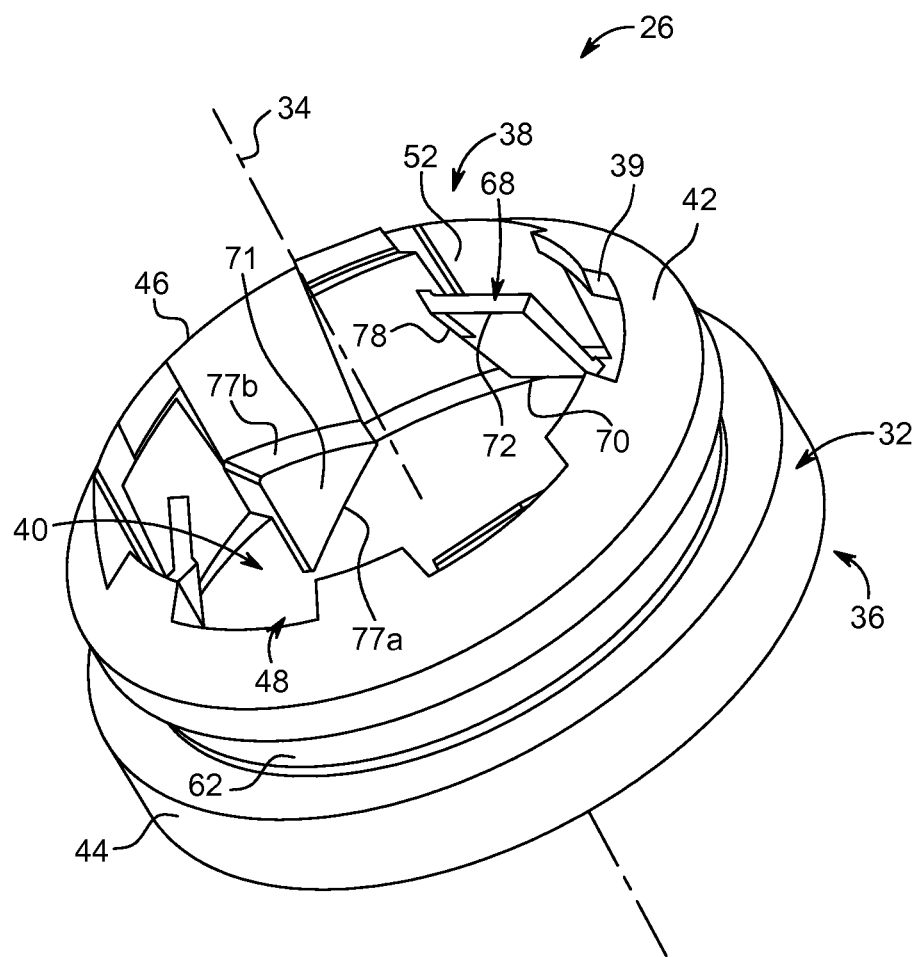
FIG. 3A is a top perspective view of a plunger according to one aspect of the present disclosure.
Figure 3B:
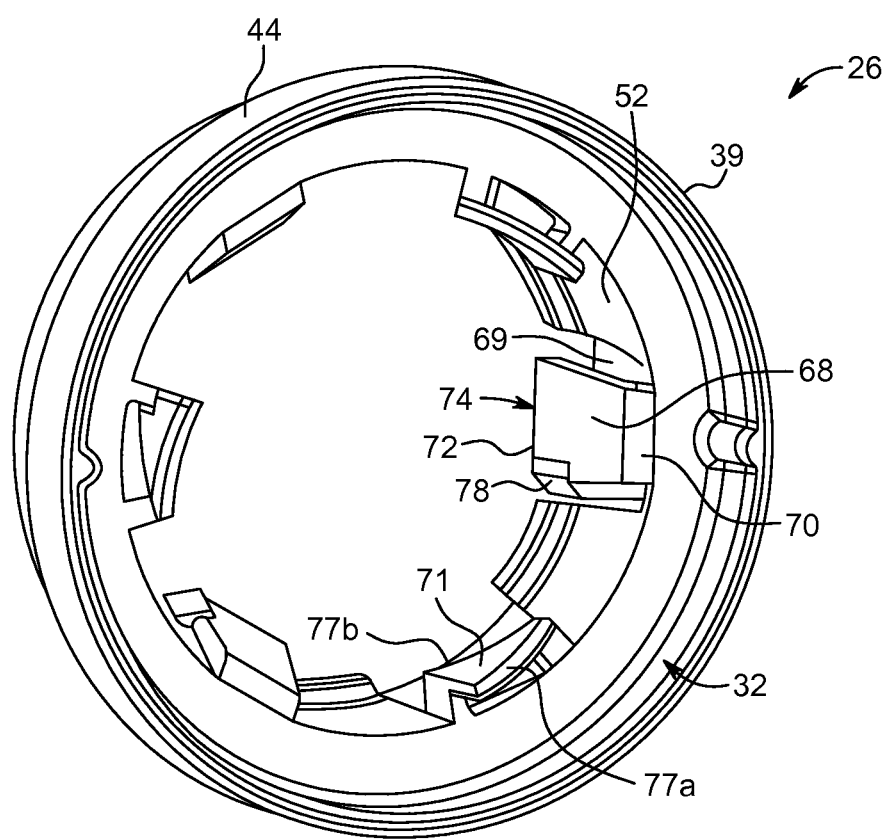
FIG. 3B is a bottom perspective view of the plunger shown in FIG. 3A.

With reference to FIGS. 3A-3B, the plunger 26 is shown in accordance with one aspect of the present disclosure. The barrel 18 of the syringe 12 is omitted from FIGS. 3A-3B for clarity. The plunger 26 includes a plunger body 32 defining a plunger longitudinal axis 34 and having a proximal end 36, a distal end 38, and a circumferential sidewall 39 connecting the proximal end 36 and the distal end 38. The sidewall 39 may have a uniform or non-uniform thickness between the proximal end 36 and the distal end 38. The sidewall 39 may have a continuous outer surface. In some aspects, the sidewall 39 may have a discontinuous outer surface having one or more portions of sidewall 39 separated by one or more voids. The plunger body 32 may be formed from glass, metal, plastic, or other suitable material.

With continued reference to FIGS. 3A-3B, the plunger body 32 has an interior cavity 40 defined by a conical-shaped portion 42 at the distal end 38 of the plunger body 32 and a cylindrical-shaped portion 44 at the proximal end 36 of the plunger body 32. The conical-shaped portion 42 may be monolithically formed with the cylindrical-shaped portion 44. In some aspects, the conical-shaped portion 42 may be affixed or otherwise secured to the cylindrical-shaped portion 44 of the plunger body 32 using, for example, a frictional fit and/or an adhesive, welding, or by molding. The conical-shaped portion 42 may have a truncated end 46 that has a central opening 48. In some aspects, the distal end 38 of the plunger body 32 may be enclosed such that the plunger 26 does not have a central opening 48.

Figure 3C:
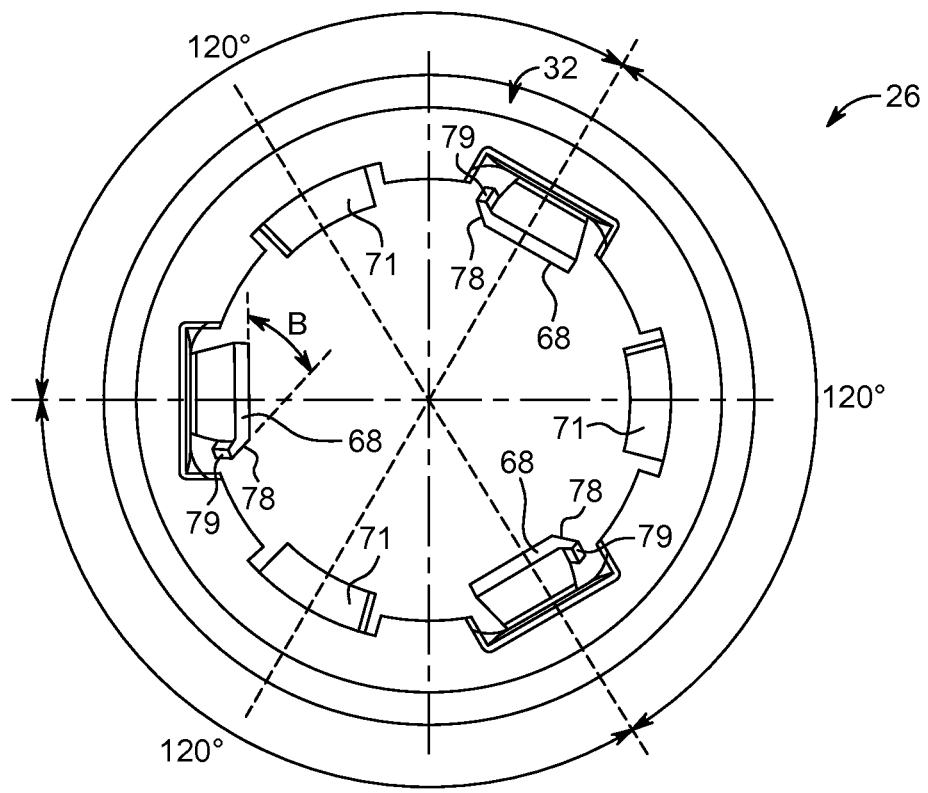
FIG. 3C is a bottom view of the plunger shown in FIG. 3A.
Figure 3D:
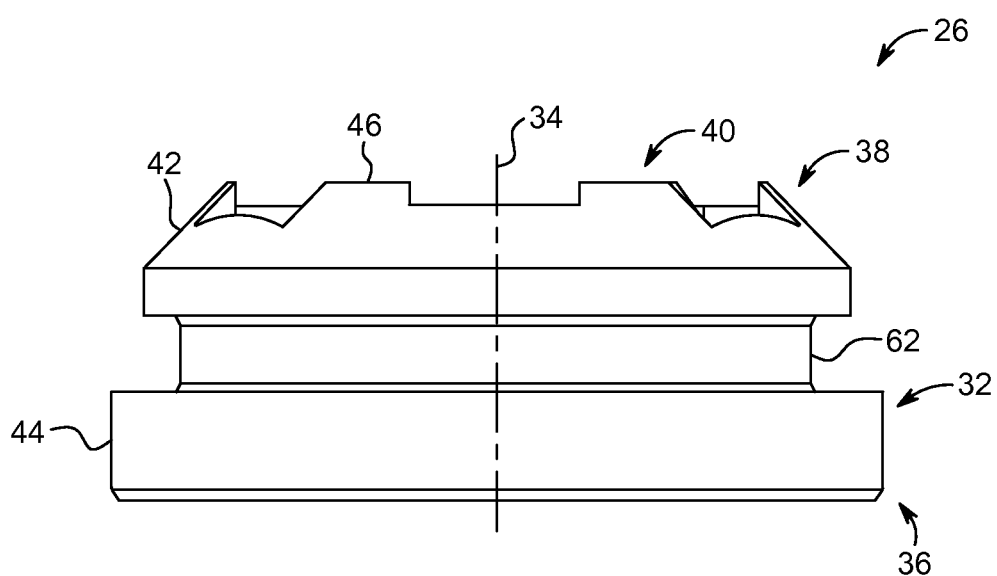
FIG. 3D is a side view of the plunger shown in FIG. 3A.
Figure 3E:
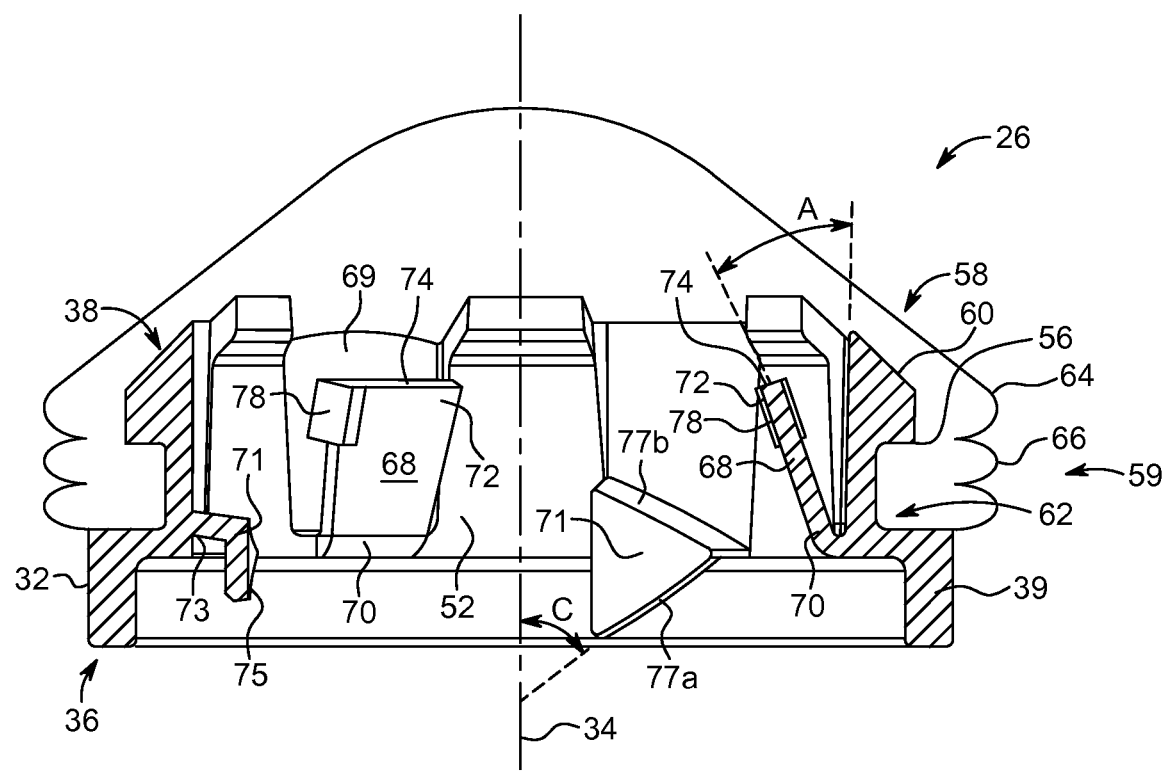
FIG. 3E is a side cross-sectional view of the plunger shown in FIG. 3A.

With reference to FIG. 3E, the plunger 26 may have a seal 58 that covers at least a portion of an outer surface 60 of the plunger body 32. The seal 58 may be a flexible seal that engages an inner surface of the syringe barrel 18 (shown in FIG. 2) such that the seal 58 seals the interior volume 25 of the syringe barrel 18 in a liquid-tight manner. The seal 58 may be provided separately from the plunger body 32, or it may be integrally formed with the plunger body 32, such as by co-molding. In some aspects, the outer surface 60 of the plunger body 32 may have a circumferential groove 62. At least a portion of seal 58 may be retained within the circumferential groove 62. The exterior surface 64 of the seal 58 may have one or more lips, projections, or other sealing elements 66 that slidingly engage an inner surface of the syringe barrel 18. In some aspects, at least the sealing elements 66 of the seal 58 may be made from an elastomeric material that resiliently engages the inner surface 23 of the syringe barrel 18. The at least one extension 56 on the plunger body 32 may prevent the seal 58 from coming out of axial engagement with the syringe 12 as the plunger 26 is moved through the syringe barrel 18.

Referring again to FIGS. 3A-3B, the plunger 26 may have at least one resiliently deflectable retaining member 68 (hereinafter "retaining member 68") protruding from the plunger body 32. In some aspects, the at least one retaining member 68 may protrude in a direction from the proximal end 36 toward the distal end 38 of the plunger body 32. In some aspects, the at least one retaining member 68 may protrude distally and radially inward from an inner surface 52 of the interior cavity 40 of the plunger body 32.

With reference to FIG. 3E, the at least one retaining member 68 has a first end 70 connected to the plunger body 32 and a second end 72 protruding distally from the first end 70. The second end 72 may deflect or twist relative to the first end 70. As described herein, the second end 72 may be radially deflectable relative to the first end 70 when the at least one retaining member 68 engages a piston of the fluid injector 10. In some aspects, the second end 72 may be circumferentially deflectable relative to the first end 70. The first end 70 and the second end 72 may be spaced apart in a direction that extends substantially along a direction of the plunger longitudinal axis 34 of the plunger 26. The at least one retaining member 68 may be linearly, stepwise, or curvilinearly contiguous between the first end 70 and the second end 72. In some aspects, one or more retaining members 68 may extend in a direction parallel to a direction of the plunger longitudinal axis 34. In other aspects, one or more retaining members 68 may extend in a direction that is angled relative to the direction of the plunger longitudinal axis 34. For example, one or more retaining member 68 may be angled at an angle A toward or away from inner surface 52 of the plunger body 32. The inner surface 52 of the plunger body 32 may have one or more pockets 69 that are recessed in a radially inward direction into the sidewall 39 to allow for an increased deflection of the second end 72 relative to the first end 70 of the at least one retaining member 68.

With reference to FIG. 3C, a plurality of retaining members 68 may spaced apart radially relative to the plunger longitudinal axis 34 along a circumference of the inner surface 52 of the interior cavity 40. The retaining members 68 may be separated from each other by portions of the inner surface 52 of the interior cavity 40. In aspects where two or more retaining members 68 are provided, the retaining members 68 may be evenly spaced apart from each other. In one exemplary and non-limiting aspect with three retaining members 68 having equal angular separation therebetween, such as shown in FIG. 3C, each retaining member 68 is separated by 120 degrees from the retaining members 68 adjacent on either side. In some aspects, the retaining members 68 may have unequal angular extension and/or unequal angular spacing between the retaining members 68 about the inner surface 52 of the interior cavity 40. The radial spacing of the at least one retaining member 68 relative to the plunger longitudinal axis 34 is selected to correspond to or operably interact with an outer shape of the piston, as described herein.

With continued reference to FIG. 3E, the second end 72 of the retaining member 68 has at least one catch 74. The at least one catch 74 may be a terminal surface of the second end 72 of the retaining member 68. As described herein, the at least one catch 74 is shaped to be received within at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 72 of the at least one retaining member 68 or it may be affixed or otherwise secured to the second end 72 of the at least one retaining member 68 using, for example, a frictional fit and/or an adhesive, welding, or by molding. In other aspects, the at least one catch 74 may be formed on the second end 72 of the at least one retaining member 68 by etching, laser cutting, or machining.

With reference to FIGS. 3A-3B, the plunger 26 may have at least one first cam member 78. In some aspects, the first cam member 78 may be provided directly on the retaining member 68, or it may be provided on a portion of the plunger body 32 such that activation of the cam member 78 causes a corresponding activation of the retaining member 68. In some aspects, the at least one first cam member 78 may be provided between the first end 70 and the second end 72 of the retaining member 68. The at least one first cam member 78 interacts with a piston of the fluid injector 10 (shown in FIG. 1) to radially deflect the at least one retaining member 68 upon rotation of the plunger 26 relative to the piston, as described herein. In some aspects, the position of the at least one first cam member 78 may be selected to allow for an increased radial deflection of the at least one first cam member 78 upon relative rotation between the plunger 26 and the piston. In such aspects, the at least one first cam member 78 may be provided closer to the second end 72 of the retaining member 68.

In some aspects, the at least one first cam member 78 may protrude at an angle relative to a plane defined by a body of the retaining member 68. With reference to FIG. 3C, the at least one first cam member 78 may be angled at an angle B relative to the plane defined by the body of the retaining member 68. The at least one first cam member 78 may have an angled engagement surface 79 that interacts with the piston to disengage the plunger 26 from the piston, as described herein. The position of the at least one first cam member 78 between the first end 70 and the second end 72 of the retaining member 68 minimizes the radial protrusion of the at least one first cam member 72 while still allowing a full radial deflection of the at least one retaining member 68 upon rotation of the plunger 26 relative to the piston 88, as described herein. In some aspects, the at least one first cam member 78 may be provided on at least a portion of the at least one catch 74. A plurality of first cam members 78 may be axially spaced apart along a length of the retaining member 68 between the first end 70 and the second end 72. The at least one first cam member 78 may be formed integrally with the at least one retaining member 68 or it may be affixed or otherwise secured to the at least one retaining member 68 using, for example, a frictional fit and/or an adhesive, welding, or by molding. In other aspects, the at least one first cam member 78 may be formed on the at least one retaining member 68 by etching, laser cutting, or machining.

With reference to FIG. 3A, the plunger 26 may have at least one first alignment member 71 protruding from the plunger body 32. In some aspects, the at least one first alignment member 71 may protrude in a direction from the distal end 38 toward the proximal end 36 of the plunger body 32. In some aspects, the at least one first alignment member 71 may protrude proximally from the inner surface 52 of the interior cavity 40 of the plunger body 32.

With reference to FIG. 3E, the at least one first alignment member 71 has a first end 73 connected to the plunger body 32 and a second end 75 protruding proximally from the first end 73. The at least one first alignment member 71 is shaped and/or configured for facilitating self-orienting alignment of the plunger 26 with the piston 88. In some aspects, at least a portion of the at least one first alignment member 71 may extend in a direction that is angled relative to the direction of the plunger longitudinal axis 34. For example, at least one first alignment member 71 may have a proximal alignment surface 77a that is angled at an angle C relative to the longitudinal axis 34 to facilitate positioning of the retaining member 68 during connection of the plunger 26 to a piston. The at least one first alignment member 71 may have a distal alignment surface 77b that is angled in a direction opposite to the proximal alignment surface 77a to facilitate positioning of the retaining member 68 when the plunger 26 is being disconnected from the piston. The proximal alignment surface 77a helps guide the plunger 26 into self-orienting alignment with the piston, as described herein.

With reference to FIG. 3C, a plurality of first alignment members 71 may be spaced apart radially relative to the plunger longitudinal axis 34 along a circumference of the inner surface 52 of the interior cavity 40. In some aspects, the number of first alignment members 71 may be equal or unequal to the number of retaining members 68. When equal in number, the first alignment members 71 may be disposed between the retaining members 68 such that each first alignment member 71 has a retaining member 68 on either side of the first alignment member 71. The first alignment members 71 may be separated from each other by portions of the inner surface 52 of the interior cavity 40. In aspects where two or more first alignment members 71 are provided, the first alignment members 71 may be evenly spaced apart from each other. In one exemplary and non-limiting aspect with first alignment members 71 having equal angular separation therebetween, such as shown in FIG. 3C, each first alignment member 71 is separated by 120 degrees from the first alignment members 71 adjacent on either side. In some aspects, the first alignment members 71 may have unequal angular extension and/or unequal angular spacing between the first alignment members 71 about the inner surface 52 of the interior cavity 40. The radial spacing of the at least one first alignment member 71 relative to the plunger longitudinal axis 34 is selected to correspond to or operably interact with an outer shape of the piston to allow for alignment of the piston with the plunger 26, as described herein.

Figure 4A:
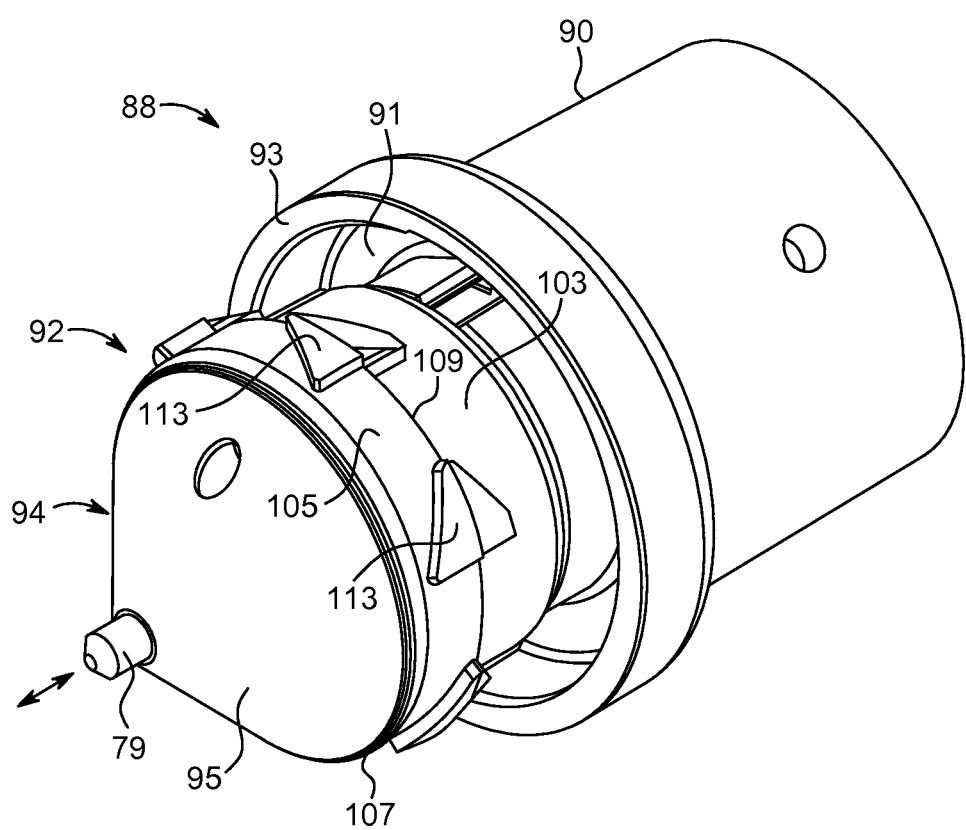
FIG. 4A is a front perspective view of a piston according to one aspect.

Referring to FIG. 4A, a piston 88 is configured to interact with the plunger 26 (shown in FIG. 3A) to releasably lock the plunger 26 such that the plunger 26 can be driven reciprocally within the barrel of the syringe 12 (shown in FIG. 2). The piston 88 is extendible and retractable from the housing 14 of the fluid injector 10 (shown in FIG. 1) via a powered means (not shown) preferably contained within housing 14. The powered means may include, for example, an electric motor, hydraulic system, or a pneumatic system, including appropriate gearing (not shown). As known in the art, the fluid injector 10 also may include a controller (not shown) for controlling operation of the powered means and thereby controlling operation of the piston 88.

With continued reference to FIG. 4A, the piston 88 includes a stem 90 and a piston head 92 formed on a distal end of the stem 90. At least a portion of the piston head 92 extends distally the stem 90. The piston 88 is construed from a rigid material, such as metal or plastic that resists deformation. The stem 90 may have a cavity 91 for collecting any fluid that may drip from the syringe. The piston head 92 has a substantially cylindrical structure with a pointed distal end 94 with a cap 95 that is shaped to be received inside at least a portion of the interior cavity 40 (shown in FIG. 3A) of the plunger 26. In some aspects, a sensing member 79, such as a pin connected to a sensor, may be provided. The sensing member 79 may extend along a longitudinal axis of the piston 88 and may protrude through at least a portion of the piston head 92, such as through at least a portion of the cap 95. The sensing member 79 may be operative for sensing contact with a surface, such as a surface of the plunger 26, and control a movement of the piston 88 based on the sensed condition. For example, an initial contact between the sensing member 79 and the plunger 26 may cause the pin to be moved in a proximal direction such that it makes contact with the sensor. The sensing member 79 may be biased in an extended position by a resilient element 81 (shown in FIG. 4B), such as a spring. The sensor may be connected to the controller of the injector such that, upon activation of the sensor by the pin, the controller controls the movement of the drive mechanism. For example, the drive mechanism may be stopped or slowed from a first rate to a second, slower rate.

The piston head 92 may be rotatable relative to the stem 90. In some aspects, the piston head 92 may be rotatable in one direction only, such as a clockwise or a counterclockwise direction, relative to the stem 90. A one-way rotation mechanism 99, such as a one-way clutch mechanism, may be provided to allow the rotation of the piston head 92 in a first direction only, such as the clockwise or the counterclockwise direction. The one-way rotation mechanism 99 may be rotatable around a central shaft 101 having a seal 102, such as an O-ring seal. In some aspects, the one-way rotation mechanism 99 may have a stop that prevents rotation of the piston head 92 in a second direction opposite the first direction, such as the counterclockwise or the clockwise direction, respectively. In other aspects, the one-way rotation mechanism 99 may be provided on at least a portion of the plunger 26.

Figure 4B:
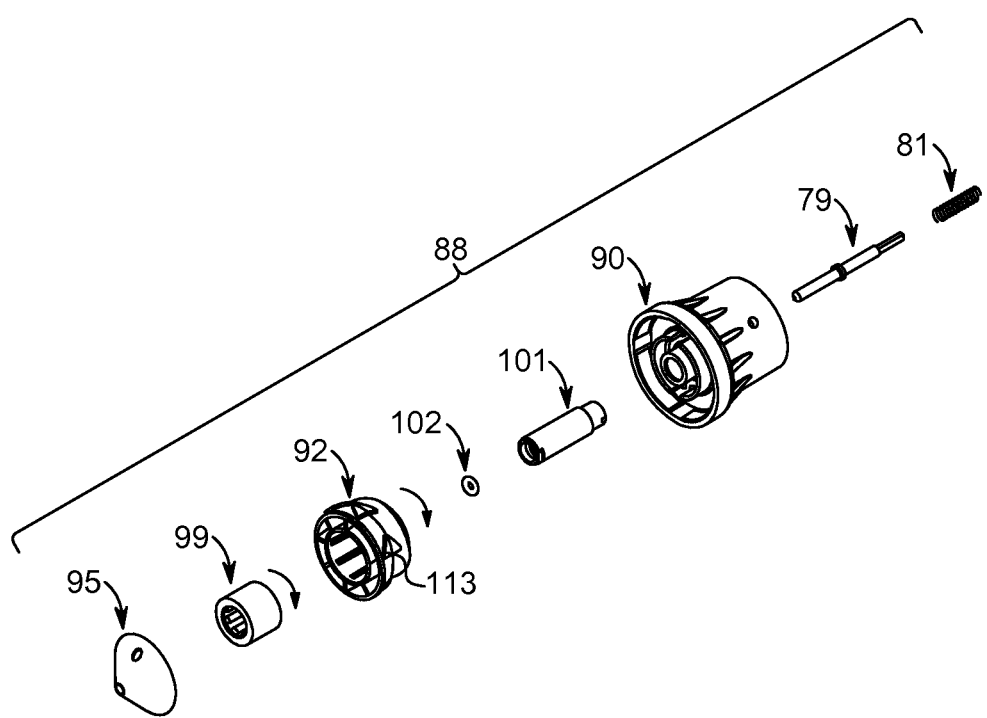
FIG. 4B is an exploded perspective view of a piston showin in FIG 4A.
Figure 4C:
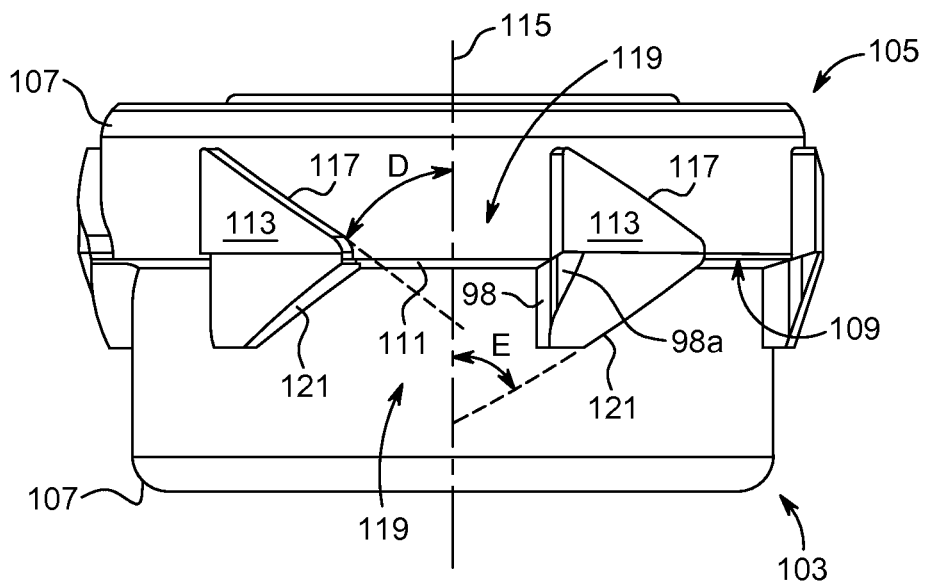
FIG. 4C is a side view of the piston head of the piston shown in FIG. 4A.

With reference to FIG. 4C, the piston head 92 has a proximal portion 103 connected to a distal portion 105. Terminal ends of the proximal and distal portions 103, 105 may have a radiused edge 107. At least a portion of the proximal portion 103 has a smaller outer diameter compared to an outer diameter of the distal portion 105 such that a radial lip 109 is formed at a transition between the proximal portion 103 and the distal portion 105. The radial lip 109 may be continuous or discontinuous around a circumference of the piston head 92. In some aspects, the radial lip 109 defines a locking ledge 111 for engaging the catch 74 of the at least one retaining member 68 when the plunger 26 is fully seated on the piston head 92.

With continued reference to FIG. 4C, the piston head 92 may have at least one second alignment member 113 protruding radially outward from an outer surface of the piston head 92. The at least second alignment member 113 is shaped and/or configured for interacting with the first alignment member 71 of the plunger 26 the facilitating alignment of the piston 88 with the plunger 26 in order to allow for a releasable locking connection of the plunger 26 with the piston 88. In some aspects, at least a portion of the at least second alignment member 113 may extend in a direction that is angled relative to the direction of a piston longitudinal axis 115. For example, at least second alignment member 113 may have a guiding surface 117 that is angled at an angle D relative to the piston longitudinal axis 115. The guiding surface 117 is desirably angled such that the piston head 92 may rotate around the piston stem 90 when the proximal alignment surface 77a of the first alignment member 71 contacts the guiding surface 117 of the second alignment member 113.

In some aspects, a plurality of second alignment member 113 may be spaced apart radially relative to the piston longitudinal axis 115 along an outer circumference of the piston head 92. In some aspects, the number of second alignment member 113 may be equal to a total number of retaining members 68 and first alignment members 71 on the plunger 26. The second alignment member 113 are spaced apart circumferentially such that a retaining member 68 or a first alignment member 71 may be received between adjacent second alignment members 113. The second alignment members 113 may be separated from each other by portions of an outer surface of the proximal portion 103 and/or the distal portion 105 of the piston head 92. In aspects where two or more second alignment members 113 are provided, the second alignment members 113 may be evenly spaced apart from each other. In one exemplary and non-limiting aspect with second alignment members 113 having equal angular separation therebetween, such as shown in FIG. 4A, each second alignment member 113 is separated by 60 degrees from the second alignment members 113 adjacent on either side. In some aspects, the second alignment members 113 may have unequal angular extension and/or unequal angular spacing between the second alignment members 113 about the outer surface of the proximal portion 103 and/or the distal portion 105 of the piston head 92. The radial spacing of the at least one second alignment members 113 relative to the piston longitudinal axis 115 is selected to correspond to or operably interact with an inner shape of the plunger 26 to allow the retaining members 68 and the first alignment members 71 to be received between adjacent second alignment members 113, as described herein.

Each of the guiding surfaces 117 of the second alignment members 113 define a travel path for guiding the movement of the proximal alignment surface 77a of the first alignment member 71 in and out of a recess 119 defined between adjacent second alignment members 113. The guiding surfaces 62 and 65 may be inclined or angled radially and axially relative to the piston longitudinal axis 115 to guide the movement of the proximal alignment surfaces 77a. The guiding surfaces 117 aid in self-orienting the piston head 92 as the plunger 26 is brought into contact with the piston 88 by guiding the one or more proximal alignment surfaces 77a on the plunger 26 into the corresponding recess 119 on the piston head 92. In this manner, a piston 88 whose piston longitudinal axis 115 is rotationally misaligned with the plunger longitudinal axis 34 and the one or more first alignment member 71 which are initially misaligned relative to the corresponding one or more second alignment members 77a in a rotational direction are brought in alignment axially and rotationally such that the one or more first alignment members 71 are received within the recess 119 between adjacent second alignment members 113.

The one or more second alignment members 113 may have a bottom surface 121 that is angled relative to the direction of a piston longitudinal axis 115. For example, the bottom surface 121 may be angled at an angle E relative to the piston longitudinal axis 115. Angle E may be the same or different than angle E of the guiding surface 117.

The piston head 92 further has a second cam member 98. In some aspects, the second cam member 98 cooperates with the first cam member 78 on the at least one retaining member 68 of the plunger 26, as described herein. The second cam member 98 desirably has a shape that, upon relative rotation between the piston 88 and the plunger 26, engages the first cam member 78 to cause the at least one retaining member 68 to be deflected from the piston head 92 such that the plunger 26 can be removed from the piston 88. In some aspects, the second cam member 98 may be formed on the second alignment member 113 on the piston head 92. The second cam member 98 may be a surface that is aligned with a direction of the piston longitudinal axis 115. The second cam member 98 may have a chamfered portion 98a to facilitate passing of the first cam member 78 after the retaining member 68 is deflected sufficiently to allow the retaining member to be released.

Figure 5A:
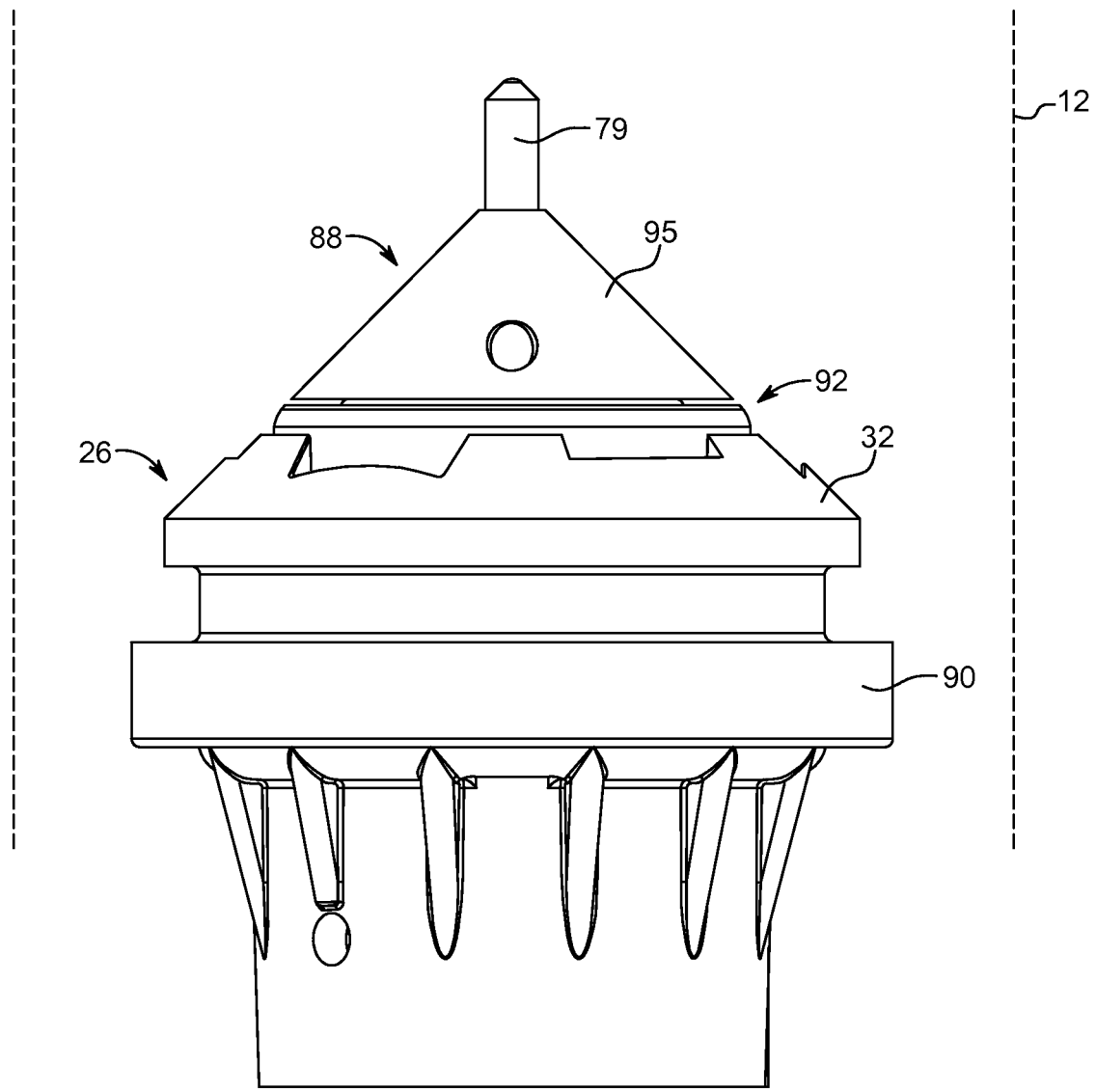
FIG. 5A is a side view of a plunger and a piston in an assembled state.

The piston 88 is configured to interact with the plunger 26 to releasably lock with plunger 26, such as shown in FIG. 3A. By locking the piston 88 to the plunger 26, the plunger 26 can be driven reciprocally within the barrel of the syringe 12 (shown in FIG. 2). The second cam member 98 on the piston 88 cooperates with the first cam member 78 on the at least one retaining member 68 of the plunger 26, to releasably lock the plunger 26 to the piston 88. The locking or engagement of the plunger 26 to the piston 88, and the unlocking or disengagement of the plunger 26 from the piston 88 will be described herein with reference to FIGS. 5A-5C. The syringe 12, shown initially in phantom in FIG. 5A is omitted from the remainder of FIGS. 5B-5D for clarity.

To engage the plunger 26 with the piston 88, the syringe 12 is first inserted into the syringe port 16 of the fluid injector 10 (shown in FIG. 1). Once the syringe 12 is inserted into the syringe port 16, various locking mechanisms (not shown) may be used to retain the syringe 12 within the syringe port 16 to prevent detachment of the syringe 12 from the syringe port 16. Initially, the plunger 26 may be positioned at the proximal end 20 of the syringe barrel 18. In some aspects, the plunger 26 is positioned at any axial location between the proximal end 20 and the distal end 24 of the syringe barrel 18. The piston 88 may then be advanced distally toward the plunger 26 for engagement of the piston head 92 with the plunger 26. In some aspects, the piston 88 may be advanced distally toward the plunger 26 by way of the powered means operated by a controller. In other aspects, the piston 88 may be advanced distally toward the plunger 26 by manual operation.

Figure 5B:
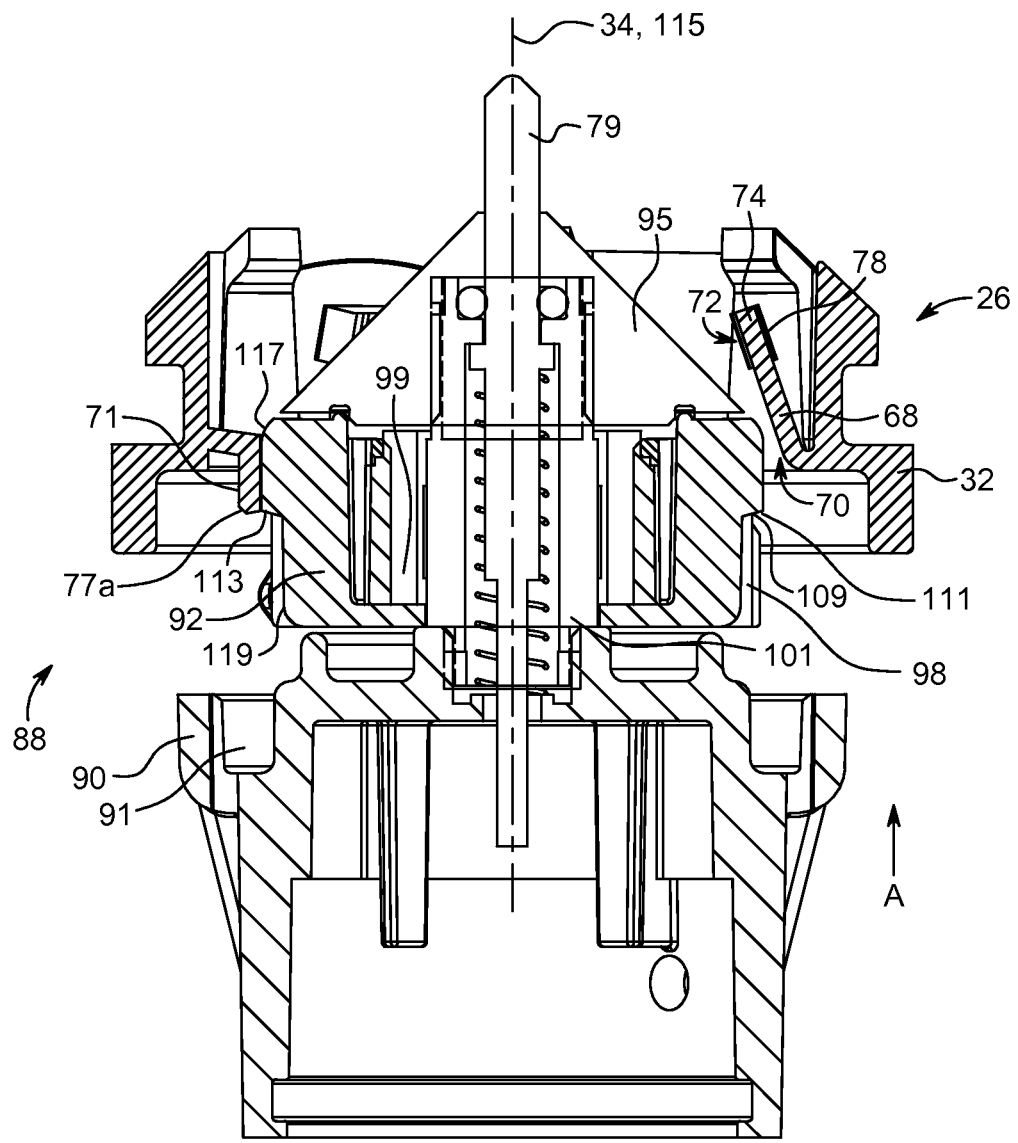
FIG. 5B is a side cross-sectional view of the plunger and the piston during initial engagement of the piston with the plunger.

With reference to FIG. 5B, the piston 88 is advanced axially in a distal direction shown by the arrow A. If the piston 88 is rotationally misaligned relative to the plunger 26 such that the first alignment members 71 on the plunger 26 are not in rotational alignment to be received within the recesses 119 (shown in FIG. 4C) on the plunger head 92, the proximal alignment surface 77a of the first alignment member 71 on the plunger 26 contacts the guiding surface 117 of the second alignment member 113 on the piston head 92. The proximal alignment surface 77a and the guiding surface 117 are angled in a same direction relative to the longitudinal axes 34, 115 such that continued movement of the piston 88 in a distal direction causes the proximal alignment surface 77a to engage the guiding surface 117. Engagement of the proximal alignment surface 77a with the guiding surface 117 causes the piston head 92 to automatically rotate in a free rotation direction of the one-way rotation mechanism 99. Such rotation of the piston head 92 aligns the first alignment members 71 and the retaining members 68 to be received within the recesses 119 between adjacent second alignment members 113. In this manner, the piston 88 self-orients itself relative to the plunger 26 such that the plunger 26 may be releasably locked with the piston 88. If the piston 88 is rotationally aligned relative to the plunger 26 such that the first alignment members 71 on the plunger 26 are in rotational alignment second alignment members 113 on the plunger head 92, the first alignment members 71 and the retaining members 68 on the plunger 26 can be received within the recesses 119 between adjacent second alignment members 113 without rotation of the piston head 92.

Figure 5C:
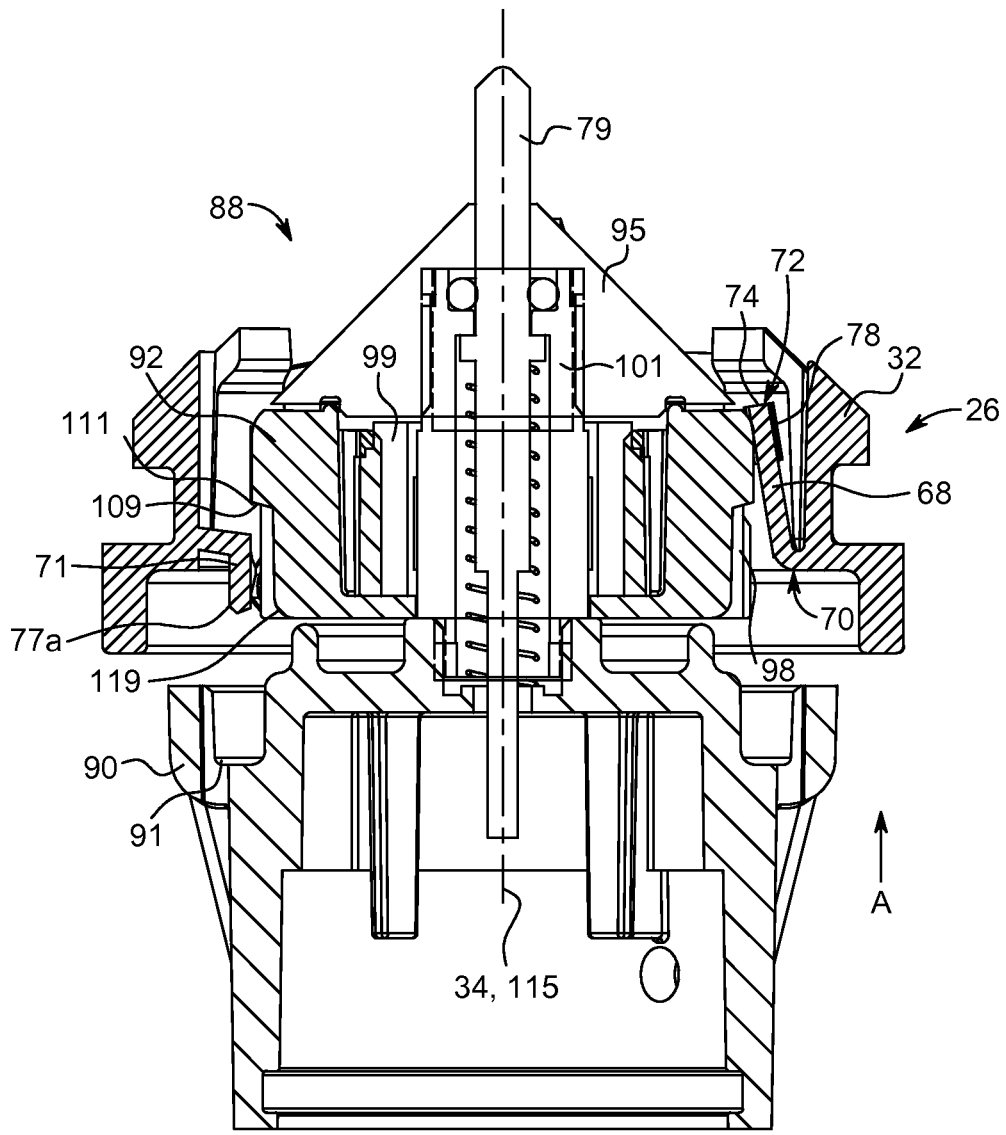
FIG. 5C is a side cross-sectional view of the plunger and the piston prior to full engagement of the piston with the plunger.
Figure 5D:
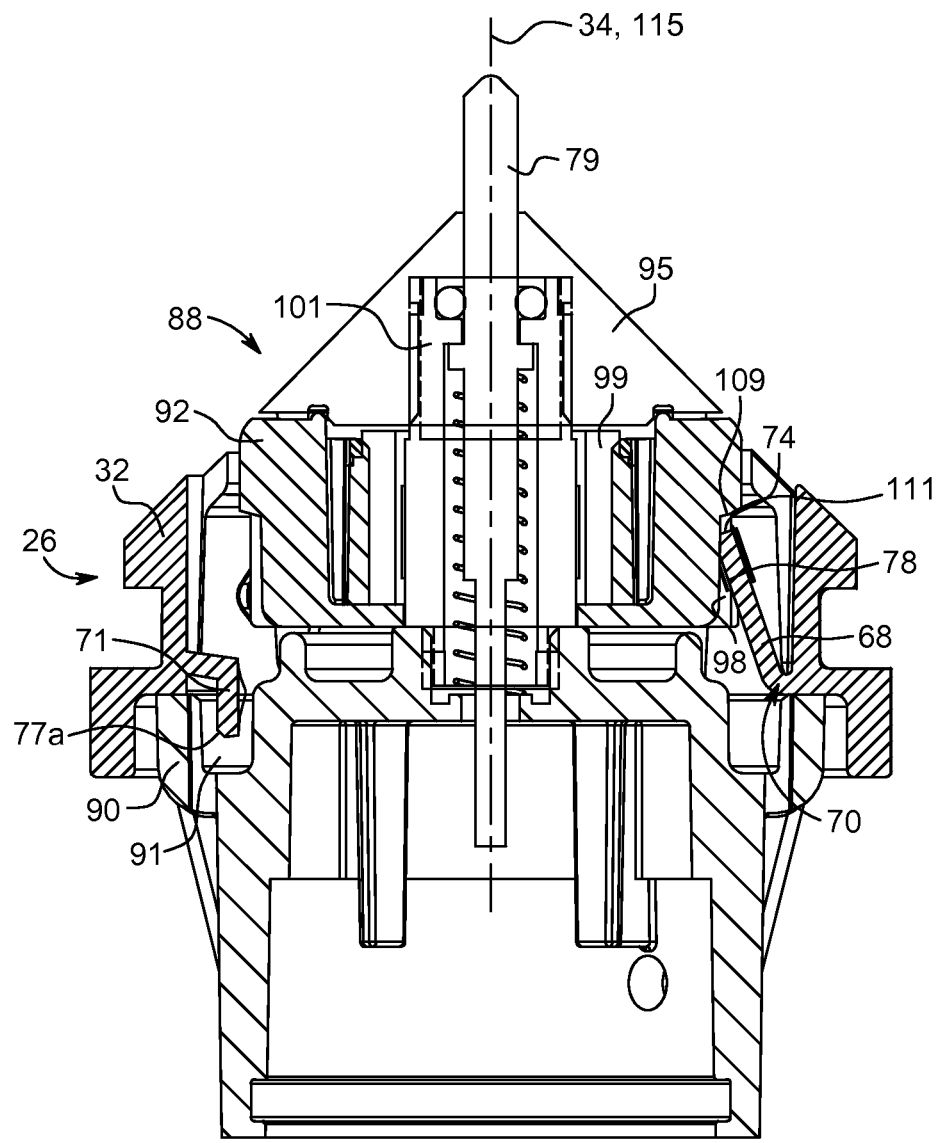
FIG. 5D is a side cross-sectional view of the plunger and the piston during full engagement of the piston with the plunger.

With reference to FIG. 5C, after aligning the first alignment members 71 and the retaining members 68 to be received within the recess 119 between adjacent second alignment members 113, the piston 88 is advanced further in the distal direction. Such movement of the piston 88 distal direction, causes the retaining members 68 to initially engage an outer sidewall of the distal portion 105 of the piston head 92. Continued distal movement of the piston 92 causes the retaining members 68 to deflect radially outward relative to the plunger longitudinal axis 34 from a first, undeflected position, to a second, radially deflected position. The piston 88 is advanced distally until the terminal portion of the second end 72 clears the radial lip 109. The retaining members 68 then deflect radially inward toward or to their initial undeflected position. As shown in FIG. 5D, the catch 74 of at least one retaining member 68 is retained within the locking ledge 111 to prevent disengagement of the plunger 26 from the piston head 92. Distal movement of the piston 88 may be stopped when the sensing member 79 engages at least a portion of the plunger 26, such as the plunger cover 58 (shown in FIG. 3E). The plunger 26 resists disconnection from the piston 88 upon movement of piston 88 in a distal and proximal direction relative to the syringe barrel 18. In one aspect, the retaining members 68 may be designed such that the compressive forces exerted upon the catch 74 upon movement of piston head 92 in the proximal direction substantially prevent radially outward deflection (or bending) of the retaining members 68. For example, once the retaining members 68 are locked to the piston head 92, axial movement of the piston 88 does not introduce a bending moment sufficient to deflect the retaining members 68 radially to cause the plunger 26 to be disconnected from the piston 88. Proximal movement of the piston 88 causes the at least one retaining member 68 to be loaded in compression between the first end 70 and the second end 72 such that the retaining member 68 may be urged in a radially inward direction, thereby increasing the locking force between the plunger 26 and the piston 88.

To unlock the syringe 12 from the syringe port 16 and disengage the plunger 26 from the piston 88, the syringe 12 is rotated clockwise or counterclockwise about the syringe longitudinal axis, in a clockwise or counter-clockwise direction, relative to the syringe port 16. Because the plunger 26 is substantially free from rotation within the syringe barrel 18, the rotation of the syringe 12 also causes the plunger 26 to rotate relative to the piston 88. The free-rotation direction of the one-way rotation mechanism 99 is desirably opposite to the rotation direction of the syringe 12 during the release of the syringe 12 from the syringe port 16. Rotation of the syringe 12, and thereby the plunger 26, about the plunger longitudinal axis 34 engages the first cam member 78 on the plunger 26 with the second cam member 98 on the piston head 92. Such movement causes a radial deflection of the at least one retaining member 68 away from the piston head 92.

As the at least one retaining member 68 is deflected radially outward relative to the plunger longitudinal axis 34, the catch 74 is moved out of engagement with the locking ledge 111. In this position, the at least one retaining member 68 is in a deflected state that allows the plunger 26 to be moved axially relative to the piston 88. Such axial movement of the plunger 26 can be effected by withdrawing the syringe 12 from the syringe port 16 in a distal direction along the syringe longitudinal axis 15, by withdrawing the piston 88 in a proximal direction away from the plunger 26, or both. The plunger 26, together with the syringe 12, can then be completely disengaged from the piston 88. In some aspects, the piston 88 can be released from the plunger 26 by rotating the piston 88 about its longitudinal axis and retracting the piston 88 in a proximal direction to disengage the at least one retaining member 68 in a manner described herein.

Figure 6A:
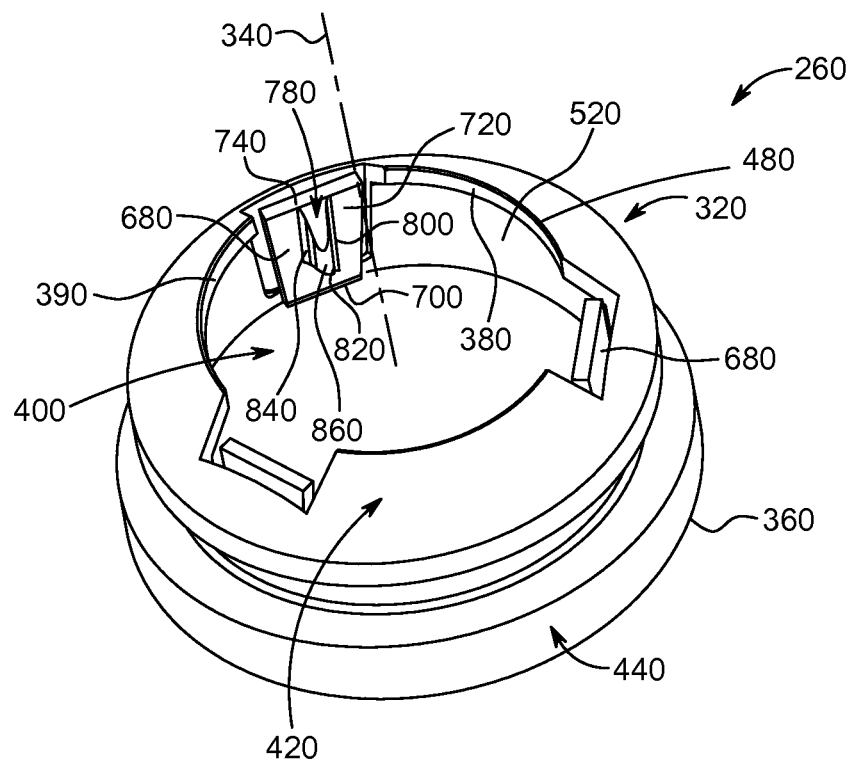
FIG. 6A is a top perspective view of a plunger according to another aspect of the present disclosure.
Figure 6B:
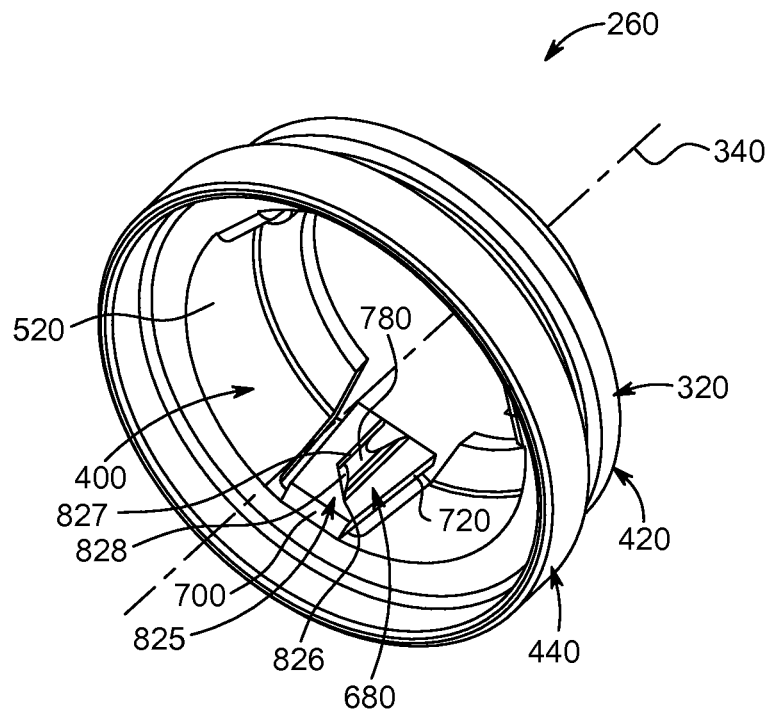
FIG. 6B is a bottom perspective view of the plunger shown in FIG. 6A.

With reference to FIGS. 6A-6B, a plunger 26 and a piston 88 are shown in accordance with another aspect of the present disclosure. The components of the plunger 26 shown in FIGS. 6A-6B are substantially similar to the components of the plunger 26 described herein with reference to FIGS. 3A-3C. Reference numerals in FIGS. 6A-6B are used to illustrate identical components of the corresponding reference numerals in FIGS. 3A-3C. As the previous discussion regarding the plunger 26 generally shown in FIGS. 3A-3C is applicable to the aspect of the present disclosure shown in FIGS. 6A-6B, only the relative differences between the plunger 26 and piston 88 generally shown in FIGS. 3A-4C and the plunger 26 and piston 88 shown in FIGS. 6A-6B are discussed hereinafter.

With reference to FIGS. 6A-6B, a plunger 260 is shown in accordance with another aspect of the present disclosure. The barrel 18 of the syringe 12 is omitted from FIGS. 6A-6B for clarity. The plunger 260 includes a plunger body 320 defining a plunger longitudinal axis 340 and having a proximal end 360, a distal end 380, and a circumferential sidewall 390 connecting the proximal end 360 and the distal end 380. The sidewall 390 may have a uniform or non-uniform thickness between the proximal end 360 and the distal end 380. The plunger body 320 may be formed from glass, metal, or a suitable medical-grade plastic.

With continued reference to FIGS. 6A-6B, the plunger body 320 has an interior cavity 400 with a conical-shaped portion 420 at the distal end 380 of the plunger body 320 and a cylindrical-shaped portion 440 at the proximal end 360 of the plunger body 320. The conical-shaped portion 420 may be monolithically formed with the cylindrical-shaped portion 440. In some aspects, the conical-shaped portion 420 may be affixed or otherwise secured to the cylindrical-shaped portion 440 of the plunger body 320 using, for example, a frictional fit and/or an adhesive, welding, or by molding. The conical-shaped portion 420 may have a truncated end 460 that has a central opening 480. In some aspects, the distal end 380 of the plunger body 320 may be enclosed. In some aspects, the plunger 260 may have a seal, such as the seal 58 shown in FIG. 2, configured for covering an outer surface of the plunger body 320.

With continued reference to FIGS. 6A-6B, the plunger 260 may have at least one resiliently deflectable retaining member 680 (hereinafter "retaining member 680") protruding from the plunger body 320 in a distal direction. In some aspects, the at least one retaining member 680 may protrude distally and radially inward from an inner surface 520 of the interior cavity 400 of the plunger body 320. The at least one retaining member 680 has a first end 700 connected to the plunger body 320 and a second end 720 radially deflectable relative to the first end 700. As described herein, the second end 720 may be radially deflectable relative to the first end 700 when the at least one retaining member 680 engages a piston of the fluid injector 10 (shown in FIG. 1). The first end 700 and the second end 720 may be spaced apart in a direction that extends substantially along a direction of the plunger longitudinal axis 340 of the plunger 260. The at least one retaining member 680 may be linearly or curvilinearly contiguous between the first end 700 and the second end 720.

In some aspects, a plurality of retaining members 680 is spaced apart radially from the plunger longitudinal axis 340 along a circumference of the inner surface 520 of the interior cavity 400. In such aspects, the retaining members 680 are separated from each other by portions of the inner surface 520 of the interior cavity 400. In aspects where more than one retaining member 680 is provided, the retaining members 680 may be evenly spaced apart from each other. In one exemplary and non-limiting aspect with three retaining members 680 having equal angular separation therebetween, such as shown in FIG. 3B, each retaining member 680 is separated by 120 degrees from the retaining members 680 adjacent on either side. In some aspects, the retaining members 680 may have unequal angular extension and/or unequal angular spacing between the retaining members 680 about the inner surface 520 of the interior cavity 400. The radial spacing of the at least one retaining member 680 relative to the plunger longitudinal axis 340 is selected to correspond to an outer circumference of the piston, as described herein.

In some aspects, one or more retaining members 680 may be parallel with the longitudinal axis 340. In other aspects, one or more retaining members 680 may be angled relative to the longitudinal axis 340. For example, one or more retaining members 680 may be angled toward the longitudinal axis 340 in a direction from the first end 700 toward the second end 720.

With continued reference to FIGS. 6A-6B, the second end 720 of the retaining member 680 has at least one catch 740. The at least one catch 740 may be a terminal surface of the second end 720 of the retaining member 680. In some aspects, the at least one catch 740 may protrude radially from the retaining member 680. For example, the at least one catch 740 may protrude radially inward toward the plunger longitudinal axis 340 of the plunger body 320, or radially outward away from the plunger longitudinal axis 340. As described herein, the at least one catch 740 is shaped to engage at least a portion of a recess on the piston to lock the at least one retaining member 680 relative to the piston. The at least one catch 740 may be formed integrally with the second end 720 of the at least one retaining member 680 or it may be affixed or otherwise secured to the second end 720 of the at least one retaining member 680 using, for example, a frictional fit and/or an adhesive, welding, or by molding. In other aspects, the at least one catch 740 may be formed on the second end 720 of the at least one retaining member 680 by etching, laser cutting, or machining.

With continued reference to FIGS. 6A-6B, the plunger 260 may have at least one first cam member 780 disposed between the first end 700 and the second end 720 of the retaining member 680. The at least one first cam member 780 is configured to interact with a piston of the fluid injector 10 (shown in FIG. 1) to radially deflect the at least one retaining member 680 upon rotation of the plunger 260 relative to the piston, as described herein. The position of the at least one first cam member 780 between the first end 700 and the second end 720 of the retaining member 680 allows for a greater radial deflection of the at least one first cam member 780 upon relative rotation between the plunger 260 and the piston 880 (shown in FIGS. 7A-7B) compared to providing the at least one first cam member 780 at the second end 720. The at least one first cam member 780 may be parallel with a surface of the retaining member 680. In some aspects, the at least one cam member 780 may be angled relative to a surface of the retaining member 680.

In some aspects, the at least one first cam member 780 protrudes radially inward toward the plunger longitudinal axis 340 of the plunger body 320. In other aspects, the at least one first cam member 780 protrudes radially outward relative to the plunger longitudinal axis 340 of the plunger body 320. The position of the at least one first cam member 780 between the first end 700 and the second end 720 of the retaining member 680 may minimize the radial protrusion of the at least one first cam member 720 while still allowing a full radial deflection of the at least one retaining member 680 upon rotation of the plunger 260 relative to the piston 880, as described herein. In some aspects, the at least one first cam member 780 may be provided on at least a portion of the at least one catch 740. A plurality of first cam members 780 may be axially spaced apart along a length of the retaining member 680 between the first end 700 and the second end 720. The at least one first cam member 780 may be formed integrally with the at least one retaining member 680 or it may be affixed or otherwise secured to the at least one retaining member 680 using, for example, a frictional fit and/or an adhesive, welding, or by molding. In other aspects, the at least one first cam member 780 may be formed on the at least one retaining member 680 by etching, laser cutting, or machining.

The at least one first cam member 780 may have at least one tooth 800 configured to engage a corresponding groove on the piston. The at least one tooth 800 on the at least one first cam member 780 is desirably shaped to correspond to the corresponding groove on the piston. Each tooth 800 may have a peak 820 leading to a groove 840 along a gear surface 860. The at least one tooth 800 on the at least one first cam member 780 may be a gear tooth having a spur gear profile or a helical gear profile. While FIGS. 6A-6B illustrate one non-limiting aspect of the at least one first cam member 780, various other shapes are also contemplated. For example, the at least one first cam member 780 of the at least one retaining member 680 may have a generally circular, square, rectangular, or any suitable polygonal shape. In each aspect, the at least first cam member 780 is configured for engaging at least a portion of the piston to cause the at least one retaining member 680 to be deflected from the piston upon rotation of the plunger 260 relative to the piston.

Figure 7A:
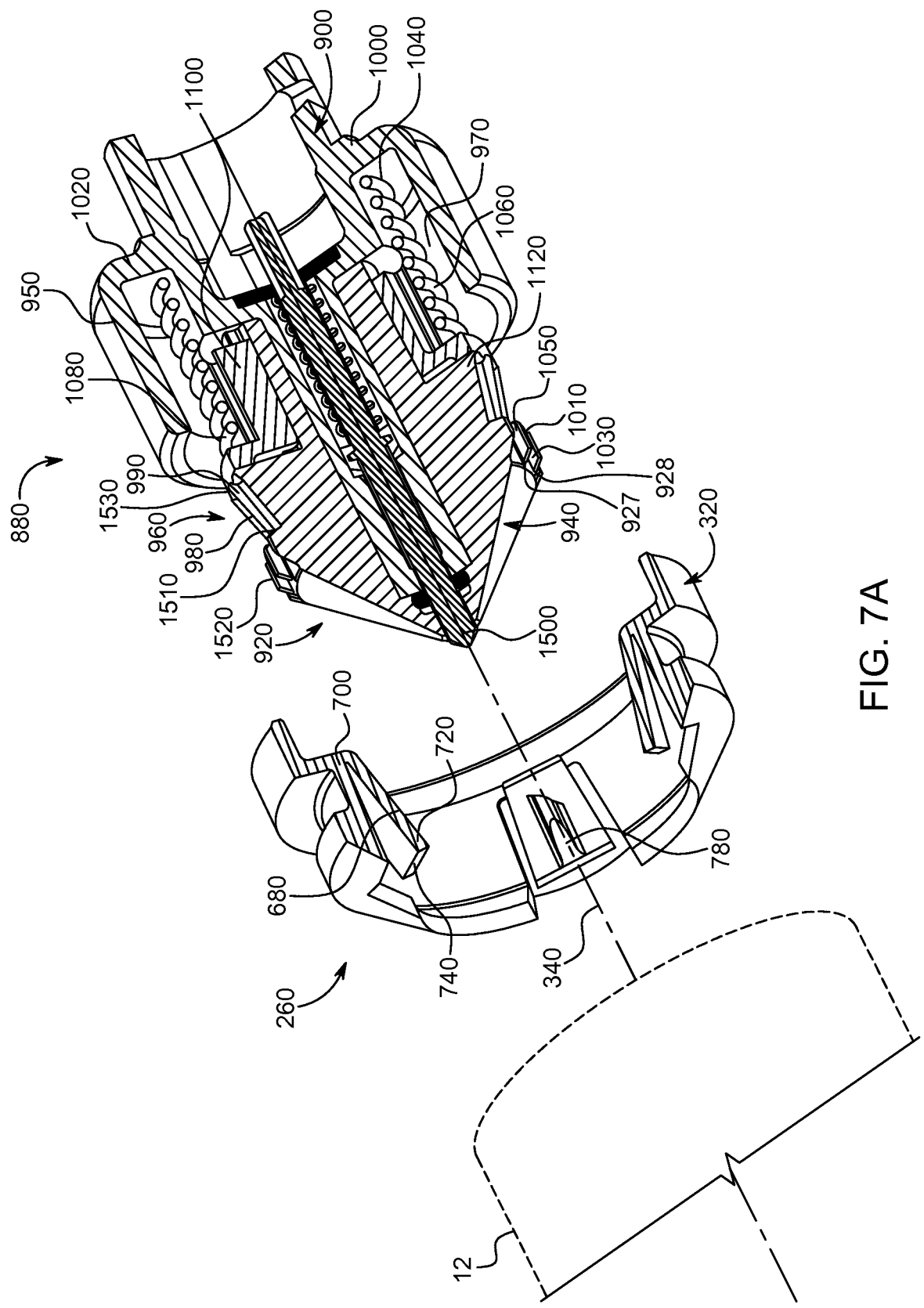
FIG. 7A is a perspective cross-sectional view of the plunger shown in FIGS. 6A-6B and a piston prior to initial engagement of the piston with the plunger.

Referring to FIG. 7A, a piston 880 is extendible and retractable from the housing 14 of the fluid injector 10 (shown in FIG. 1) via a powered means (not shown) preferably contained within housing 14. The powered means may include, for example, an electric motor, hydraulic system, or a pneumatic system, including appropriate gearing (not shown). As known in the art, the fluid injector 10 also may include a controller for controlling operation of the powered means and thereby controlling operation of the piston 880.

With continued reference to FIG. 7A, the piston 880 includes a stem 900 and a piston head 920 formed on a distal end of the stem 900. The piston 880 is construed from a relatively rigid material, such as metal or plastic that resists deformation due to repeated engagement with and disengagement from the plunger 260. The piston head 920 has a substantially cylindrical structure with a pointed distal end 940 that is configured to be received inside at least a portion of the interior cavity 400 of the plunger 260. In some aspects, a sensing member 1500, such as a spring-loaded pin connected to a sensor, may be provided. The sensing member 1500 may extend along a longitudinal axis of the piston 880 and may protrude through at least a portion of the piston head 920. The sensing member 1500 may be operative for sensing contact with a surface, such as a surface of the plunger 260, and control a movement of the piston 880 based on the sensed condition. For example, an initial contact between the sensing member 1500 and the plunger 260 may cause the pin to be retracted in a proximal direction such that it makes contact with the sensor. The sensor may be connected to the drive mechanism of the piston 880 such that, upon activation of the sensor by the pin, the sensor controls the movement of the drive mechanism. For example, the drive mechanism may be stopped or slowed from a first rate to a second, slower rate.

The proximal end 960 of the piston head 920 has a second cam member 980. In some aspects, the second cam member 980 is a gear 990 that extends around at least a portion of an outer circumference of the piston head 920. The gear 990 may have a plurality of peaks 1010 that are separated by grooves 1030 to define a gear surface 1050. The gear surface 1050 desirably corresponds to the gear surface 860 of the first cam member 780 of the plunger 260 (shown in FIG. 6A). The second cam member 980 is configured for cooperation with the first cam member 780 on the at least one retaining member 680 of the plunger 260, as described herein. The second cam member 980 desirably has a shape that, upon relative rotation between the piston 880 and the plunger 260, engages the first cam member 780 to cause the at least one retaining member 680 to be deflected from the piston head 920 such that the plunger 260 can be removed from the piston 880.

In some aspects, the second cam member 980 may be parallel with the longitudinal axis 340. In other aspects, the second cam member 980 may be angled relative to the longitudinal axis 340. For example, the second cam member 980 may be angled toward the longitudinal axis 340 at an angle corresponding to an angle of inclination of the at least one retaining member 680. In various aspects, regardless of the angular orientation of the at least one retaining member 680, the first cam member 780 is desirably parallel with the second cam member 980.

Figure 7B:
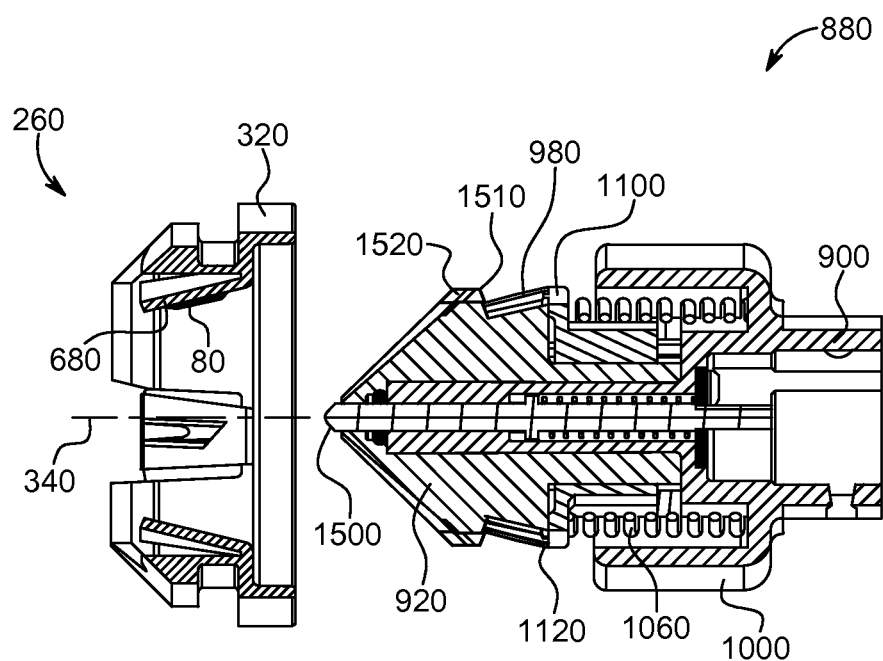
FIG. 7B is a side cross-sectional view of the plunger and piston shown in FIG. 7A.

With continued reference to FIGS. 7A-7B, the piston 880 may have a collar 950 surrounding at least a portion of the stem 900 and/or the piston head 920. The collar 950 may protrude radially outward relative to an outer radial surface of the stem 900 and the piston head 920 such that an annular space 970 is defined between the piston 880 and the collar 950. The collar 950 may have an open top end and a closed bottom end that is defined by a bottom sidewall 1000 that connects the collar 950 to the stem 900 and/or the piston head 920. The bottom sidewall 1000 defines a seat 1020 for a first end 1040 of a resiliently elastic member, such as a spring 1060, that surrounds the stem 900. In other aspects, the seat 1020 may be provided as a radial flange that protrudes from an outer surface of the stem 900. The second end 1080 of the spring 1060 engages a proximal end of a movable capture ring 1100. The capture ring 1100 has a substantially annular shape and surrounds at least a portion of an outer circumference of the stem 900. In some aspects, at least a portion of an outer diameter of the capture ring 1100 may have a same or larger outer diameter than an outer diameter of the piston head 920. The spring 1060 biases the capture ring 1100 toward a first radial lip 1120 of the piston head 920. The capture ring 1100 is movable axially between a first position, where the capture ring 1100 engages the first radial lip 1120 of the piston head 920, and a second position, where the spring 1060 is compressed and the capture ring 1100 is deflected by at least a portion of the at least one retaining member 680 toward the bottom sidewall 1000 of the collar 950. In some aspects, the capture ring 1100 may be movable between the first position and the second position when urged by contact with, for example, the first end 700 of the at least one retaining member 680. A stop member (not shown) may be provided to limit the movement of the capture ring 1100 to the second position. During disengagement of the plunger 260 from the piston 880, the capture ring 1100 urges the at least one retaining member 680 in a distal direction due to a restoring force of the spring 1060. In some aspects, the capture ring 1100 may have a grooved radial edge 1530 configured to engage the first cam member 780 of the at least one retaining member 680.

With continued reference to FIGS. 7A-7B, the piston head 920 further defines a second radial lip 1510 at a distal end of the at least one second cam member 980. When the plunger 260 is engaged with the piston 880, the second radial lip 1510 acts as a retention surface for the at least one catch 740 of the at least one retaining member 680. The piston head 920 may further have guiding grooves 1520 provided distally from the second radial lip 1510. In some aspects, the guiding grooves 1520 may have a shape that corresponds to the shape of the first cam member 780. In this manner, the tooth 800 of the first cam member 780 may be guided into the guiding groove 1520 as the plunger 260 and the piston head 920 are moved toward each other.

Having described the structure of the plunger 260 and the piston 880 in accordance with one non-limiting aspect of the present disclosure, the engagement and disengagement of the plunger 260 with and from the piston 880 will now be described with reference to FIGS. 7A-12B. The syringe 12, shown initially in phantom in FIG. 7A is omitted from the remainder of FIGS. 7B-12B for clarity.

To engage the plunger 260 with the piston 880, the syringe 12 is first inserted into the syringe port 16 of the fluid injector 10, as described herein. Once the syringe 12 is inserted into the syringe port 16, various locking mechanisms (not shown) may be used to retain the syringe 12 within the syringe port 16 to prevent detachment of the syringe 12 from the syringe port 16. Initially, the plunger 260 may be positioned at the proximal end 20 of the syringe barrel 18. In some aspects, the plunger 260 is positioned at any axial location between the proximal end 20 and the distal end 24 of the syringe barrel 18. The piston 880 may then be advanced distally toward the plunger 260 for engagement of the piston head 920 with the plunger 260. In some aspects, the piston 880 may be advanced distally toward the plunger 260 by way of the powered means operated by a controller. In other aspects, the piston 880 may be advanced distally toward the plunger 260 by manual operation.

Figure 8A:
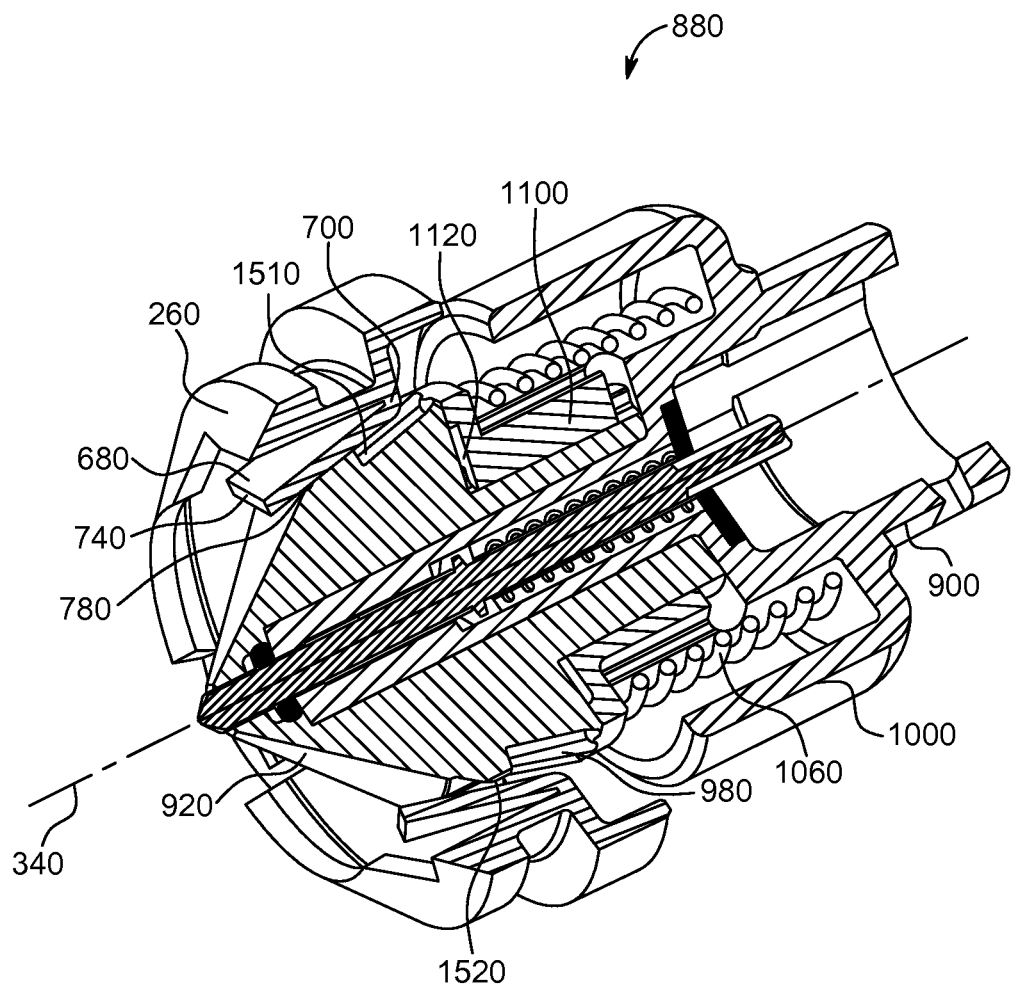
FIG. 8A is a perspective cross-sectional view of the plunger and the piston during initial engagement of the piston with the plunger.
Figure 8B:
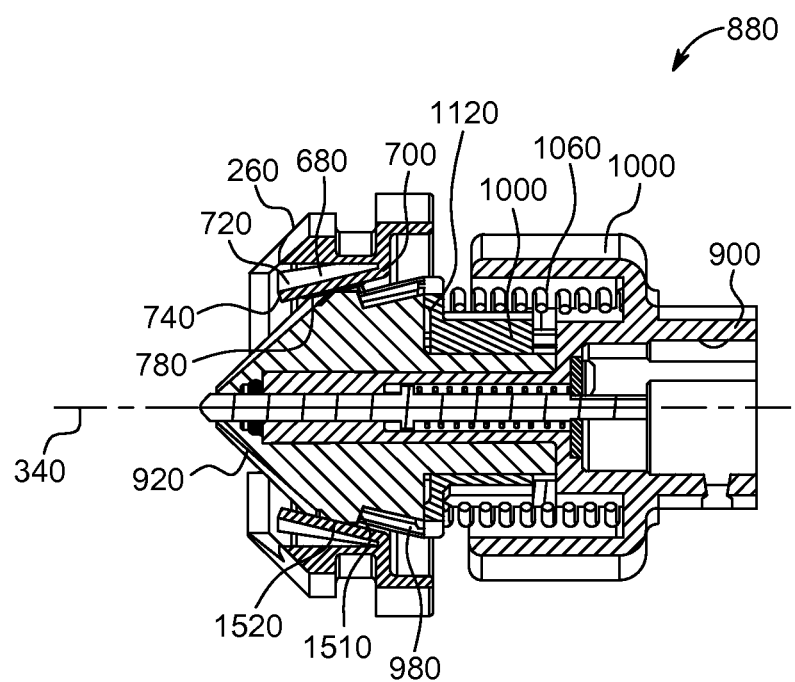
FIG. 8B is a side partial cross-sectional view of the plunger and the piston shown in FIG. 8A.

With reference to FIGS. 8A-8B, the piston 880 is advanced axially in a distal direction such that the pointed distal end 940 of the piston head 920 contacts the at least one retaining member 680 of the plunger 260. Initially, at least a portion of the piston head 920, such as the guiding grooves 1520, contacts the catch 740 of the at least one retaining member 680. Due to an angled orientation of the at least one retaining member 680 relative to the longitudinal axis, continued axial movement of the piston head 920 relative to the plunger 260 causes the at least one retaining member 680 to be deflected radially outward due to the contact between the at least one retaining member 680 and the outer surface of the piston head 920. In an aspect having a plurality of retaining members 680, each of the retaining members 680 may be deflected radially outward relative to the piston head 920.

Figure 9A:
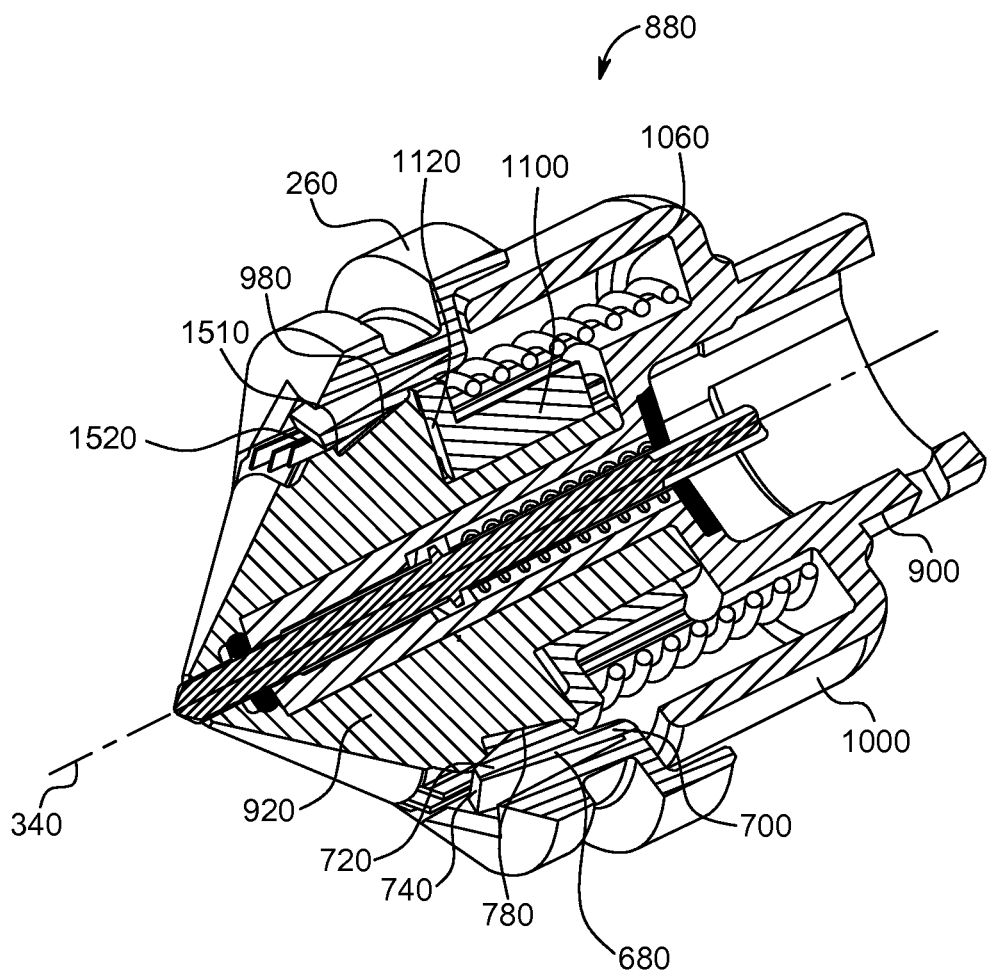
FIG. 9A is a perspective cross-sectional view of the plunger and the piston prior to full engagement of the piston with the plunger.
Figure 9B:
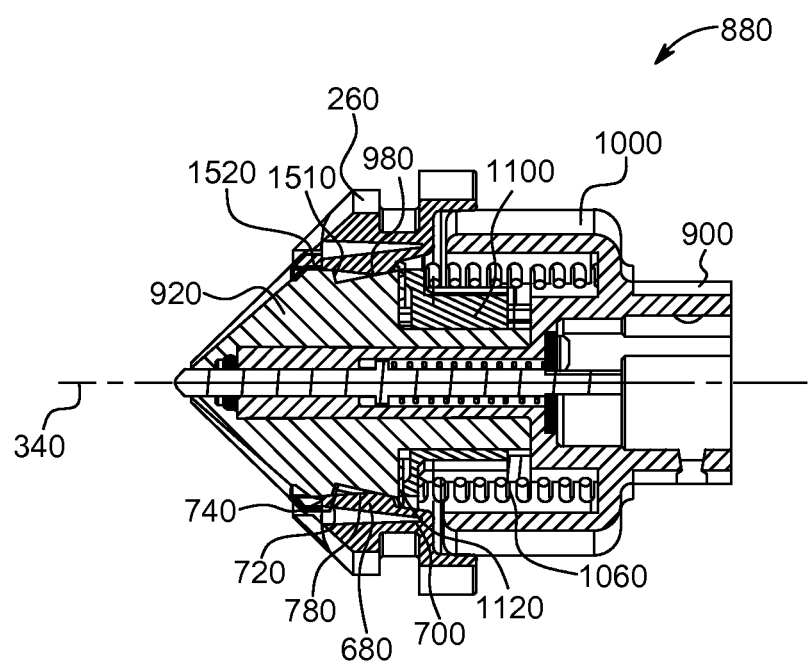
FIG. 9B is a side cross-sectional view of the plunger and piston shown in FIG. 9A.

With reference to FIGS. 9A-9B, during continued axial movement of the piston 880 in a distal direction, at least a portion of the retaining member 680 engages the distal end of the capture ring 1100. For example, the first end 720 and/or the first cam member 780 of the retaining member 680 may engage the distal end of the capture ring 1100. The contact between at least a portion of the retaining member 680 and the distal end of the capture ring 1100 urges the capture ring 1100 against the restoring force of the spring 1060 and away from the first radial lip 1120 of the piston head 920. During this movement, the first cam member 780 on the plunger 260 is brought in axial alignment with the second cam member 980 on the piston head 920.

Figure 10A:
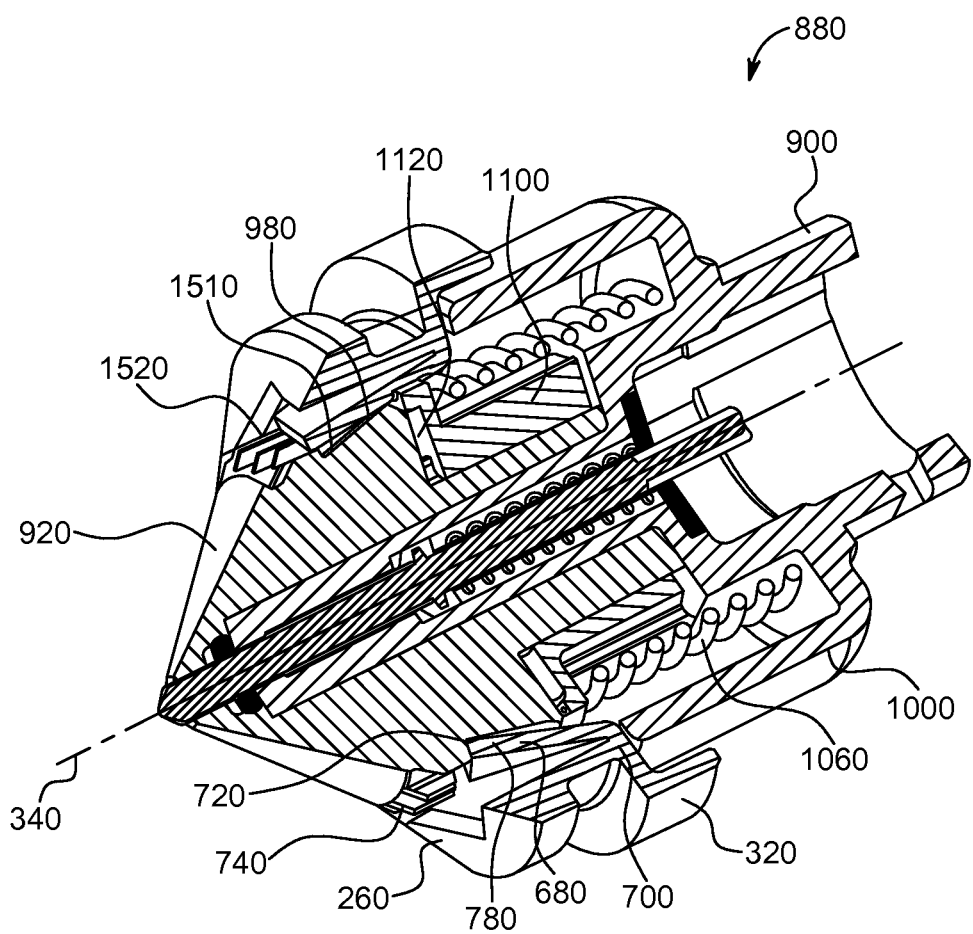
FIG. 10A is a perspective cross-sectional view of the plunger and the piston during full engagement of the piston with the plunger.
Figure 10B:
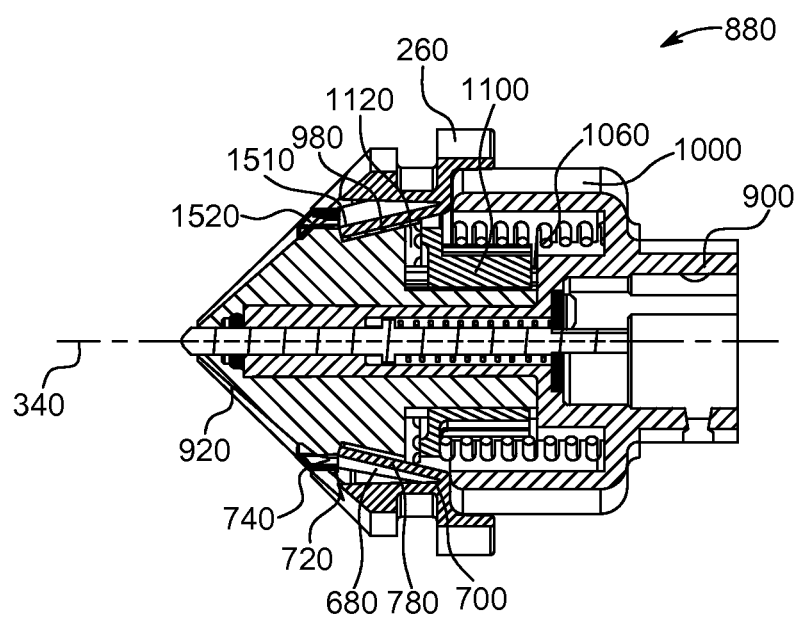
FIG. 10B is a side cross-sectional view of the plunger and piston shown in FIG. 10A.

With reference to FIGS. 10A-10B, at least a portion of the retaining member 680, such as the first end 720 and/or the first cam member 780 of the retaining member 680, urges the capture ring 1100 against the restoring force of the spring 1060. The body of the at least one retaining member 680 has an inherent restoring force built up in the material of the at least one retaining member 680 when the at least one retaining member 680 is deflected from its natural, undeflected state to a radially deflected state. Due to this inherent restoring force created within the body of the at least one retaining member 680 during a radial deflection of the at least one retaining member 680, the second end 720 and/or the catch 740 is snapped radially into the second radial lip 1510. Such radial movement of the second end 720 and/or the catch 740 also engages the first cam member 780 on the plunger 260 with the second cam member 980 on the piston head 920. Specifically, the peaks 820 of the first cam member 780 are received in the groove 103 of the second cam member 980, and the groove 840 of the first cam member 780 receives the peaks 101 of the second cam member 980. In this manner, the gear surface 860 of the first cam member 780 is engaged with the gear surface 105 of the second cam member 980. The capture ring 1100 maintains contact with at least portion of the retaining member 680 to urge the second end 720 and/or the catch 740 into contact with the second radial lip 1510. After retention of the plunger 260 on the piston head 920 by the engagement of the second end 720 and/or the catch 740 in the second radial lip 1510 of the piston head 920, the plunger 260 resists disconnection from the piston 880 upon movement of piston 880 in a distal and proximal direction relative to the syringe barrel 18. In one aspect, the second end 720 and/or the catch 740 may be designed such that the compressive forces exerted upon the second end 720 and/or the catch 740 upon movement of piston 920 in the proximal direction substantially prevents radially outward deflection (or bending) of the catch 740. For example, once the catch 740 is engaged, axial movement of the piston 880 does not introduce a bending moment which may deflect the catch 740 radially to cause the plunger 260 to be disconnected from the piston 880.

Figure 11A:
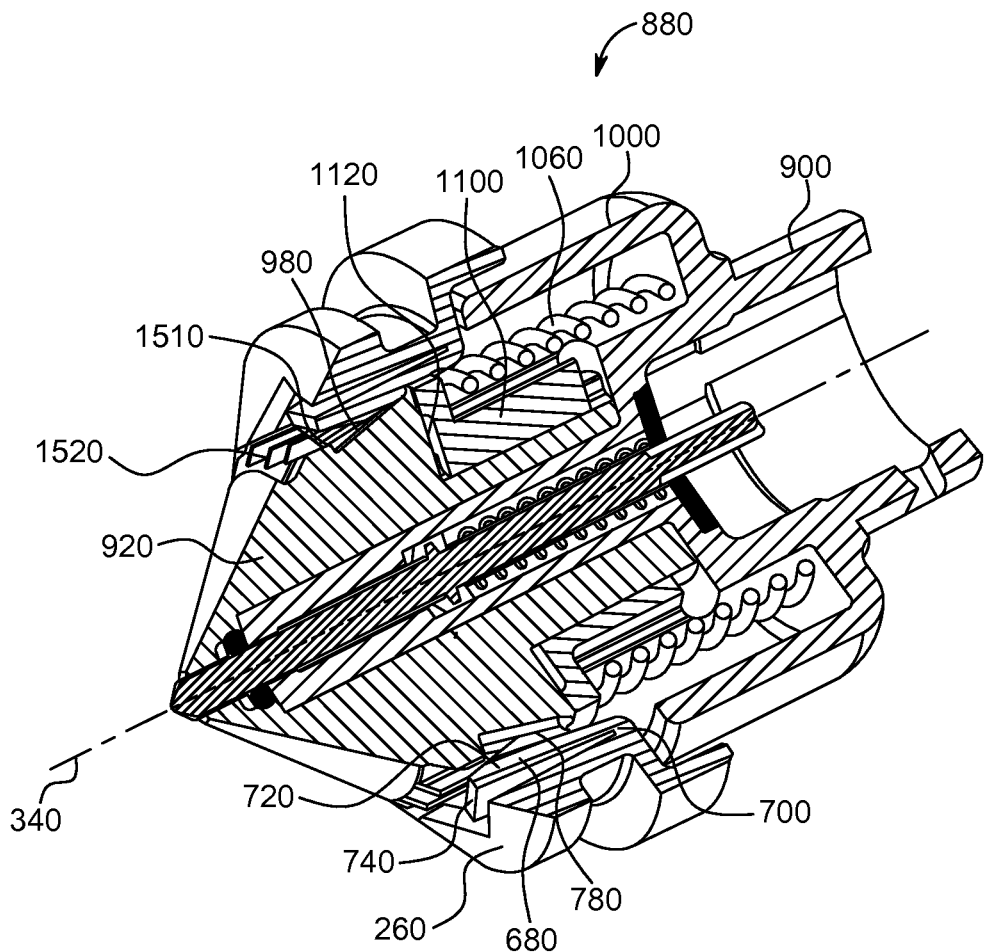
FIG. 11A is a perspective cross-sectional view of the plunger and the piston during initial disengagement as the plunger is rotated relative to the piston.
Figure 11B:
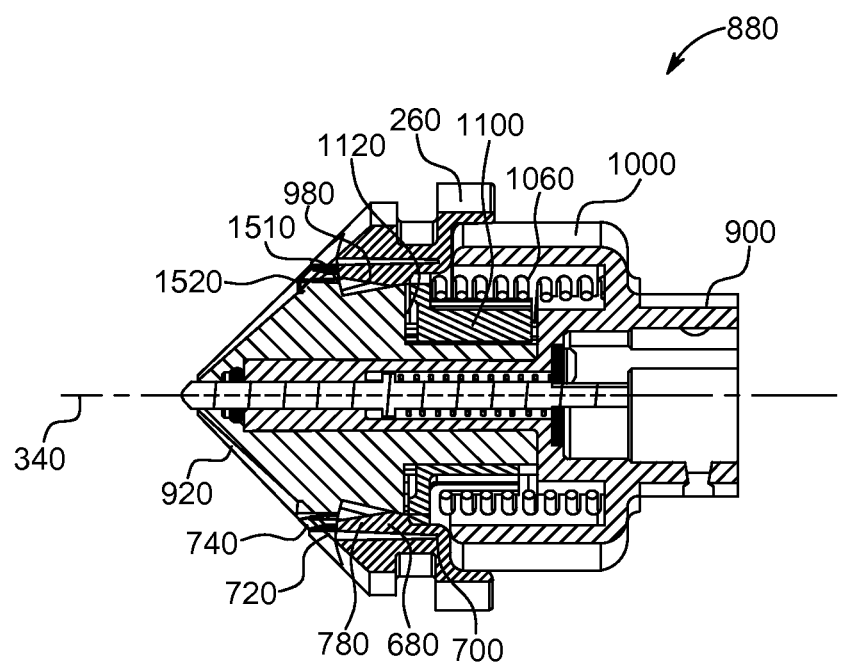
FIG. 11B is a side cross-sectional view of the plunger and piston shown in FIG. 11A.

To unlock the syringe 12 from the syringe port 16 and disengage the plunger 260 from the piston 880, the syringe 12 is rotated clockwise or counterclockwise about the syringe longitudinal axis, in a clockwise or counter-clockwise direction, relative to the syringe port 16. Because the plunger 260 is substantially free from rotation within the syringe barrel 18, the rotation of the syringe 12 also causes the plunger 260 to rotate relative to the piston 880. With reference to FIGS. 11A-11B, rotation of the plunger 260 about its longitudinal axis 340 engages the first cam member 780 on the plunger 260 with the second cam member 980 on the piston head 920. In particular, rotational movement of the plunger 260 causes the gear surface 860 of the first cam member 780 to move along the gear surface 105 of the second cam member 980 such that the peaks 820 of the first cam member 780 are moved out of the grooves 101 of the second cam member 980 and toward the peaks 101 of the second cam member 980. Such movement causes a radial reflection of the at least one retaining member 680 away from the piston head 920. The at least one retaining member 680 is at its maximum radial deflection when the peaks 820 of the first cam member 780 on the plunger 260 are positioned over or aligned with the peaks 101 of the second cam member 980 on the piston head 920.

Figure 12A:
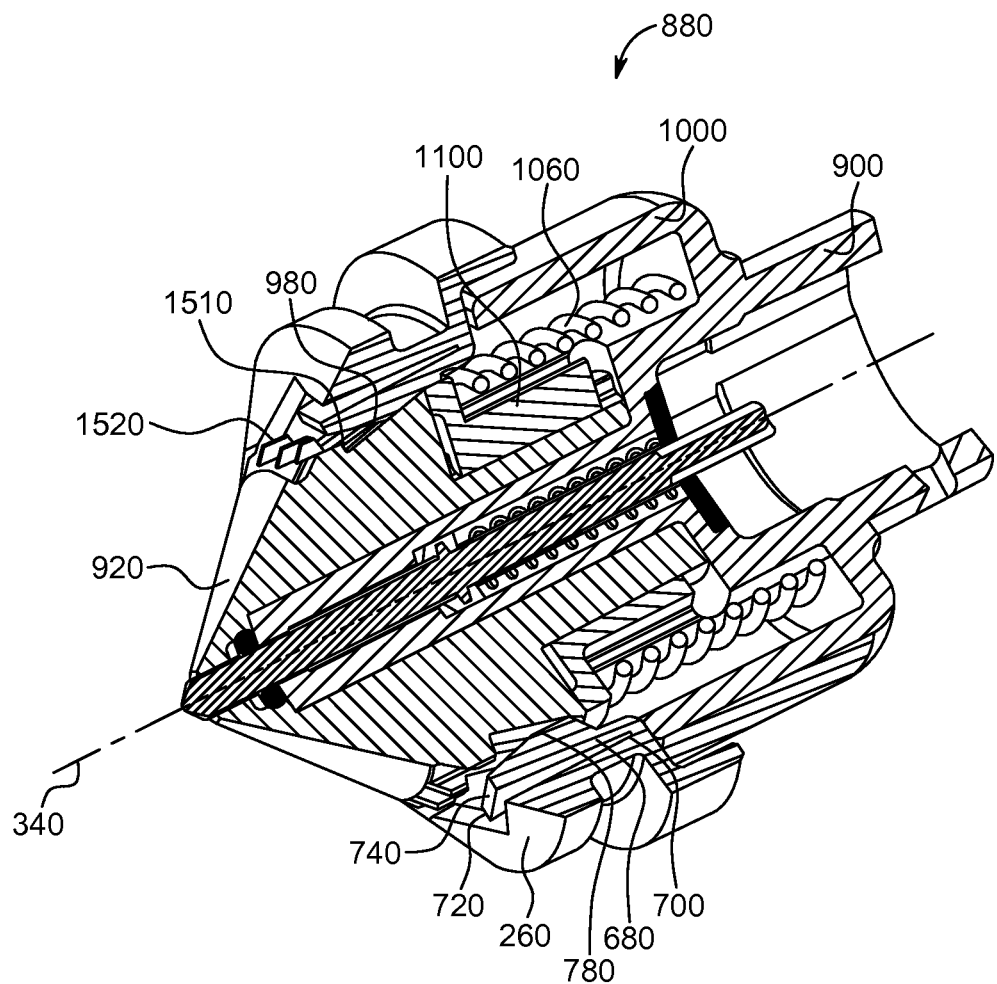
FIG. 12A is a perspective cross-sectional view of the plunger and the piston during disengagement with a locking ring of the piston in a forward position.
Figure 12B:
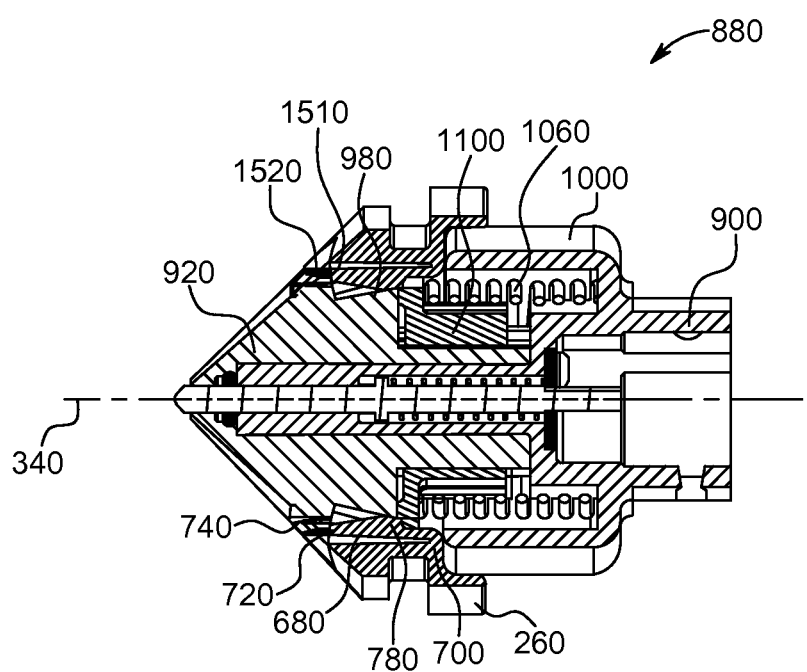
FIG. 12B is a side cross-sectional view of the plunger and the piston shown in FIG. 12A.

As the at least one retaining member 680 is deflected radially outward relative to the plunger longitudinal axis 340, the second end 720 and/or the catch 740 is moved from the second radial lip 1510 of the piston head 920. As the catch 740 moves out of its engaged position, the capture ring 1100 is advanced in the distal direction under the restoring force of the spring 1060. As shown in FIGS. 12A-12B, the distal movement of the capture ring 1100 causes the capture ring 1100 to urge the at least one retaining member 680 in the distal direction. In this position, the at least one retaining member 680 is in a deflected state that allows the plunger 260 to be moved axially relative to the piston 880. Such axial movement of the plunger 260 can be effected by withdrawing the syringe 12 from the syringe port 16 in a distal direction along the syringe longitudinal axis 15 or by withdrawing the piston 880 in a proximal direction away from the plunger 260. The plunger 260, together with the syringe 12, can then be completely disengaged from the piston 880. In some aspects, the piston 880 can be released from the plunger 260 by rotating the piston 880 about its longitudinal axis and retracting the piston 880 in a proximal direction to disengage the at least one retaining member 680 in a manner described herein.

Figure 13:
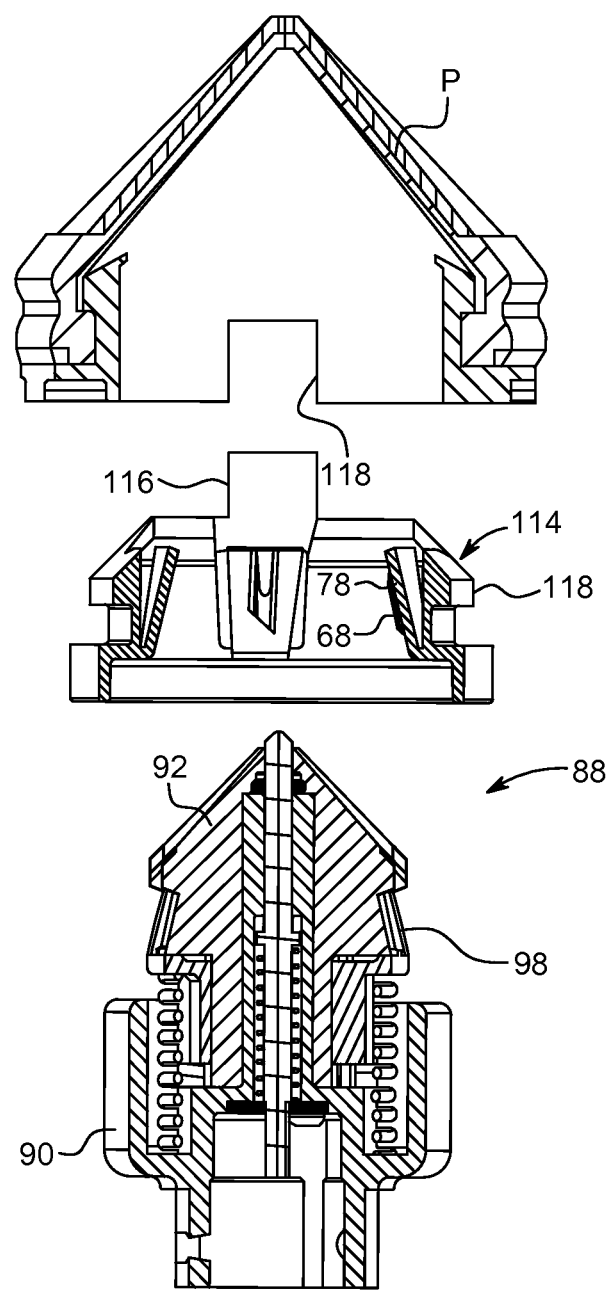
FIG. 13 is a side cross-sectional view of a first adapter configured for connecting a non-compatible plunger with a piston.

With reference to FIG. 13, a first adapter 114 may connect with a plunger P not having the at least one retaining member 68 described herein for removably engaging with the piston 88 of an injector having the piston head 92 with the second cam member 98 in accordance with one of the aspects described herein. In various aspects, the first adapter 114 may be connect to the plunger P for subsequent engagement with the piston 88. For example, the first adapter 114 may be connected to the non-compatible plunger P releasably or permanently. Such a first adapter 114 may have a connection interface having at least one retaining member 68 with the first cam member 78 in accordance with various aspects described herein. The first adapter 114 may releasably connect with an injector having the piston 88 described herein. The first adapter 114 and the plunger P may be connected prior to connecting to the piston 88, or the first adapter 114 may be connected to the piston 88 before the plunger P is connected to the first adapter 114. The first adapter 114 and plunger P may be removed from the piston 88 after use, with the first adapter 114 being disposed of with the plunger P, or being removed from the used plunger P and saved for subsequent use with a different plunger P.

In one aspect, a first portion 116 of the first adapter 114 may permanently or releasably receive the plunger P, which is not compatible for use with the piston 88 described herein. The first adapter 114 allows a connection mechanism 118 of the non-compatible plunger P to engage and be retained on the first adapter 114. In some aspects, the first adapter 114 may have a separate mechanism for engaging and disengaging the plunger P while the first adapter 114 remains connected to the piston 88. A second portion 120 of the first adapter 114 may have at least one retaining member 68 in accordance with aspects described herein. In some aspects, the at least one retaining member 68 may have one the first cam member 78, 780 described herein with reference to FIGS. 3A-3B and 6A-12B. The second portion 120 of the first adapter 114 may releasably connect to an injector having the piston 88 with the piston head 92 described herein. In this manner, various non-compatible plungers P may be used. The first adapter 114 may releasably, permanently, or semi-permanently connect to an injector having the piston 88 with the piston head 92 described herein and allowing plungers P having alternate connection mechanisms to be used with the injector.

Figure 14:
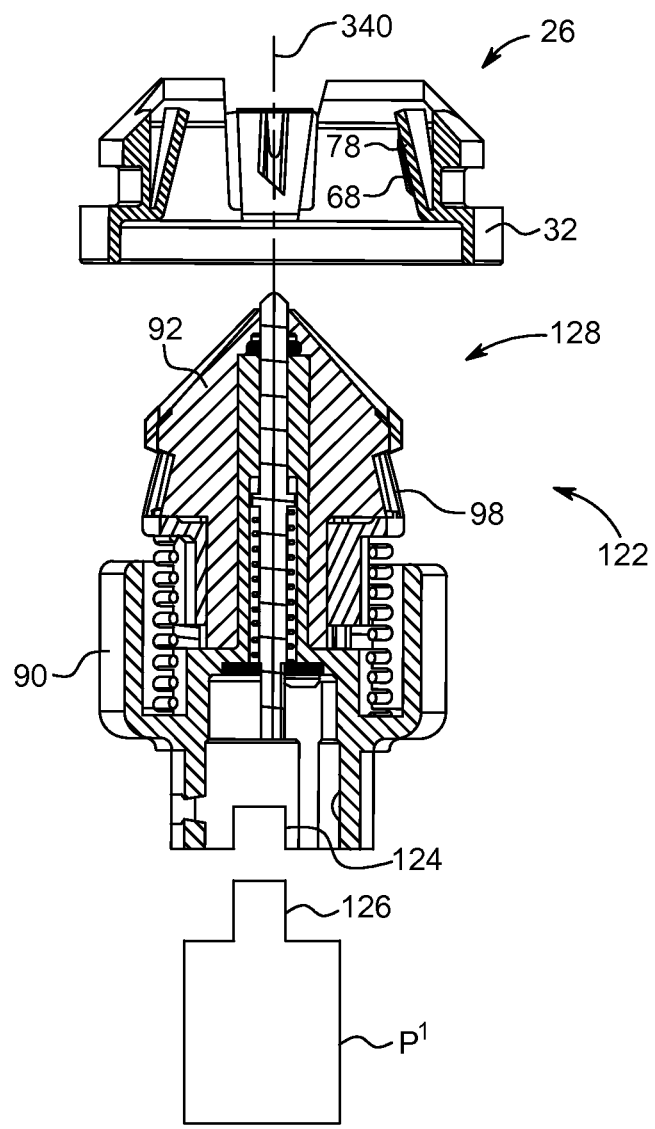
FIG. 14 is a side cross-sectional view of a second adapter configured for connecting a plunger with a non-compatible piston.

With reference to FIG. 14, a second adapter 122 may connect the plunger 26 with an injector that does not have the piston 88 with the piston head 92 described herein. In various aspects, the second adapter 122 may connect to the plunger 26 for subsequent engagement with a non-compatible piston P'. For example, the second adapter 122 may be connected to the plunger 26 releasably or permanently. Such a second adapter 122 may have a connection interface having features of the piston head 92 in accordance with various aspects described herein. The second adapter 122 and the plunger 26 may be connected prior to connecting to the piston P', or the second adapter 122 may be connected to the piston P' before the plunger 26 is connected to the second adapter 122. The second adapter 122 and plunger 26 may be removed from the piston P' after use, with the second adapter 122 being disposed of with the plunger 26, or being removed from the used plunger 26 and saved for subsequent use with a different plunger 26.

In one aspect, a first portion 124 of the second adapter 122 may permanently or releasably engaging the plunger 26, which is not compatible for use with the piston P'. The second adapter 122 allows a connection mechanism 126 of the non-compatible piston P' to engage the second adapter 122. A second portion 128 of the second adapter 122 may have features of the piston head 92 in accordance with aspects described herein. In some aspects, the second portion 128 may have the second cam member 98, 980 described herein with reference to FIGS. 5A and 17A. The second portion 128 of the second adapter 122 may releasably connect to the plunger 26 described herein. In this manner, the plunger 26 may be connected to various non-compatible injectors using the second adapter 122.

Referring to FIG. 15A-15G, a piston 88 and a plunger 26 are shown in accordance with another aspect. The piston 88 is configured to interact with the plunger 26 (shown in FIG. 15C) to releasably lock the plunger 26 such that the plunger 26 can be driven reciprocally within the barrel of the syringe 12 (shown in FIG. 2). The piston 88 is extendible and retractable from the housing 14 of the fluid injector 10 (shown in FIG. 1) via a powered means (not shown) preferably contained within housing 14. The powered means may include, for example, an electric motor, hydraulic system, or a pneumatic system, including appropriate gearing (not shown). As known in the art, the fluid injector 10 also may include a controller for controlling operation of the powered means and thereby controlling operation of the piston 88.

Figure 15A:
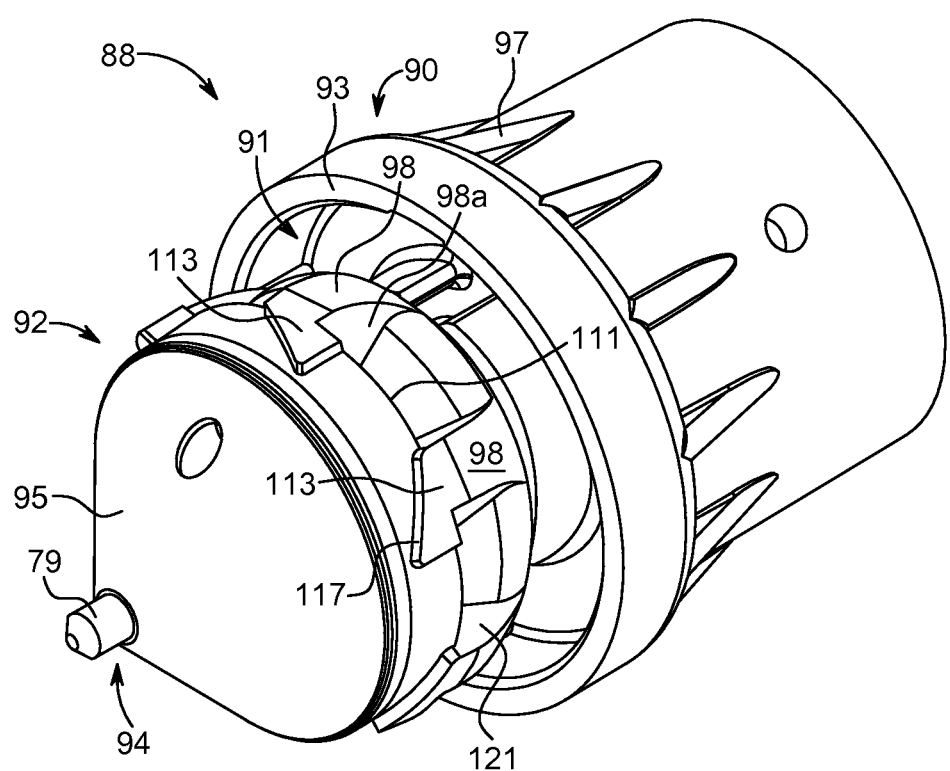
FIG. 15A is a front perspective view of a piston in accordance with another aspect.

With continued reference to FIG. 15A, the piston 88 includes a stem 90 and a piston head 92 formed on a distal end of the stem 90. At least a portion of the piston head 92 extends distally to the stem 90. The piston head 92 is construed from a rigid material, such as metal or plastic that resists deformation. The stem 90 may have a cavity 91 for collecting any fluid that may drip from the syringe and an annular collar 93 that surrounds the cavity 91. One or more buttresses 97 connect the annular collar 93 to the stem 90. The piston head 92 has a substantially cylindrical structure with a pointed distal end 94 with a cap 95 that is shaped to be received inside at least a portion of the interior cavity 40 (shown in FIG. 3A) of the plunger 26. In some aspects, a sensing member 79, such as a pin connected to a sensor, may be provided. The sensing member 79 may extend along a longitudinal axis of the piston 88 and may protrude through at least a portion of the piston head 92, such as through at least a portion of the cap 95. The sensing member 79 may be operative for sensing contact with a surface, such as a surface of the plunger 26, and control a movement of the piston 88 based on the sensed condition. For example, an initial contact between the sensing member 79 and the plunger 26 may cause the pin to be retracted in a proximal direction such that it makes contact with the sensor. The sensing member 79 may be biased in an extended position by a resilient element 81 (shown in FIG. 15E), such as a spring. The sensor may be connected to the control mechanism which controls the drive mechanism of the piston 88 such that, upon activation of the sensor by the pin, the controller controls the movement of the drive mechanism. For example, the drive mechanism may be stopped or slowed from a first rate to a second, slower rate.

Figure 15B:
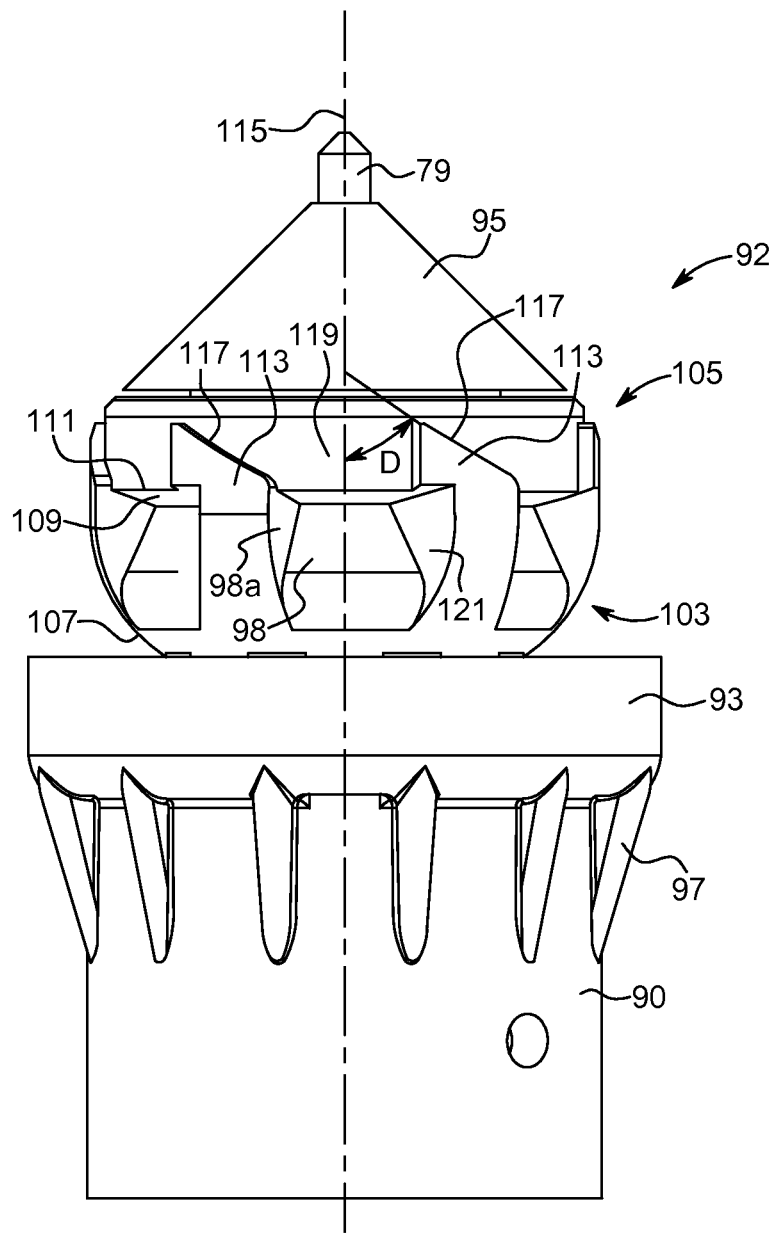
FIG. 15B is an exploded perspective view of the piston shown in FIG. 15A.

With reference to FIG. 15B, the piston head 92 has a proximal portion 103 connected to a distal portion 105. Terminal ends of the proximal and distal portions 103, 105 may have a radiused edge 107. At least a portion of the proximal portion 103 has a smaller outer diameter compared to an outer diameter of the distal portion 105 such that a radial lip 109 is formed at a transition between the proximal portion 103 and the distal portion 105. The radial lip 109 may be continuous or discontinuous around a circumference of the piston head 92. In some aspects, the radial lip 109 defines a locking ledge 111 for engaging the catch 74 of the at least one retaining member 68 when the plunger 26 is fully seated on the piston head 92.

With continued reference to FIG. 15B, the piston head 92 may have at least one second alignment member 113 protruding radially outward from an outer surface of the piston head 92. The at least second alignment member 113 is shaped and/or configured for interacting with the first alignment member 71 of the plunger 26 the facilitating alignment of the piston 88 with the plunger 26 in order to allow for a releasable locking connection of the plunger 26 with the piston 88. In some aspects, at least a portion of the at least second alignment member 113 may extend in a direction that is angled relative to the direction of a piston longitudinal axis 115. For example, at least second alignment member 113 may have a guiding surface 117 that is angled at an angle D relative to the piston longitudinal axis 115. The guiding surface 117 is desirably angled such that the piston head 92 may rotate around the piston stem 90 when the proximal alignment surface 77a of the first alignment member 71 contacts the guiding surface 117 of the second alignment member 113.

In some aspects, a plurality of second alignment members 113 may spaced apart radially relative to the piston longitudinal axis 115 along an outer circumference of the piston head 92. In some aspects, the number of second alignment members 113 may be equal to a total number of retaining members 68 and first alignment members 71 on the plunger 26. The second alignment members 113 are spaced apart circumferentially such that a retaining member 68 or a first alignment member 71 may be received between adjacent second alignment members 113. The second alignment members 113 may be separated from each other by portions of an outer surface of the proximal portion 103 and/or the distal portion 105 of the piston head 92. In some aspects, such as shown in FIG. 20, at least a portion of the second alignment members 113, such as a lower or proximal end of the second alignment members 113 may be connected by a continuous lip 123 that extends continuously around an outer circumference of the piston head 92 at a radial position that may be flush, radially recessed, or radially protruding relative to an outer surface of the second alignment members 113. In aspects where two or more second alignment members 113 are provided, the second alignment members 113 may be evenly spaced apart from each other. In one exemplary and non-limiting aspect with second alignment members 113 having equal angular separation therebetween, such as shown in FIG. 4A, each second alignment member 113 is separated by 60 degrees from the second alignment members 113 adjacent on either side. In some aspects, the second alignment members 113 may have unequal angular extension and/or unequal angular spacing between the second alignment members 113 about the outer surface of the proximal portion 103 and/or the distal portion 105 of the piston head 92. The radial spacing of the at least one second alignment members 113 relative to the piston longitudinal axis 115 is selected to correspond to an inner shape of the plunger 26 to allow the retaining members 68 and the first alignment members 71 to be received between adjacent second alignment members 113, as described herein.

With continued reference to FIG. 15B, each of the guiding surfaces 117 of the second alignment members 113 define a travel path for guiding the movement of the proximal alignment surface 77a of the first alignment member 71 in and out of a recess 119 defined between adjacent second alignment members 113. The guiding surfaces 117 may be inclined or angled radially and axially relative to the piston longitudinal axis 115 to guide the movement of the proximal alignment surfaces 77a. The guiding surfaces 117 aid in self-orienting the piston head 92 as the plunger 26 is brought into contact with the piston 88 by guiding the one or more proximal alignment surfaces 77a on the plunger 26 into the corresponding recess 119 on the piston head 92. In this manner, a piston 88 whose piston longitudinal axis 115 is rotationally misaligned with the plunger longitudinal axis 34 and the one or more first alignment member 71 which are initially misaligned relative to the corresponding one or more second alignment members 77a in a rotational direction are brought in alignment axially and rotationally such that the one or more first alignment members 71 are received within the recess 119 between adjacent second alignment members 113. The one or more second alignment members 113 may have a bottom surface 121 that is angled relative to the direction of a piston longitudinal axis 115.

The piston head 92 further has a second cam member 98. In some aspects, the second cam member 121 cooperates with the first cam member 78 on the at least one retaining member 68 of the plunger 26, as described herein. The second cam member 121 desirably has a shape that, upon relative rotation between the piston 88 and the plunger 26, engages the first cam member 78 to cause the at least one retaining member 68 to be deflected from the piston head 92 such that the plunger 26 can be removed from the piston 88. In some aspects, the second cam member 121 may be formed on or intersect with the second alignment member 113 on the piston head 92. The second cam member 98 may be a surface that is aligned with a direction of the piston longitudinal axis 115. The second cam member 98 may have a chamfered portion, not shown, to facilitate passing of the first cam member 78 after the retaining member 68 is deflected sufficiently to allow the retaining member to be released.

Figure 15C:
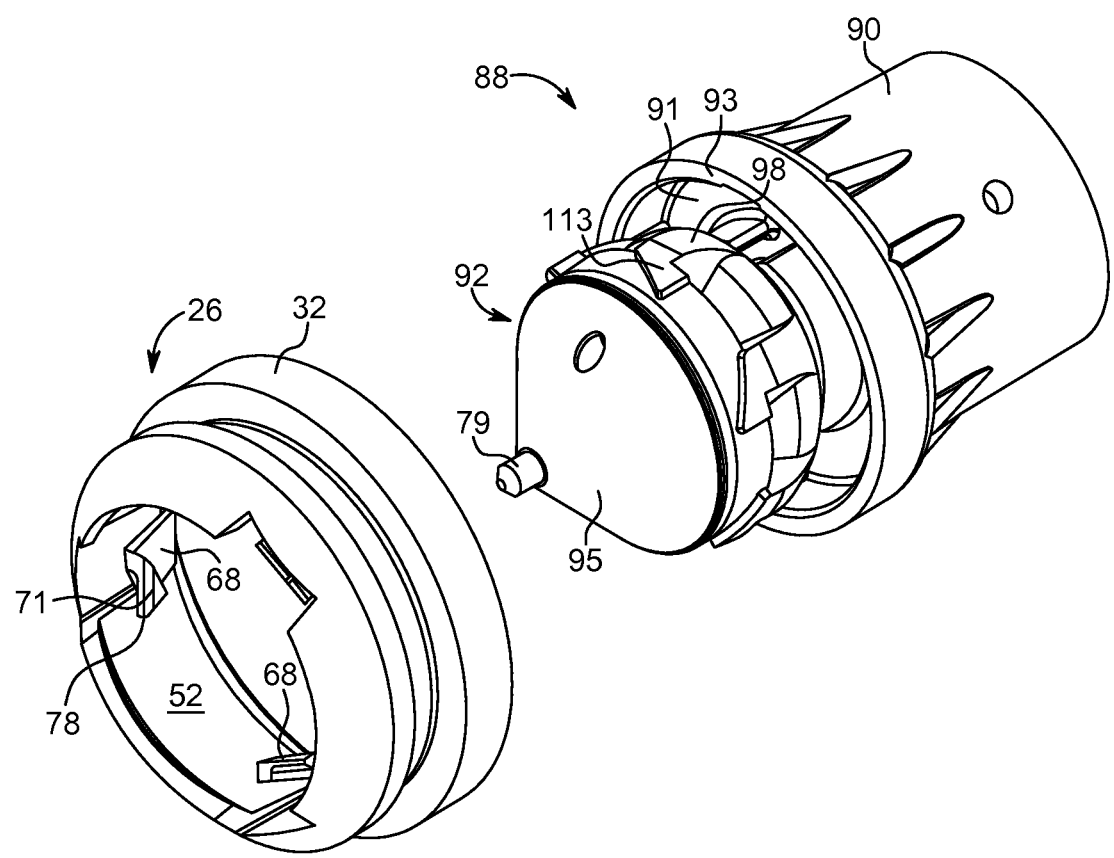
FIG. 15C is a side view of the piston head shown in FIG. 15A.
Figure 15D:
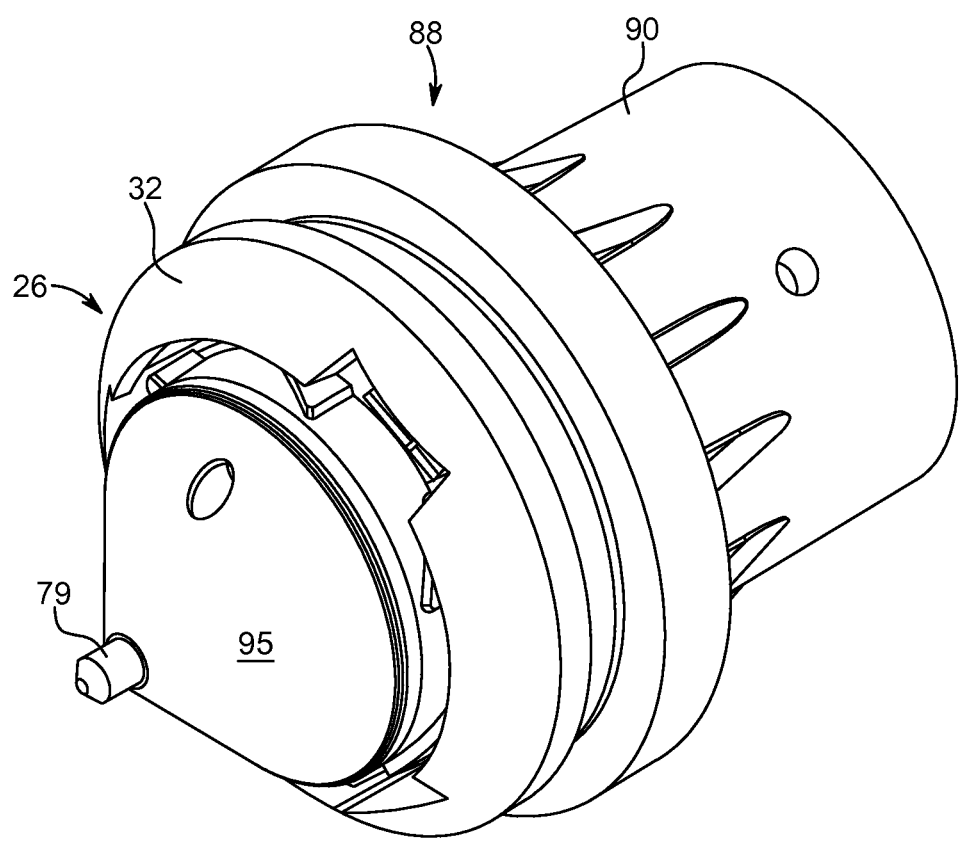
FIG. 15D is a front perspective of the piston and plunger shown in FIG. 15C with the plunger assembled on the piston.
Figure 15E:
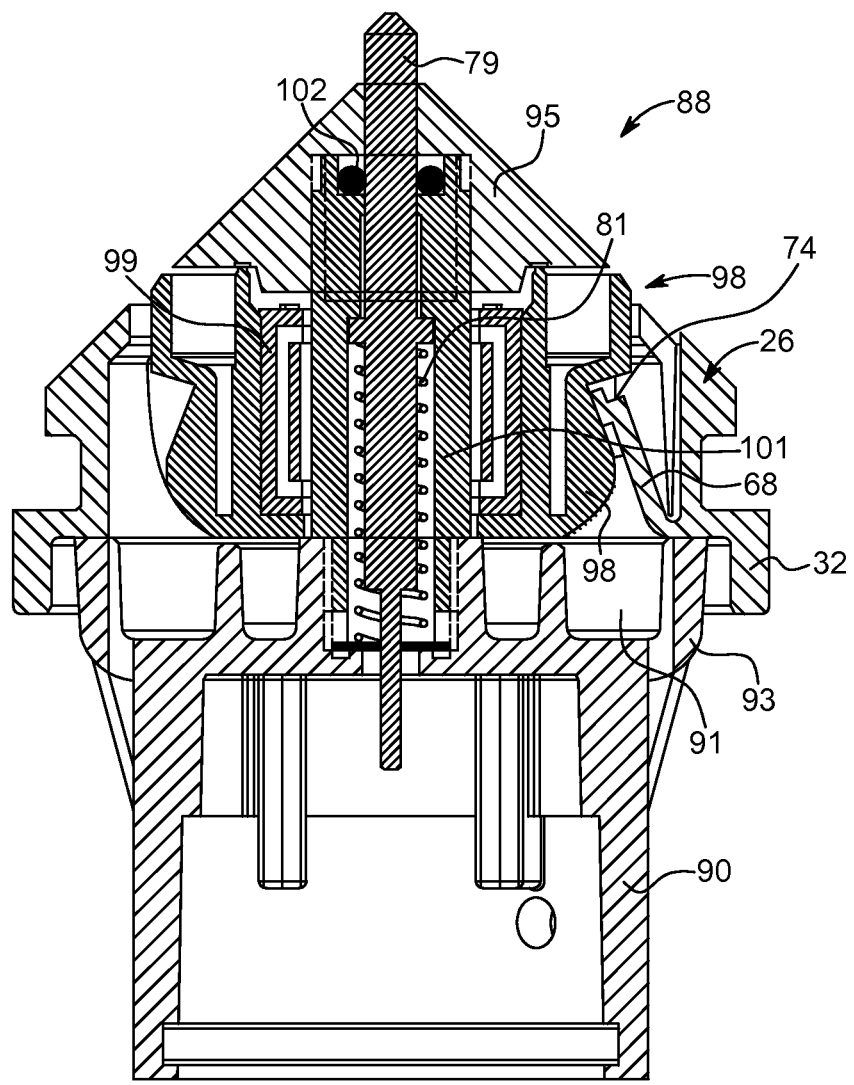
FIG. 15E is a side cross-sectional view of the plunger and the piston shown in FIG. 15D.

With reference to FIG. 15C, the piston 88 is configured to interact with the plunger 26 to releasably lock with plunger 26, such as shown in FIG. 15D. By locking the piston 88 to the plunger 26, the plunger 26 can be driven reciprocally within the barrel of the syringe 12 (shown in FIG. 2). The second cam member 121 on the piston 88 cooperates with the first cam member 78 on the at least one retaining member 68 of the plunger 26, to releasably lock the plunger 26 to the piston 88.

Figure 15F:
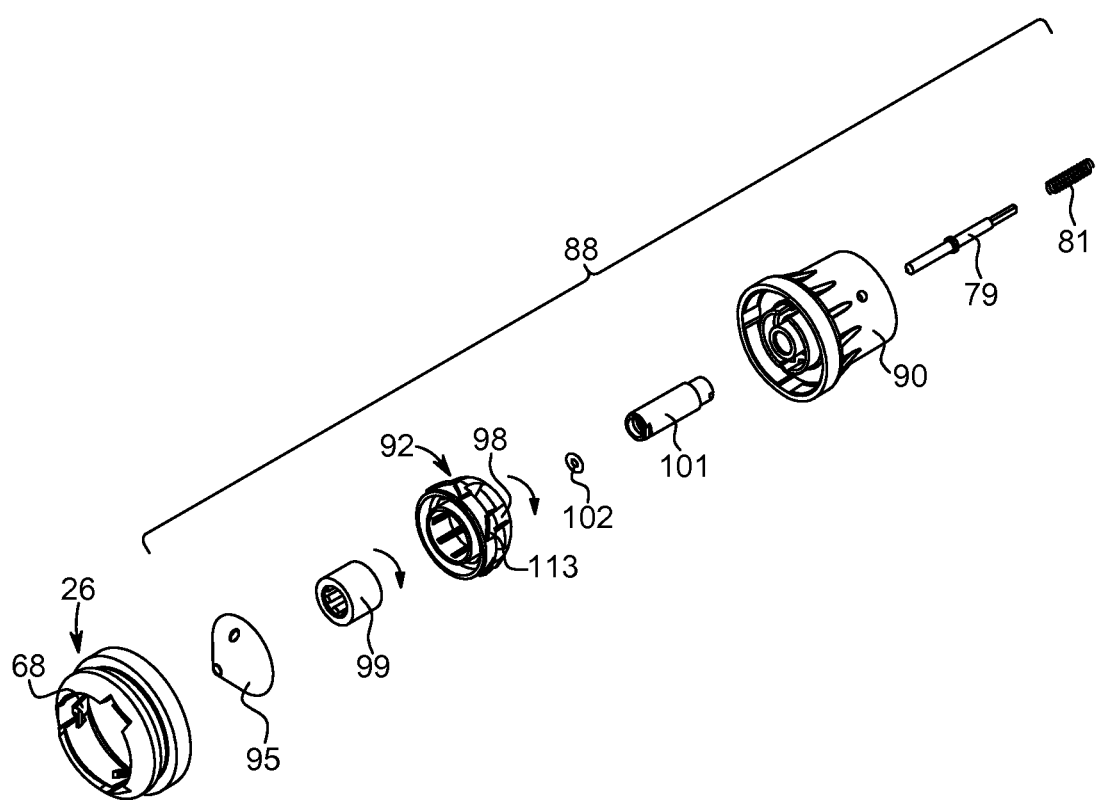
FIG. 15F is an exploded perspective view of the piston shown in FIG. 15A.

With reference to FIG. 15F, the piston head 92 may be rotatable relative to the stem 90. In some aspects, the piston head 92 may be rotatable in one direction only, such as a clockwise or a counterclockwise direction, relative to the stem 90. A one-way rotation mechanism 99, such as a one-way clutch mechanism shown in FIG. 15F, may be provided to allow the rotation of the piston head 92 in a first direction only, such as the clockwise or the counterclockwise direction. The one-way rotation mechanism 99 may be rotatable around a central shaft 101 having a seal 102, such as an O-ring seal. In some aspects, the one-way rotation mechanism 99 may have a stop that prevents rotation of the piston head 92 in a second direction opposite the first direction, such as the counterclockwise or the clockwise direction, respectively. In other aspects, the one-way rotation mechanism 99 may be provided on at least a portion of the plunger 26.

Figure 15G:
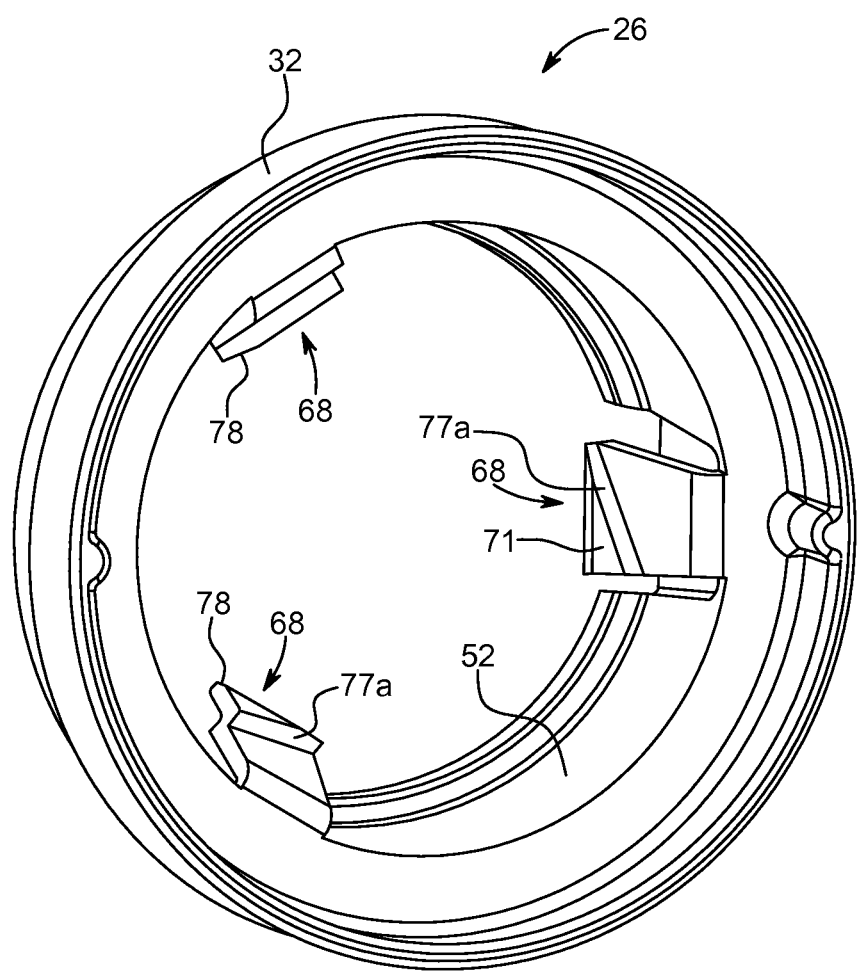
FIG. 15G is a bottom perspective view of a plunger in accordance with another aspect.

With reference to FIG. 15G, the plunger 32 the at least one first alignment member 71 may be provided directly on one or more of the retaining members 68. In such aspects, at least one retaining member 68 may have a proximal alignment surface 77a and a distal alignment surface 77b provided directly on the body of the at least one retaining member 68. The first cam member 78 may be also provided directly on the retaining member 68, or it may be provided on a portion of the plunger body 32 such that activation of the cam member 78 causes a corresponding activation of the retaining member 68, as described herein.

Figure 16:
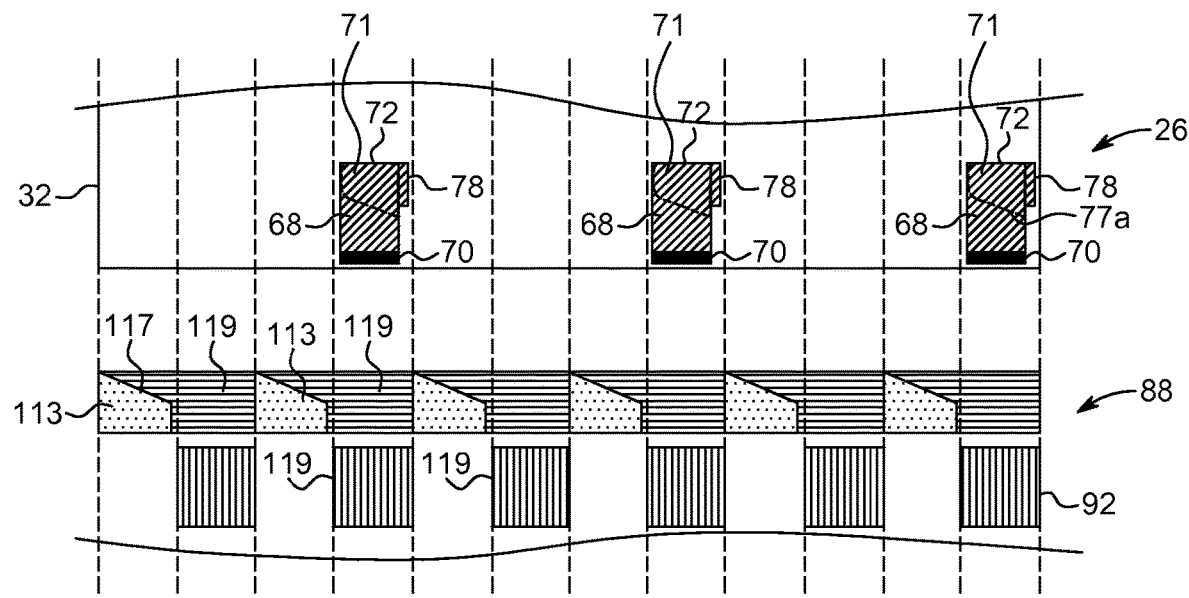
FIG. 16 is a cylindrical plan projection view of the piston and the plunger shown in FIG. 15C.

With reference to FIG. 16, a cylindrical plan projection view of the piston 88 and the plunger 26 is shown. If the piston 88 is rotationally misaligned relative to the plunger 26 such that the first alignment members 71 (shown in FIG. 3A) on the plunger 26 are not in rotational alignment to be received within the recesses 119 (shown in FIG. 4C) on the plunger head 92, the proximal alignment surface 77a (shown as a dotted line) of the first alignment member 71 on the plunger 26 contacts the guiding surface 117 of the second alignment member 113 on the piston head 92. Engagement of the proximal alignment surface 77a with the guiding surface 117 causes the piston head 92 to automatically rotate in a free rotation direction of the one-way rotation mechanism 99. Such rotation of the piston head 92 aligns the first alignment members 71 and the retaining members 68 to be received within the recesses 119 between adjacent second alignment members 113. In this manner, the piston 88 self-orients itself relative to the plunger 26 such that the plunger 26 may be releasably locked with the piston 88. If the piston 88 is rotationally aligned relative to the plunger 26, such as shown in FIG. 16, the first alignment members 71 and the retaining members 68 on the plunger 26 can be received within the recesses 119 between adjacent second alignment members 113 without rotation of the piston head 92.

Figure 17:
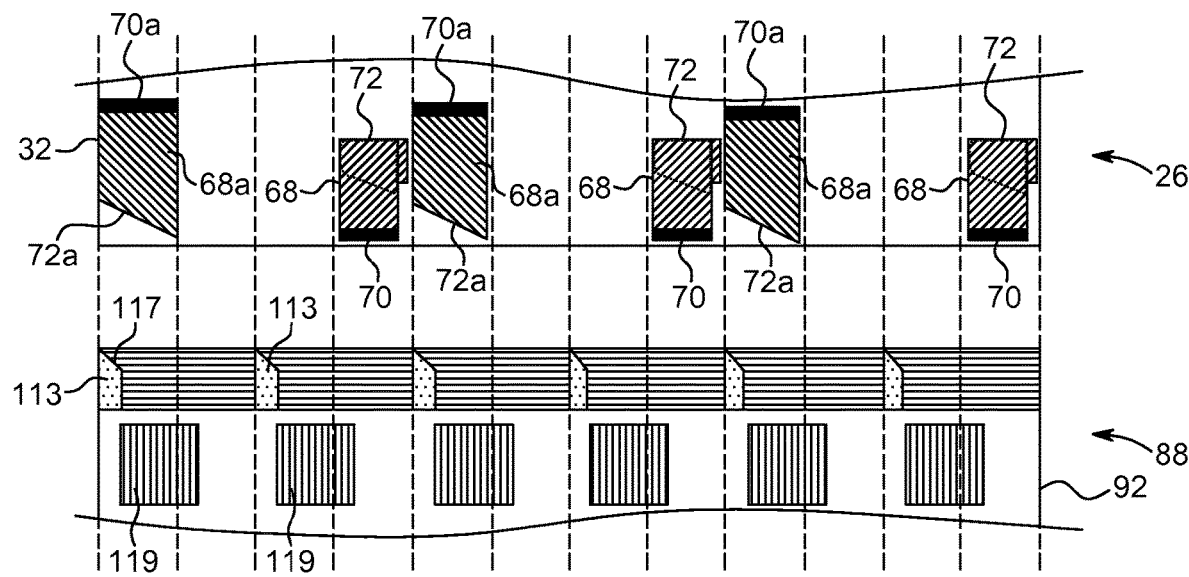
FIG. 17 is a cylindrical plan projection view of a piston and a plunger in accordance with another aspect.
Figure 18:
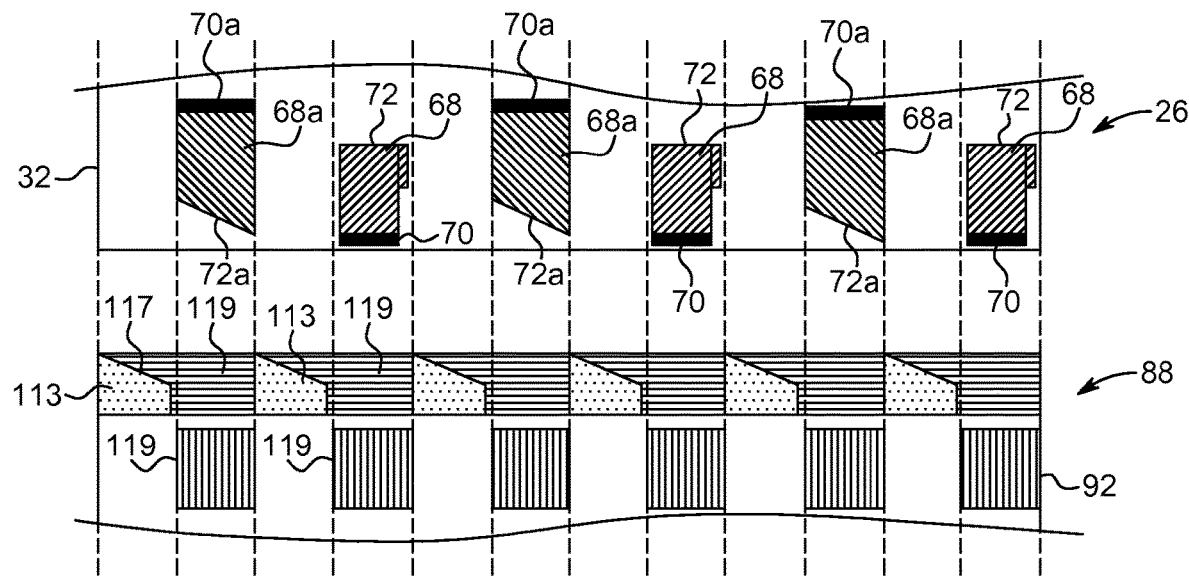
FIG. 18 is a cylindrical plan projection view of a piston and a plunger in accordance with another aspect.
Figure 19:
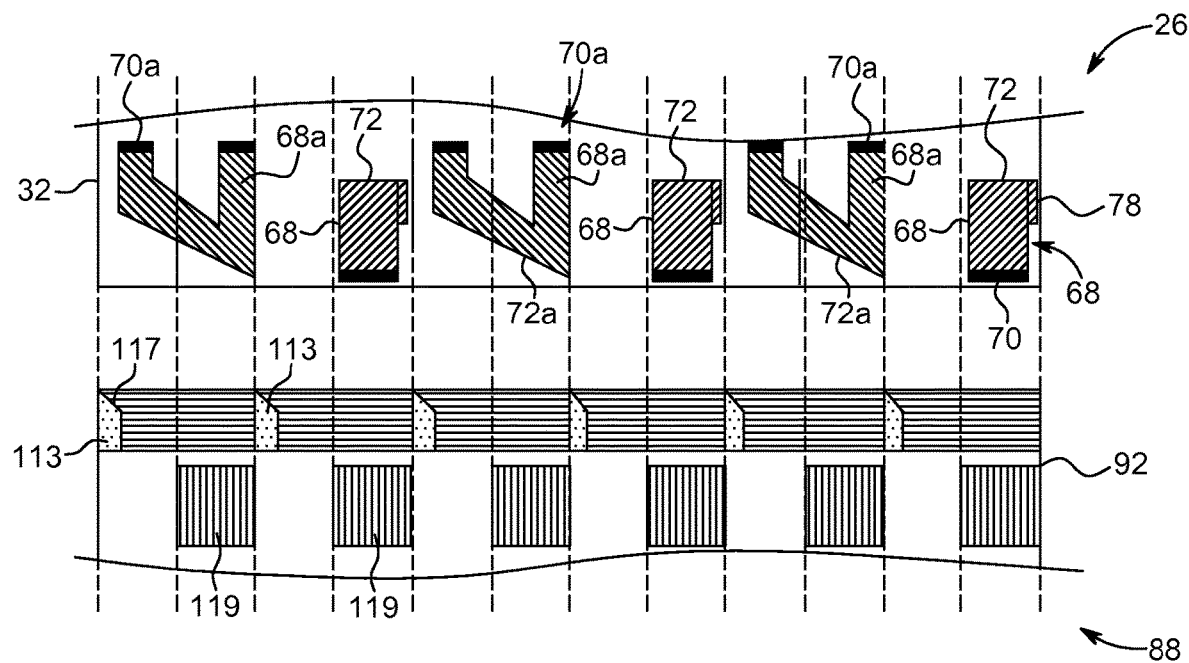
FIG. 19 is a cylindrical plan projection view of a piston and a plunger in accordance with another aspect.
Figure 20A:
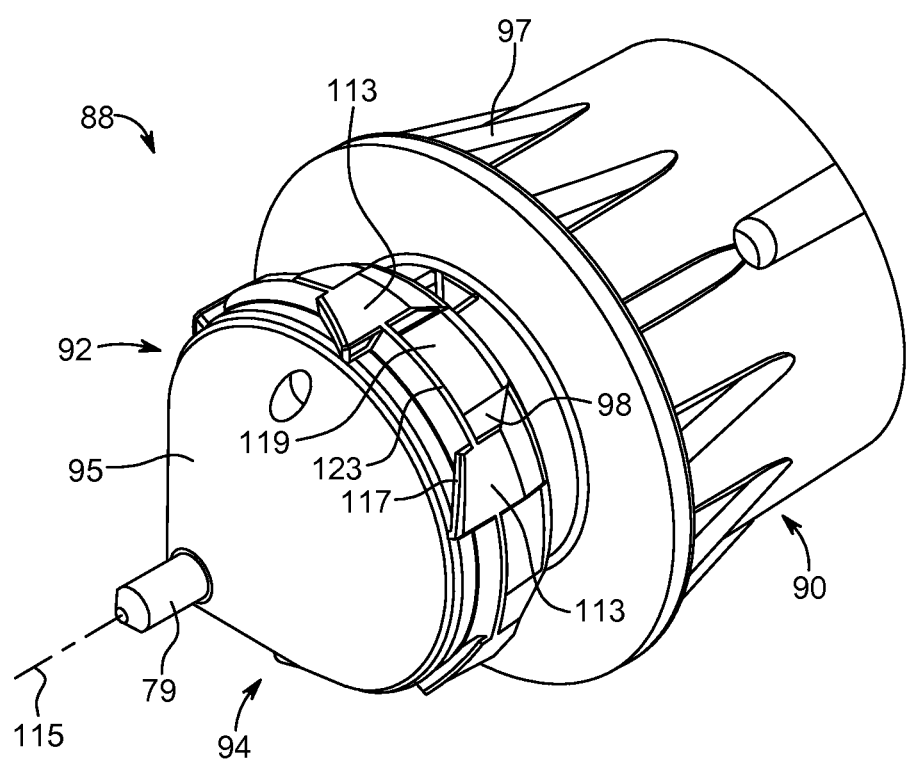
FIG. 20 is a front perspective view of a piston in accordance with another aspect.
Figure 20B:
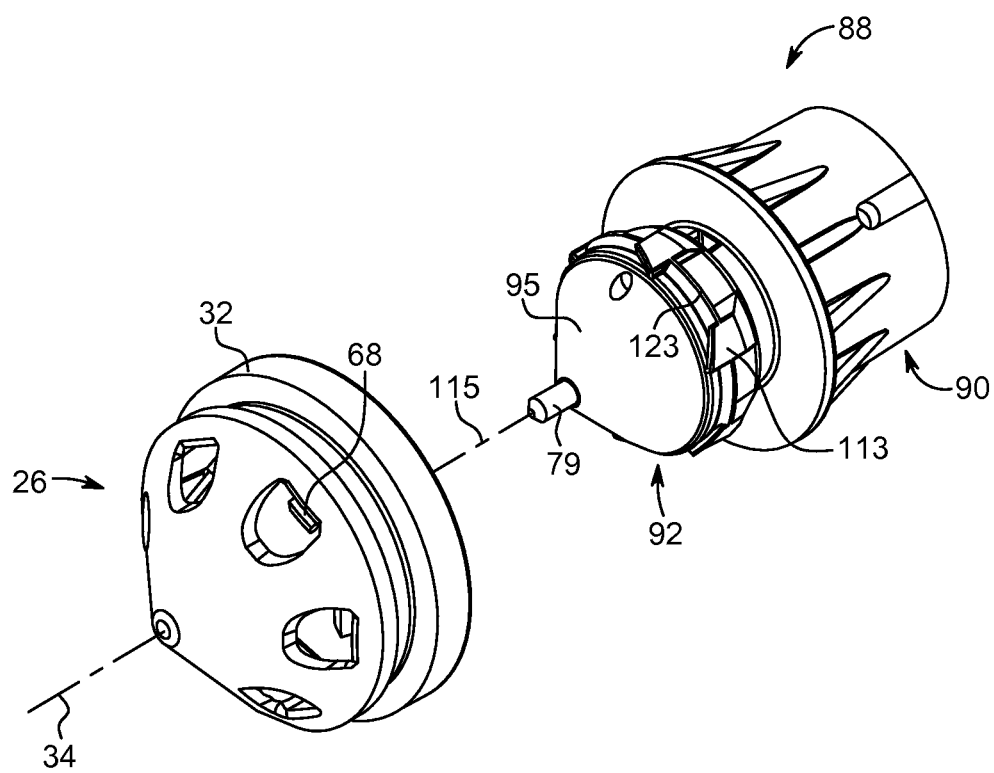
Figure 20C:
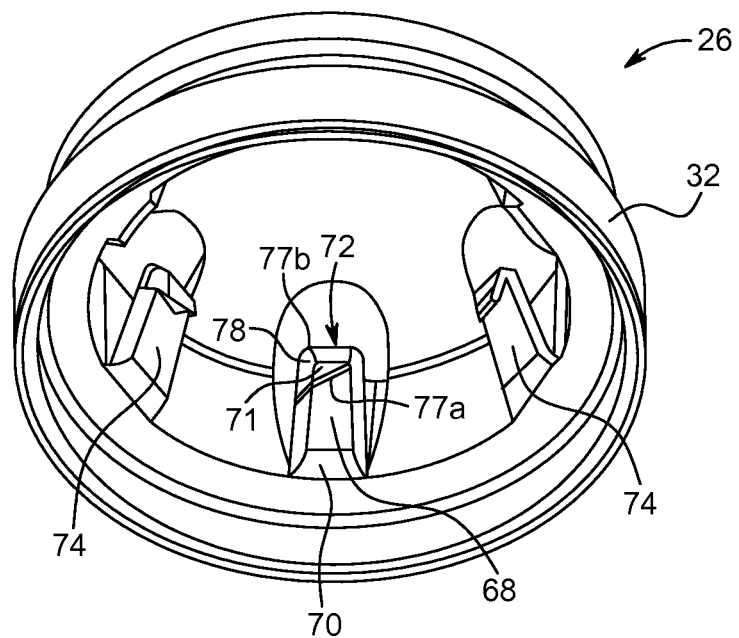
Figure 20D:
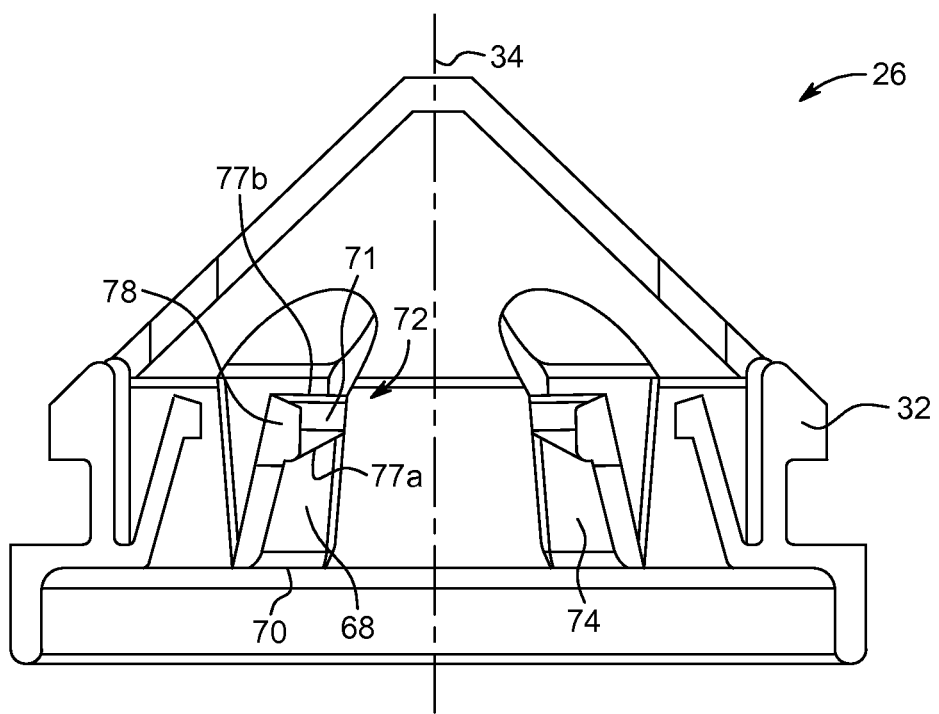

In some aspects, such as shown in FIG. 17, the width of the second alignment member 113 on the piston head 92 in a circumferential direction may be reduced. The plunger 26 may have one or more secondary alignment members 68a positioned adjacent to the one or more retaining members 68. In another aspect, such as shown in FIGS. 18-19, the one or more secondary alignment members 68a may be spaced apart from the one or more retaining members 68 such that each secondary alignment member 68a interacting with the one or more syringe alignment member 113 causes self-orientation such that at least one retaining member 68 is received recess 119 on the piston head 92. The one or more secondary alignment members 68a may have a first end 70a connected to the body 32 of the plunger and a second end 72a that protrudes in a proximal direction which is opposite to the protrusion direction of the second end 72 of the one or more retaining members 68. The second end 72a of the secondary retaining member 68a is deflectable in a radial direction relative to the first end 70a. The secondary retaining members 68a may further have an angled guide surface, for example defined by an outer surface of the second end 72a, that cooperates with the second alignment members 113 of the piston head 92 to align the plunger 26 relative to the piston 88. During the connection/disconnection process, the second end 72a of the secondary retaining members 68a is deflected radially outward as it passes over the region defined by the recesses 119 and is deflected back in a radially inward direction once the second end 72a clears the recesses 119. The one or more secondary retaining members 68a may have a latching member (not shown) to lock with at least a portion of the piston head 92, such as the radial lip 109.

Figure 21A:
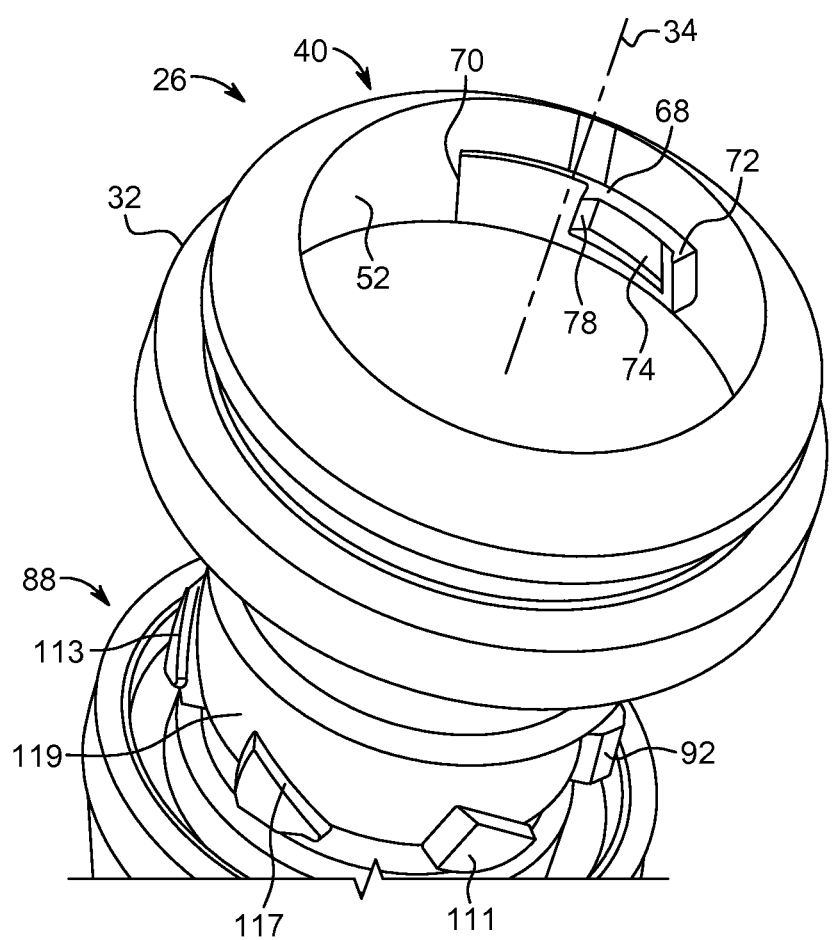
FIG. 21A is a front perspective view of a piston and a plunger in accordance with another aspect.
Figure 21B:
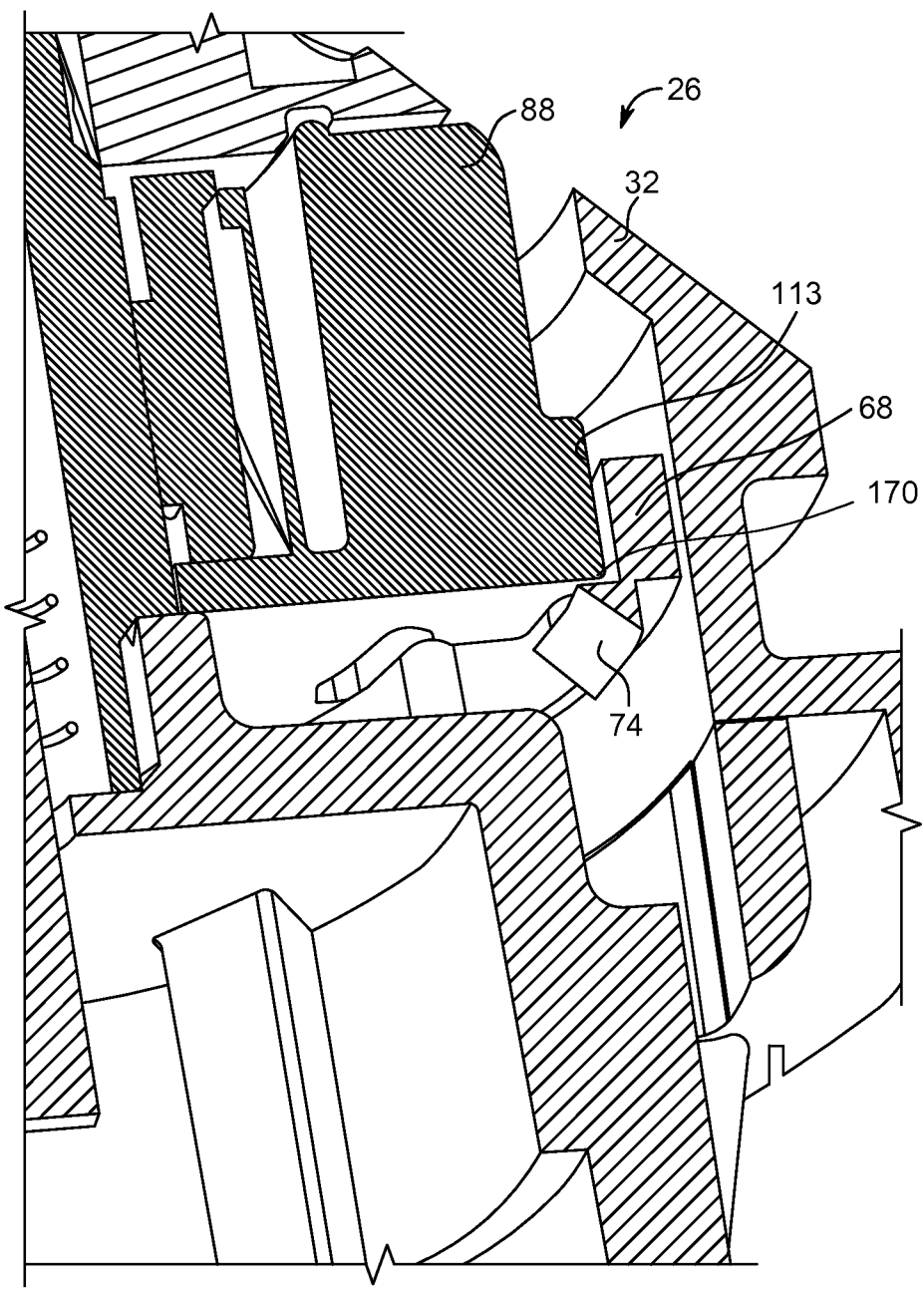
FIG. 21B is a cross-sectional side view of FIG. 21A showing the engagement between the piston and the plunger.
Figure 21C:
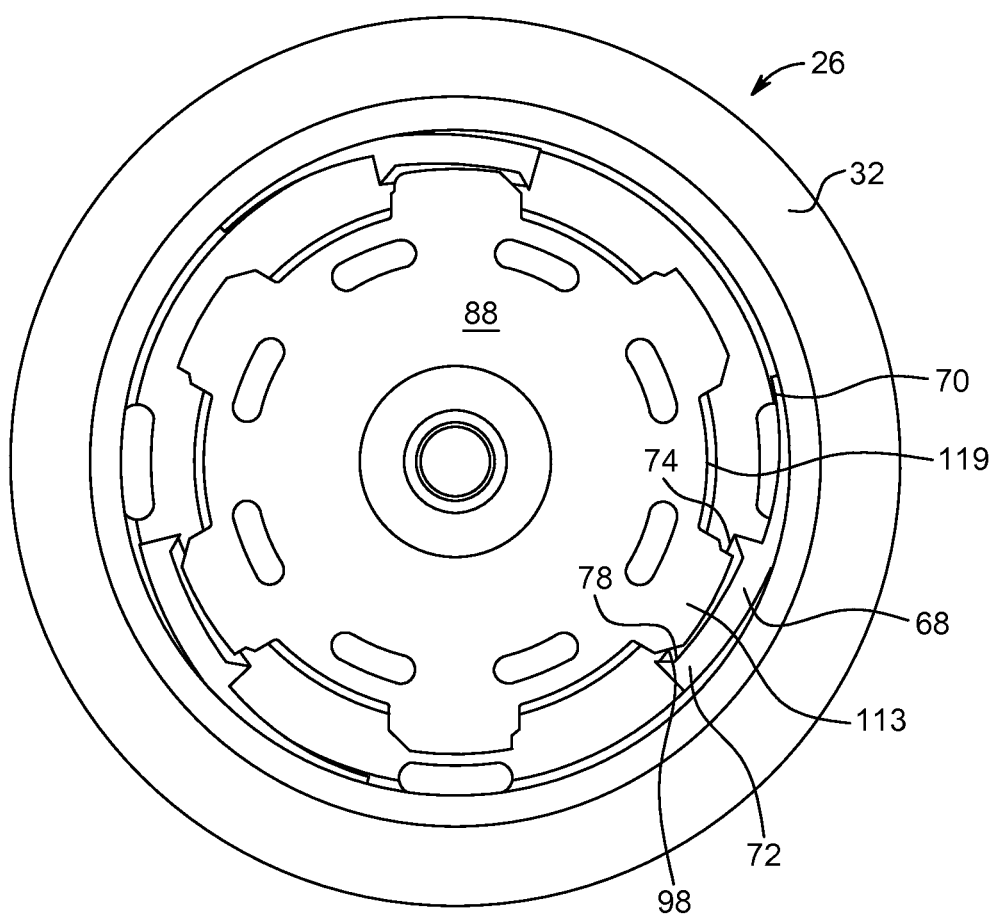
FIG. 21C is a cross-sectional top view of FIG. 21A showing the engagement between the piston and the plunger.

With reference to FIGS. 21A-21C, a plunger 26 and a piston 88 are shown in accordance with another aspect of the present disclosure. The components of the plunger 26 shown in FIGS. 21A-21C are substantially similar to the components of the plunger 26 described herein with reference to FIGS. 3A-4C. Similarly, the components of the piston 88 shown in FIGS. 21A-21C are substantially similar to the components of the piston 88 described herein with reference to FIGS. 3A-3C. Reference numerals in FIGS. 21A-21C are used to illustrate identical components of the corresponding reference numerals in FIGS. 4A-4C. As the previous discussion regarding the plunger 26 and piston 88 generally shown in FIGS. 3A-4C is applicable to the aspect of the present disclosure shown in FIGS. 21A-21C, only the relative differences between the plunger 26 and piston 88 generally shown in FIGS. 3A-4C and the plunger 26 and piston 88 generally shown in FIGS. 21A-21C are discussed hereinafter.

With reference to FIG. 21A, the plunger 26 may have at least one resiliently deflectable retaining member 68 (hereinafter "retaining member 68") protruding from the plunger body 32. In some aspects, the at least one retaining member 68 may protrude in a circumferential direction extending around an inner circumference of the inner surface 52 of the interior cavity 40. In some aspects, the at least one retaining member 68 may extend substantially perpendicularly to a longitudinal axis 34 of the plunger body 32. In other aspects, the at least one retaining member 68 may be angled in a distal or proximal direction relative a plane extending perpendicularly to the longitudinal axis 34 of the plunger body 32.

With continued reference to FIG. 21A, the at least one retaining member 68 has a first end 70 connected to the plunger body 32 and a second end 72 extending circumferentially around at least a portion an inner circumference of the plunger body 32 relative to the first end 70. The second end 72 may deflect or twist relative to the first end 70. As described herein, the second end 72 may be circumferentially deflectable toward or away from the inner surface of the plunger body 32 relative to the first end 70. The first end 70 and the second end 72 may be spaced apart in a direction that extends substantially circumferentially around an inner surface of the plunger body 32. The at least one retaining member 68 may be linearly, stepwise, or curvilinearly contiguous between the first end 70 and the second end 72. In some aspects, a plurality of retaining members 68 may spaced apart radially relative to the plunger longitudinal axis 34 along a circumference of the inner surface 52 of the interior cavity 40. The retaining members 68 may be separated from each other, such as by even or uneven spacing, by portions of the inner surface 52 of the interior cavity 40. The radial spacing of the at least one retaining member 68 relative to the plunger longitudinal axis 34 is selected to correspond to or operably interact with an outer shape of the piston, as described herein.

With reference to FIG. 21B, the second end 72 of the retaining member 68 has at least one catch 74 that is shaped to be engage at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 72 of the at least one retaining member 68 or it may be affixed or otherwise secured to the second end 72 of the at least one retaining member 68 using, for example, a frictional fit and/or an adhesive, welding, or by molding.

With reference to FIG. 21C, the plunger 26 may have at least one first cam member 78 that interacts with a piston of the fluid injector 10 (shown in FIG. 1) to radially deflect the at least one retaining member 68 upon rotation of the plunger 26 relative to the piston, as described herein. The at least one first cam member 78 may be provided at the second end 72 of the retaining member 68. The at least one first cam member 78 may be angled at an angle B relative to the body of the retaining member 68.

The plunger 26 may have at least alignment member, such as the first alignment member 71 shown in FIG. 3A protruding from the plunger body 32. As described herein, the at least one first alignment member 71 is shaped and/or configured for facilitating self-orienting alignment of the plunger 26 with the piston 88.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the one or more alignment members on the plunger 26 are not in rotational alignment to be received within the recesses 119 on the plunger head 92, the one or more alignment members on the plunger 26 contact the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 92 causes the retaining members 68 to deflect outward relative to the plunger longitudinal axis 34 from a first, undeflected position, to a second, radially deflected position. The piston 88 is advanced distally until the terminal portion of the second end 72 clears the retaining members 68, thereby allowing them to deflect radially inward toward or to their initial undeflected position. The catch 74 of at least one retaining member 68 is retained within the locking ledge 111 to prevent disengagement of the plunger 26 from the piston head 92.

To unlock the syringe 12 from the syringe port 16 and disengage the plunger 26 from the piston 88, the syringe 12 is rotated clockwise or counterclockwise about the syringe longitudinal axis, in a clockwise or counter-clockwise direction, relative to the syringe port 16. Rotation of the syringe 12, and thereby the plunger 26, about the plunger longitudinal axis 34 engages the first cam member 78 on the plunger 26 with the piston head 92. Such movement causes a deflection of the at least one retaining member 68 away from the piston head 92 to unlock the plunger 26 from the piston head 92 and allow the removal of the syringe 12.

With reference to FIGS. 22A-22D, a plunger 26 and a piston 88 are shown in accordance with another aspect of the present disclosure. The components of the plunger 26 shown in FIGS. 22A-22D are substantially similar to the components of the plunger 26 described herein with reference to FIGS. 3A-4C. Similarly, the components of the piston 88 shown in FIGS. 22A-22D are substantially similar to the components of the piston 88 described herein with reference to FIGS. 3A-3C. Reference numerals in FIGS. 22A-22D are used to illustrate identical components of the corresponding reference numerals in FIGS. 4A-4C. As the previous discussion regarding the plunger 26 and piston 88 generally shown in FIGS. 3A-4C is applicable to the aspect of the present disclosure shown in FIGS. 22A-22D, only the relative differences between the plunger 26 and piston 88 generally shown in FIGS. 3A-4C and the plunger 26 and piston 88 generally shown in FIGS. 22A-22D are discussed hereinafter.

Figure 22A:
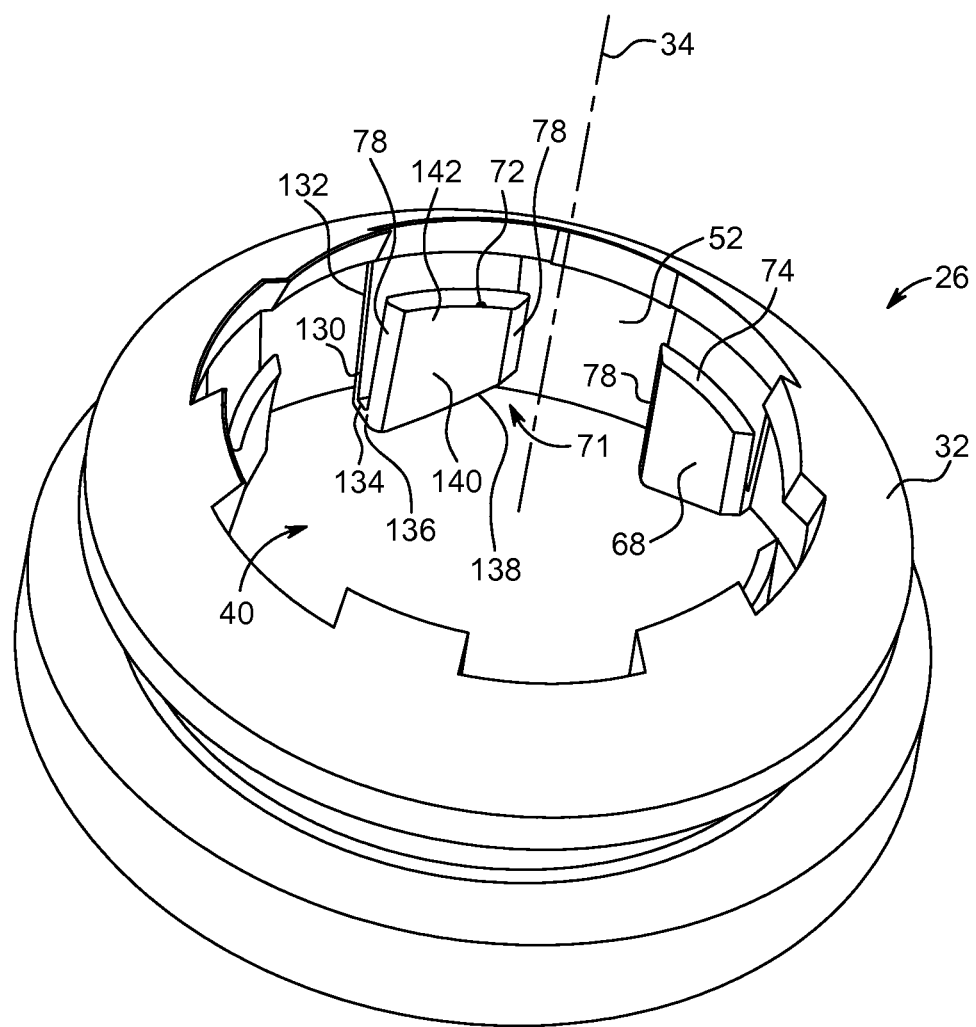
FIG. 22A is a front perspective view of a plunger in accordance with another aspect.
Figure 22B:
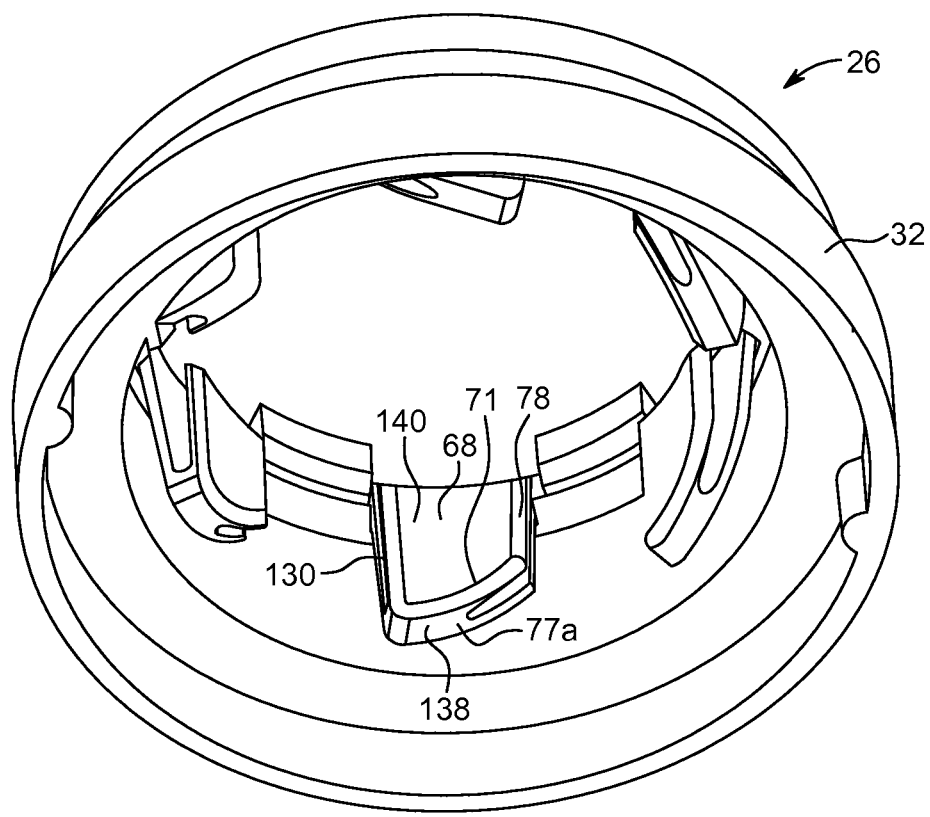
FIG. 22B is a bottom perspective view of the plunger shown in FIG. 22A.

With reference to FIG. 22A, the plunger 26 may have at least one resiliently deflectable retaining member 68 (hereinafter "retaining member 68") protruding from the plunger body 32. In some aspects, the at least one retaining member 68 may be U-shaped, with a first portion 130 having a first end 132 connected to the plunger body 32 and a second end 134 extending in a direction toward the proximal end of the plunger body 32. The at least one retaining member 68 may further have a transition portion 136 connected to the second end 134 of the first portion 130. A first end 138 of a second portion 140 may be connected to the transition portion 136 at an end opposite to the connection of the second end 134 of the first portion 130. The transition portion 136 extends in a radial direction relative to the longitudinal axis 34 of the plunger body 32 and connects the first portion 130 to the second portion 140. A second end 142 of the second portion 140 extends toward the distal end of the plunger body 32. The first portion 130, the second portion 140, or both may deflect or twist relative to the plunger body 32. For example, the second end 134 of the first portion 130 may be deflectable in a radial or circumferential direction relative to the first end 132 and the plunger body 132. Alternatively, or in addition, the second end 142 of the second portion 140 may be deflectable in a radial or circumferential direction relative to the first end 138, and therefore, relative to the first portion 130 and the plunger body 32. In some aspects, a plurality of retaining members 68 may be spaced apart radially relative to the plunger longitudinal axis 34 along a circumference of the inner surface 52 of the interior cavity 40. The retaining members 68 may be separated from each other, such as by even or uneven spacing, by portions of the inner surface 52 of the interior cavity 40. The radial spacing of the at least one retaining member 68 relative to the plunger longitudinal axis 34 is selected to correspond to or operably interact with an outer shape of the piston, as described herein.

With reference to FIG. 22A, the second end 142 of the second portion 140 of the retaining member 68 has at least one catch 74 that is shaped to be engage at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 142 of the second portion 140 of the at least one retaining member 68 or it may be affixed or otherwise secured to the second end 72 of the at least one retaining member 68 using, for example, a frictional fit and/or an adhesive, welding, or by molding.

Figure 22C:
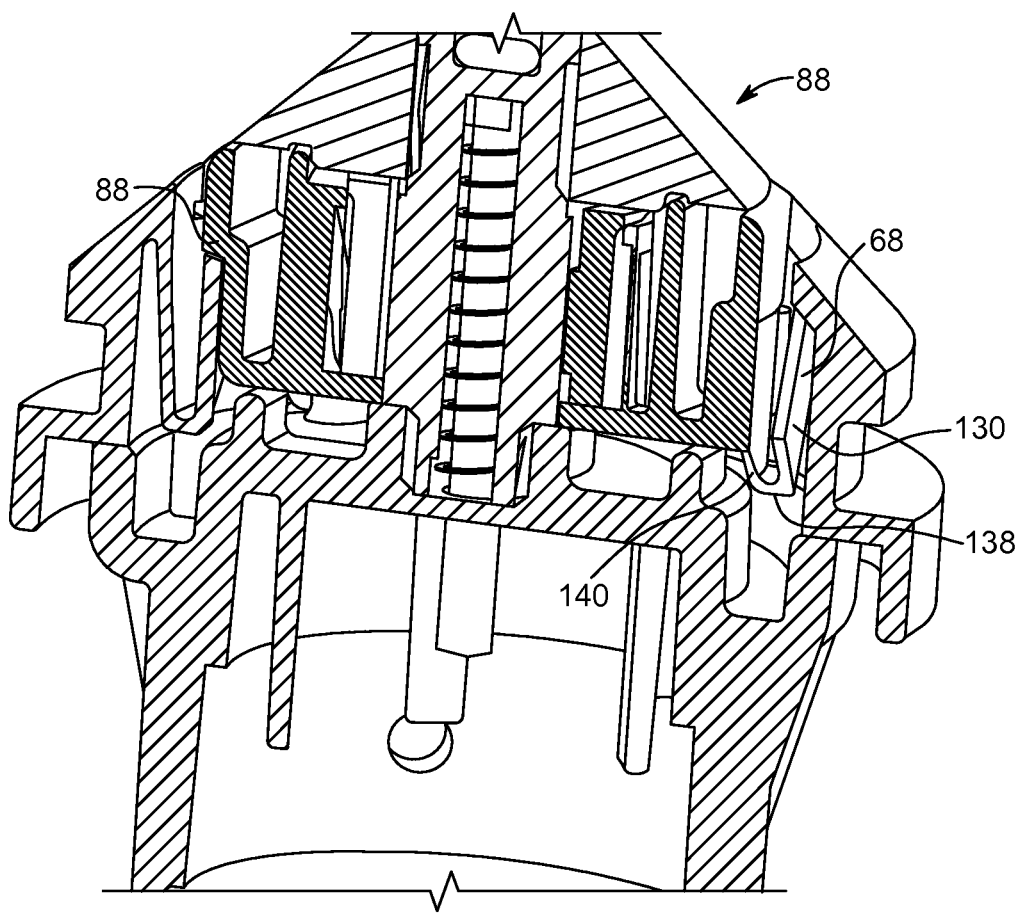
FIG. 22C is a cross-sectional side view of the plunger illustrated in FIG. 22A showing the engagement between a piston and the plunger.
Figure 22D:
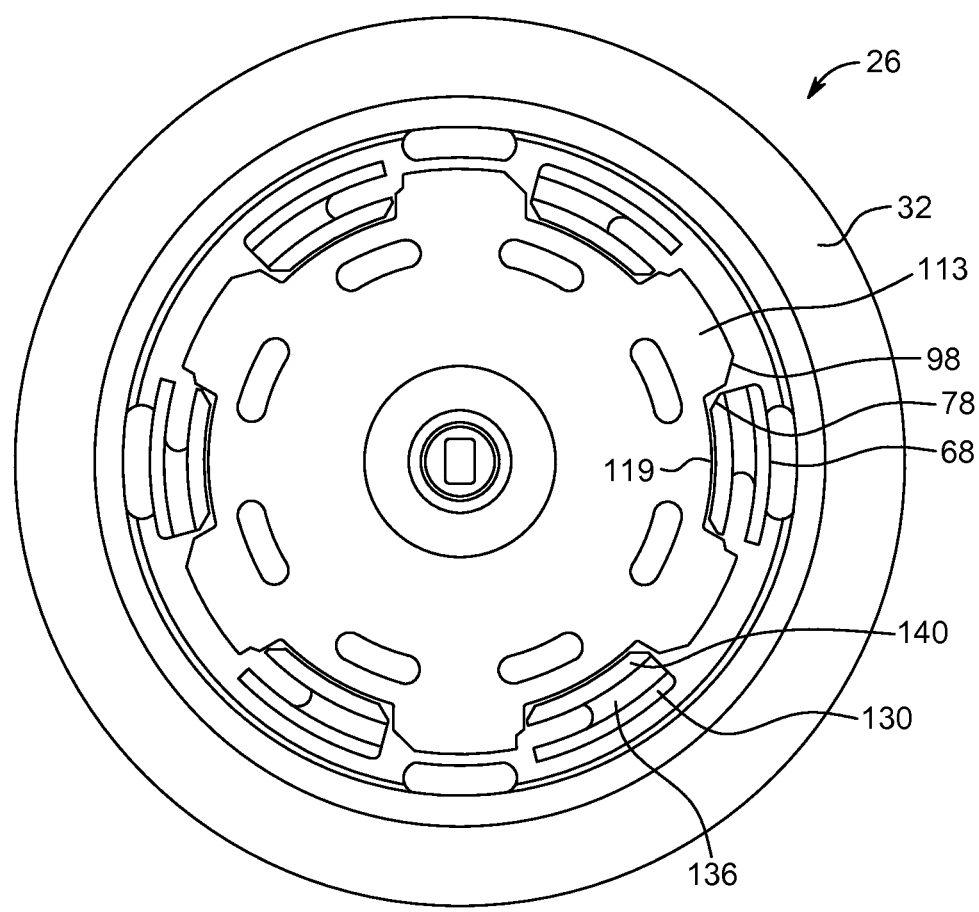
FIG. 22D is a cross-sectional top view of the plunger illustrated in FIG. 22A showing the engagement between a piston and the plunger.

With reference to FIG. 22C, the plunger 26 may have at least one first cam member 78 that interacts with a piston of the fluid injector 10 (shown in FIG. 1) to radially deflect the at least one retaining member 68 upon rotation of the plunger 26 relative to the piston, as described herein. The at least one first cam member 78 may be provided on the second portion 140 of the at least one retaining member 68. The at least one first cam member 78 may be angled at an angle B relative to the body of the retaining member 68.

With reference to FIG. 22A, the plunger 26 may have at least one first alignment member 71 defined on at least a portion of the at least one retaining member 68, such as the transition portion 136. The at least one first alignment member 71 is shaped and/or configured for facilitating self-orienting alignment of the plunger 26 with the piston 88. In some aspects, at least a portion of the at least one first alignment member 71 may extend in a direction that is angled relative to the direction of the plunger longitudinal axis 34. For example, at least one first alignment member 71 may have a proximal alignment surface 77a that is angled at an angle C relative to the longitudinal axis 34 to facilitate positioning of the retaining member 68 during connection of the plunger 26 to a piston. The proximal alignment surface 77a helps guide the plunger 26 into self-orienting alignment with the piston, as described herein.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the one or more alignment members on the plunger 26 are not in rotational alignment to be received within the recesses 119 on the plunger head 92, the one or more alignment members on the plunger 26 contact the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 92 causes the retaining members 68 to deflect outward relative to the plunger longitudinal axis 34 from a first, undeflected position, to a second, radially deflected position. The piston 88 is advanced distally until the terminal portion of the second end 72 clears the retaining members 68, thereby allowing them to deflect radially inward toward or to their initial undeflected position. The catch 74 of at least one retaining member 68 is retained within the locking ledge 111 to prevent disengagement of the plunger 26 from the piston head 92.

To unlock the syringe 12 from the syringe port 16 and disengage the plunger 26 from the piston 88, the syringe 12 is rotated clockwise or counterclockwise about the syringe longitudinal axis, in a clockwise or counter-clockwise direction, relative to the syringe port 16. Rotation of the syringe 12, and thereby the plunger 26, about the plunger longitudinal axis 34 engages the first cam member 78 on the plunger 26 with the piston head 92. Such movement causes a deflection of the at least one retaining member 68 away from the piston head 92 to unlock the plunger 26 from the piston head 92 and allow the removal of the syringe 12.

With reference to FIGS. 23A-23D, a plunger 26 and a piston 88 are shown in accordance with another aspect of the present disclosure. The components of the plunger 26 shown in FIGS. 23A-23D are substantially similar to the components of the plunger 26 described herein with reference to FIGS. 3A-4C. Similarly, the components of the piston 88 shown in FIGS. 23A-23D are substantially similar to the components of the piston 88 described herein with reference to FIGS. 23A-23D. Reference numerals in FIGS. 23A-23D are used to illustrate identical components of the corresponding reference numerals in FIGS. 4A-4C. As the previous discussion regarding the plunger 26 and piston 88 generally shown in FIGS. 3A-4C is applicable to the aspect of the present disclosure shown in FIGS. 23A-23D, only the relative differences between the plunger 26 and piston 88 generally shown in FIGS. 3A-4C and the plunger 26 and piston 88 generally shown in FIGS. 23A-23D are discussed herein.

Figure 23A:
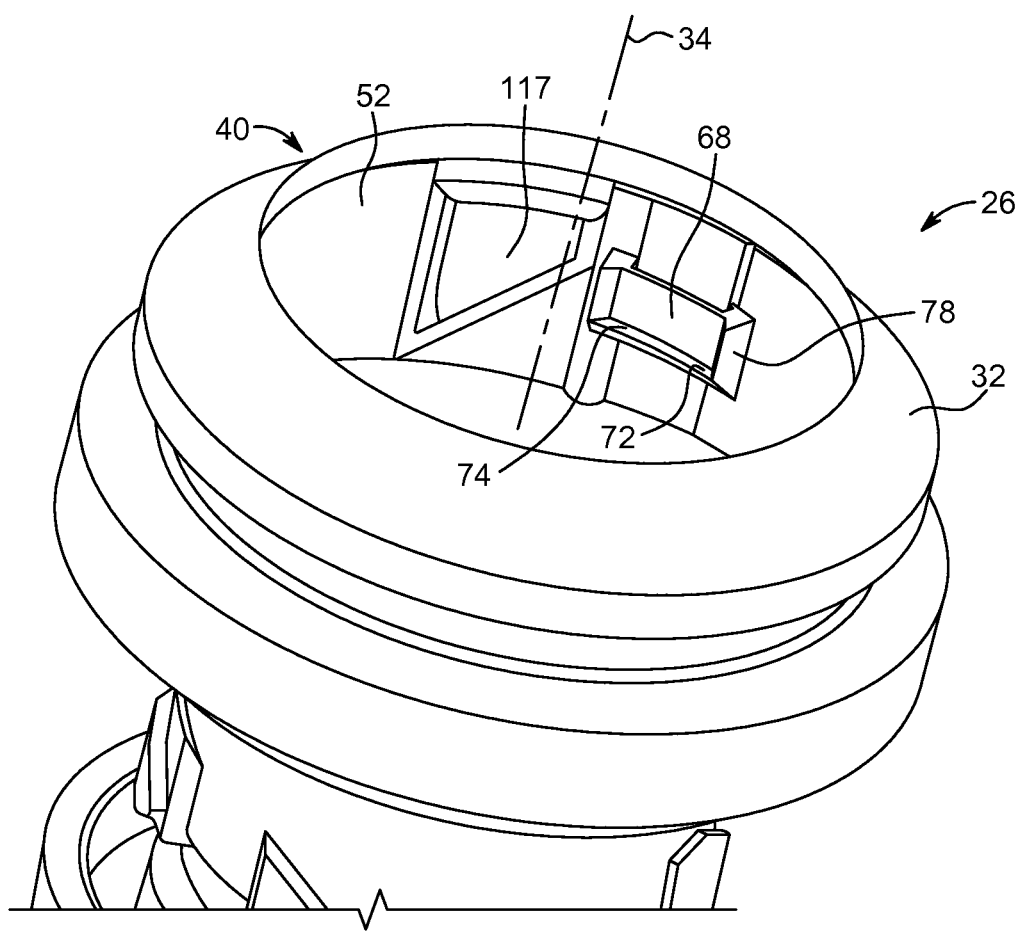
FIG. 23A is a front perspective view of a plunger in accordance with another aspect.

With reference to FIG. 23A, the plunger 26 may have at least one resiliently deflectable retaining member 68 (hereinafter "retaining member 68") protruding from the plunger body 32. In some aspects, the at least one retaining member 68 may protrude in a proximal direction toward the proximal end of the plunger body 32. In some aspects, the at least one retaining member 68 may extend substantially parallel to a longitudinal axis 34 of the plunger body 32. In other aspects, the at least one retaining member 68 may be angled relative to the longitudinal axis 34 of the plunger body 32.

With continued reference to FIG. 23A, the at least one retaining member 68 has a first end 70 connected to the plunger body 32 and a second end 72 extending in a proximal direction relative to the first end 70. The second end 72 may deflect or twist relative to the first end 70. As described herein, the second end 72 may be radially deflectable toward or away from the inner surface of the plunger body 32 relative to the first end 70. The at least one retaining member 68 may be linearly, stepwise, or curvilinearly contiguous between the first end 70 and the second end 72. In some aspects, a plurality of retaining members 68 may spaced apart radially relative to the plunger longitudinal axis 34 along a circumference of the inner surface 52 of the interior cavity 40. The retaining members 68 may be separated from each other, such as by even or uneven spacing, by portions of the inner surface 52 of the interior cavity 40. The radial spacing of the at least one retaining member 68 relative to the plunger longitudinal axis 34 is selected to correspond to or operably interact with an outer shape of the piston, as described herein.

Figure 23B:
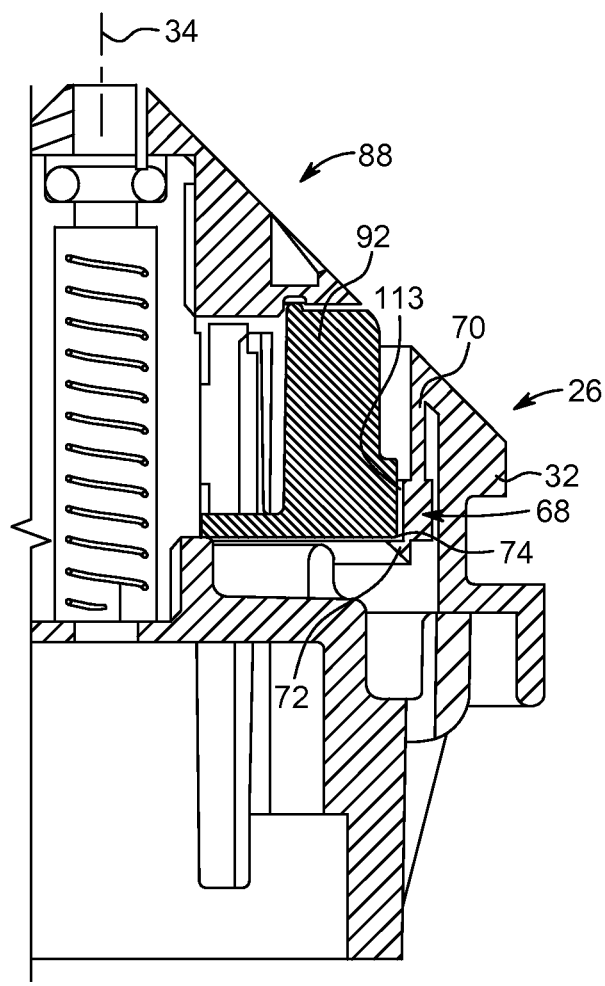
FIG. 23B is a first cross-sectional side view of the plunger illustrated in FIG. 23A showing the engagement between a piston and the plunger.

With reference to FIG. 23B, the second end 72 of the retaining member 68 has at least one catch 74 that is shaped to be engage at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 72 of the at least one retaining member 68 or it may be affixed or otherwise secured to the second end 72 of the at least one retaining member 68 using, for example, a frictional fit and/or an adhesive, welding, or by molding.

Figure 23C:
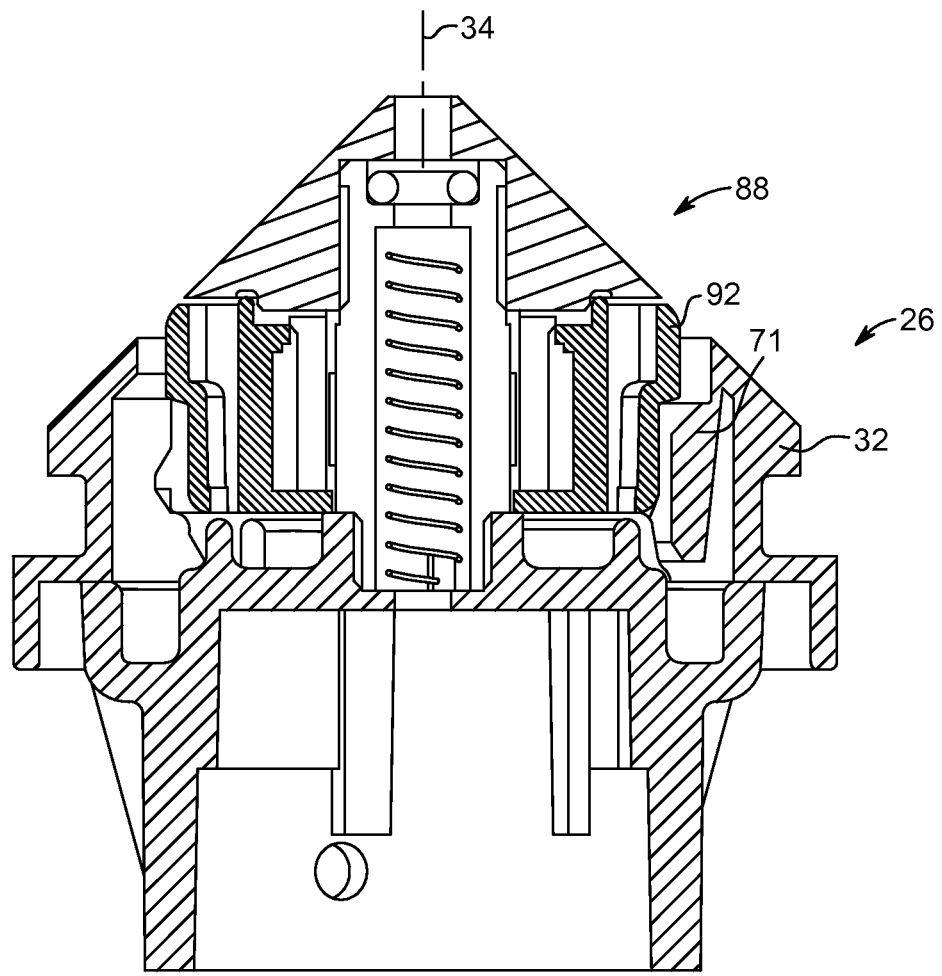
FIG. 23C is a second cross-sectional side view of the plunger illustrated in FIG. 23A showing the engagement between the piston and the plunger.
Figure 23D:
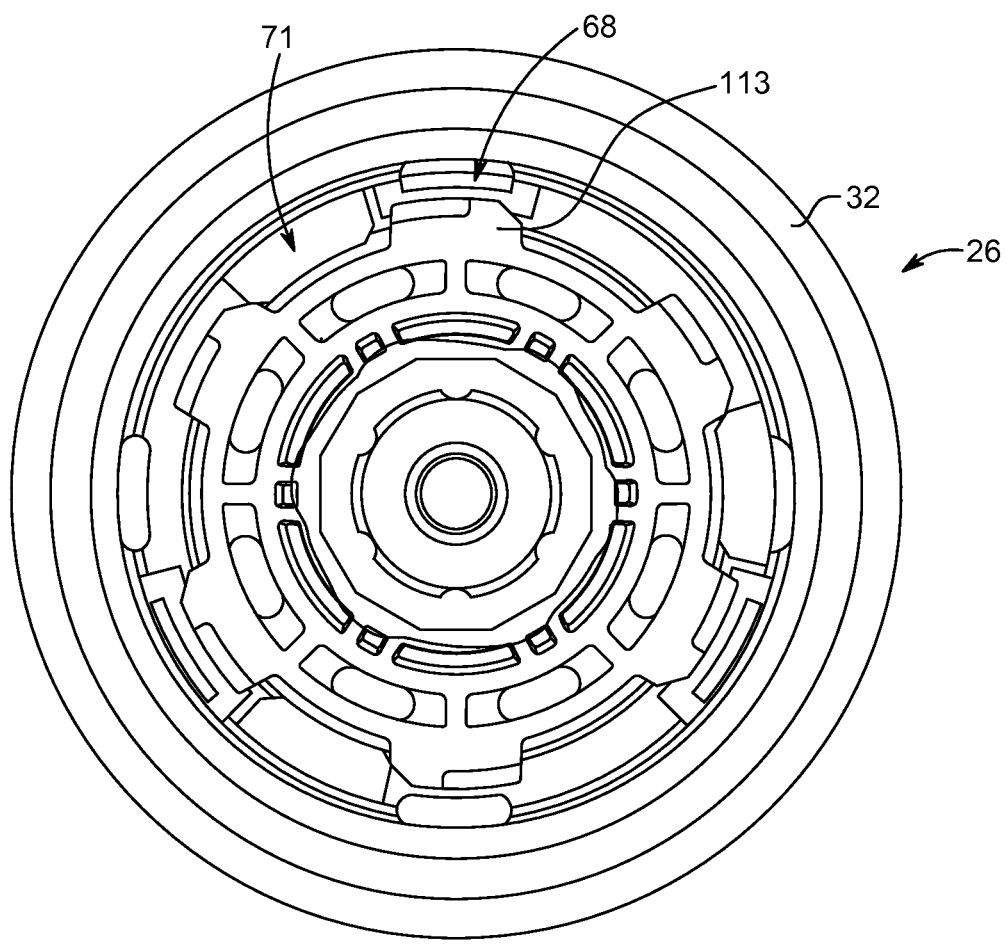
FIG. 23D is a cross-sectional top view of the plunger illustrated in FIG. 23A showing the engagement between a piston and the plunger.

With reference to FIG. 23C, the plunger 26 may have at least one first cam member 78 that interacts with a piston of the fluid injector 10 (shown in FIG. 1) to radially deflect the at least one retaining member 68 upon rotation of the plunger 26 relative to the piston, as described herein. The at least one first cam member 78 may be provided at the second end 72 of the retaining member 68. The at least one first cam member 78 may be angled at an angle B relative to the body of the retaining member 68.

The plunger 26 may have at least alignment member, such as the first alignment member 71 protruding from the plunger body 32. As described herein, the at least one first alignment member 71 is shaped and/or configured for facilitating self-orienting alignment of the plunger 26 with the piston 88. The at least one first alignment member 71 may be provided adjacent to the at least one retaining member 68.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the one or more alignment members 71 on the plunger 26 are not in rotational alignment to be received within the recesses 119 on the plunger head 92, the one or more alignment members 71 on the plunger 26 contact the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 92 causes the retaining members 68 to deflect outward relative to the plunger longitudinal axis 34 from a first, undeflected position, to a second, radially deflected position. The piston 88 is advanced distally until the terminal portion of the second end 72 clears the retaining members 68, thereby allowing them to deflect radially inward toward or to their initial undeflected position. The catch 74 of at least one retaining member 68 is retained within the locking ledge 111 to prevent disengagement of the plunger 26 from the piston head 92.

To unlock the syringe 12 from the syringe port 16 and disengage the plunger 26 from the piston 88, the syringe 12 is rotated clockwise or counterclockwise about the syringe longitudinal axis, in a clockwise or counter-clockwise direction, relative to the syringe port 16. Rotation of the syringe 12, and thereby the plunger 26, about the plunger longitudinal axis 34 engages the first cam member 78 on the plunger 26 with the piston head 92. Such movement causes a deflection of the at least one retaining member 68 away from the piston head 92 to unlock plunger 26 from the piston head 92 and allow the removal of syringe 12.

Figure 24A:
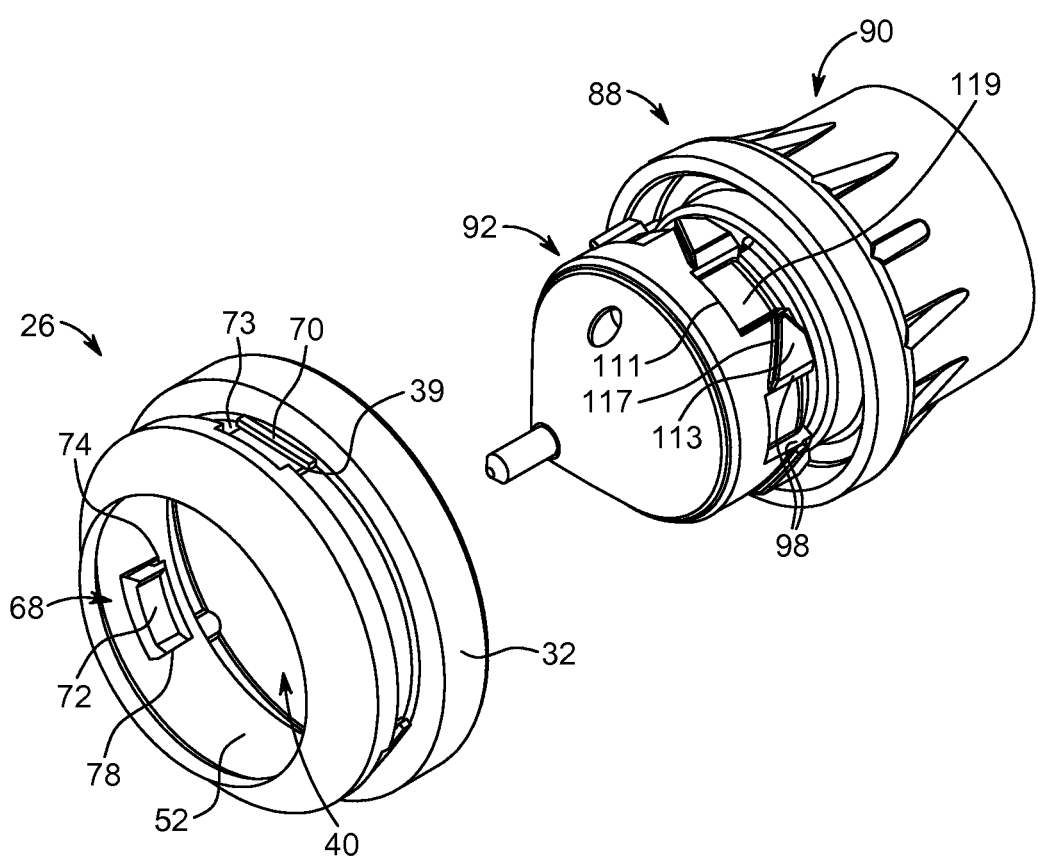
FIG. 24A is a partially-transparent side view of a piston and a plunger in accordance with another aspect.
Figure 24B:
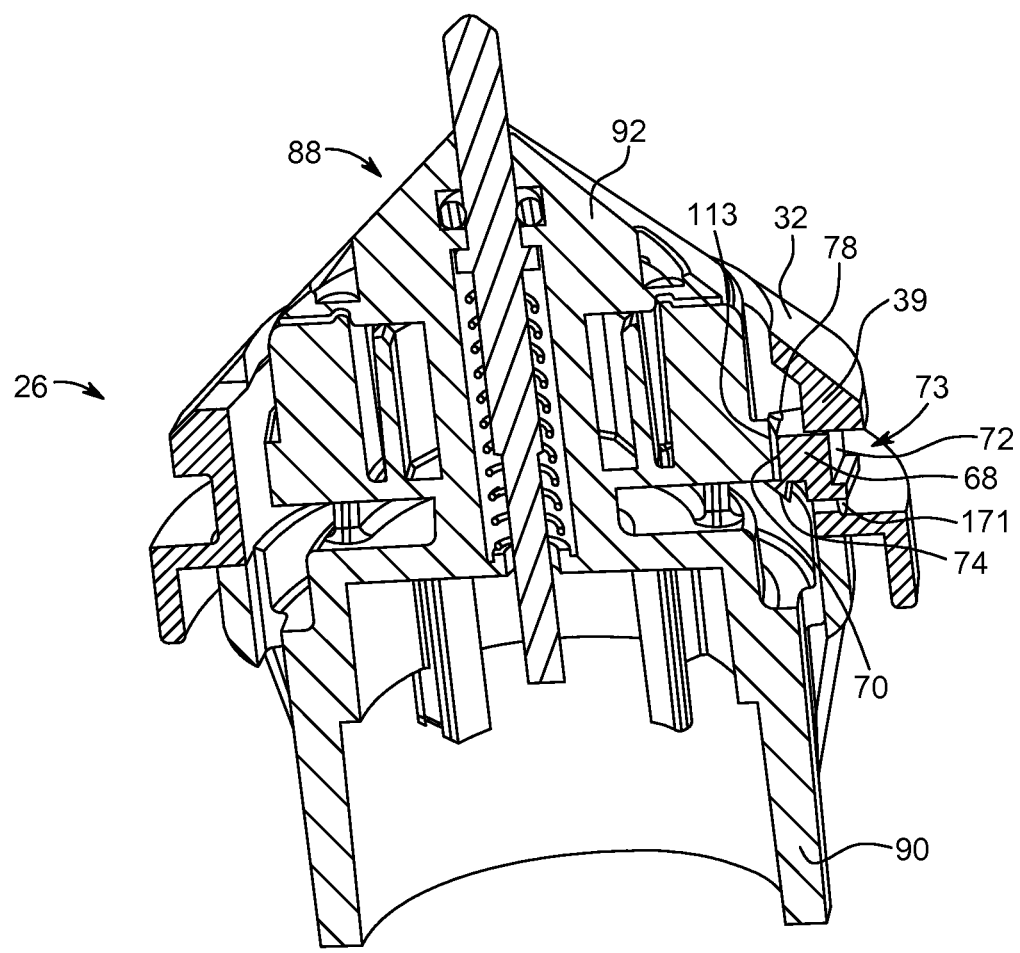
FIG. 24B is a partially-transparent side view of a piston and a plunger in accordance with another aspect.
Figure 24C:
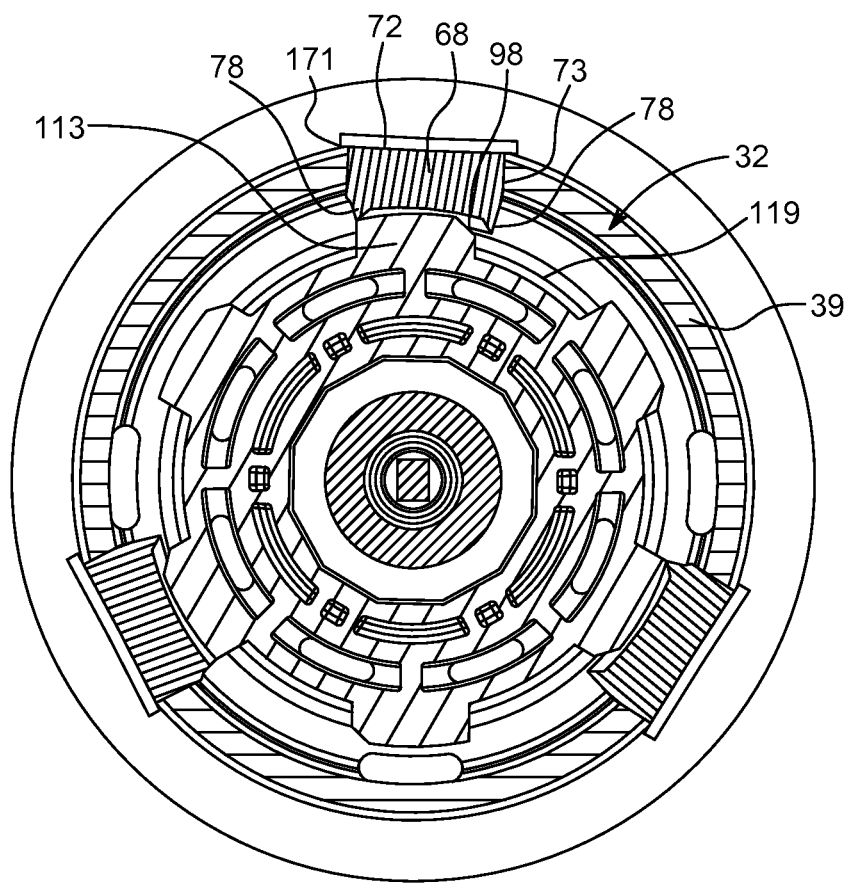
FIG. 24C is a partially-transparent side view of a piston and a plunger in accordance with another aspect.

With reference to FIGS. 24A-24C, a plunger 26 and a piston 88 are shown in accordance with additional aspects of the present disclosure. The components of the plunger 26 shown in FIGS. 24A-24C are substantially similar to the components of the plunger 26 described herein with reference to FIGS. 3A-4C. Similarly, the components of the piston 88 shown in FIGS. 24A-24C are substantially similar to the components of the piston 88 described herein with reference to FIGS. 24A-24C. Reference numerals in FIGS. 24A-24C are used to illustrate identical components of the corresponding reference numerals in FIGS. 4A-4C. As the previous discussion regarding the plunger 26 and piston 88 generally shown in FIGS. 3A-4C is applicable to the aspect of the present disclosure shown in FIGS. 24A-24C, only the relative differences between plunger 26 and piston 88 generally shown in FIGS. 3A-4C and plunger 26 and piston 88 generally shown in FIGS. 24A-24C are discussed herein.

With reference to FIG. 24A-24C, the plunger 26 may have at least retaining member 68a protruding radially outward from an outer surface of the plunger body 32. The at least one retaining member 68a is formed as a protrusion that is comprised of one or more distinct elements. In some aspects, the retaining member 68a is integrally formed with the plunger body 32 such that the retaining member 68a is fixed relative to the plunger body 32. In other aspects, at least a portion of the retaining member 68a may be movable or deflectable relative to another portion of the retaining member 68a and/or relative to the plunger body 32. The at least one retaining member 68a has a first end 70 connected to the plunger body 32 and a second end 72 extending in a proximal direction relative to the first end 70. The at least one retaining member 68a may be linearly, stepwise, or curvilinearly contiguous between the first end 70 and the second end 72. For example, the at least one retaining member 68a may have a first portion separated from a second portion by a segment of the plunger body 32 (FIG. 24A). In other aspects, the at least one retaining member 68a may be continuous between the first end 70 and the second end 72. At least a portion of the at least one retaining member 68a may be angled relative to the longitudinal axis 34 of the plunger body 32. The angled portion, such as alignment surface 71a, may interact with at least a portion of the piston 88 to assist in self-orienting alignment of the plunger 26 relative to the piston 88.

In some aspects, a plurality of retaining members 68a may be spaced apart radially relative to the plunger longitudinal axis 34 along a circumference of the inner surface 52 of the interior cavity 40. The retaining members 68a may be separated from each other, such as by even or uneven spacing, by portions of the inner surface 52 of the interior cavity 40. The radial spacing of the at least one retaining member 68a relative to the plunger longitudinal axis 34 is selected to correspond to or operably interact with an outer shape of the piston, as described herein.

The second end 72 of the retaining member 68a has at least one catch 74a that is shaped to be engage at least a portion of a recess, lip, or ledge on the piston 88 to lock the at least one retaining member 68a, along with the plunger 26, relative to the piston 88. In some aspects, the at least one catch 74a may be defined as a ledge or a step that is configured to engage at least a portion of a recess, lip, or ledge on the piston 88 to lock the at least one retaining member 68a, along with the plunger 26, relative to the piston 88. The at least one catch 74a may be formed integrally with the second end 72 of the at least one retaining member 68a or it may be affixed or otherwise secured to second end 72 of the at least one retaining member 68a using, for example, a frictional fit and/or an adhesive, welding, or molding.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the alignment surface 71a on the plunger 26 is not in rotational alignment to be received within the recesses 119 on the plunger head 92, the alignment surface 71a on the plunger 26 contacts the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 92 causes the retaining members 68a to move within a recess 119 defined between the adjacent second alignment members 113 on the piston 88. The piston 88 is advanced distally until the terminal portion of the second end 72 of the retaining members 68a clears the second alignment members 113, thereby allowing the retaining members 68a to slide underneath the second alignment members 113 of the plunger 88 until the catch 74a engages at least a portion of a recess, lip, or ledge on the piston 88 to lock the at least one retaining member 68a, along with the plunger 26, relative to piston 88.

To unlock the syringe 12 from the syringe port 16 and disengage the plunger 26 from the piston 88, the syringe 12 is rotated clockwise or counterclockwise about the syringe longitudinal axis, in a clockwise or counter-clockwise direction, relative to the syringe port 16. Rotation of the syringe 12, and thereby the plunger 26, about the plunger longitudinal axis 34 causes at least a portion of the retaining members 68a, such as the proximal end 70, to engage at least a portion of the second alignment members 113 on the piston 88. The engagement between the retaining members 68a with the second alignment members 113 causes the retaining members 68a to be urged in the distal direction due to the inclined shape of the second alignment members 113.

Figure 25:
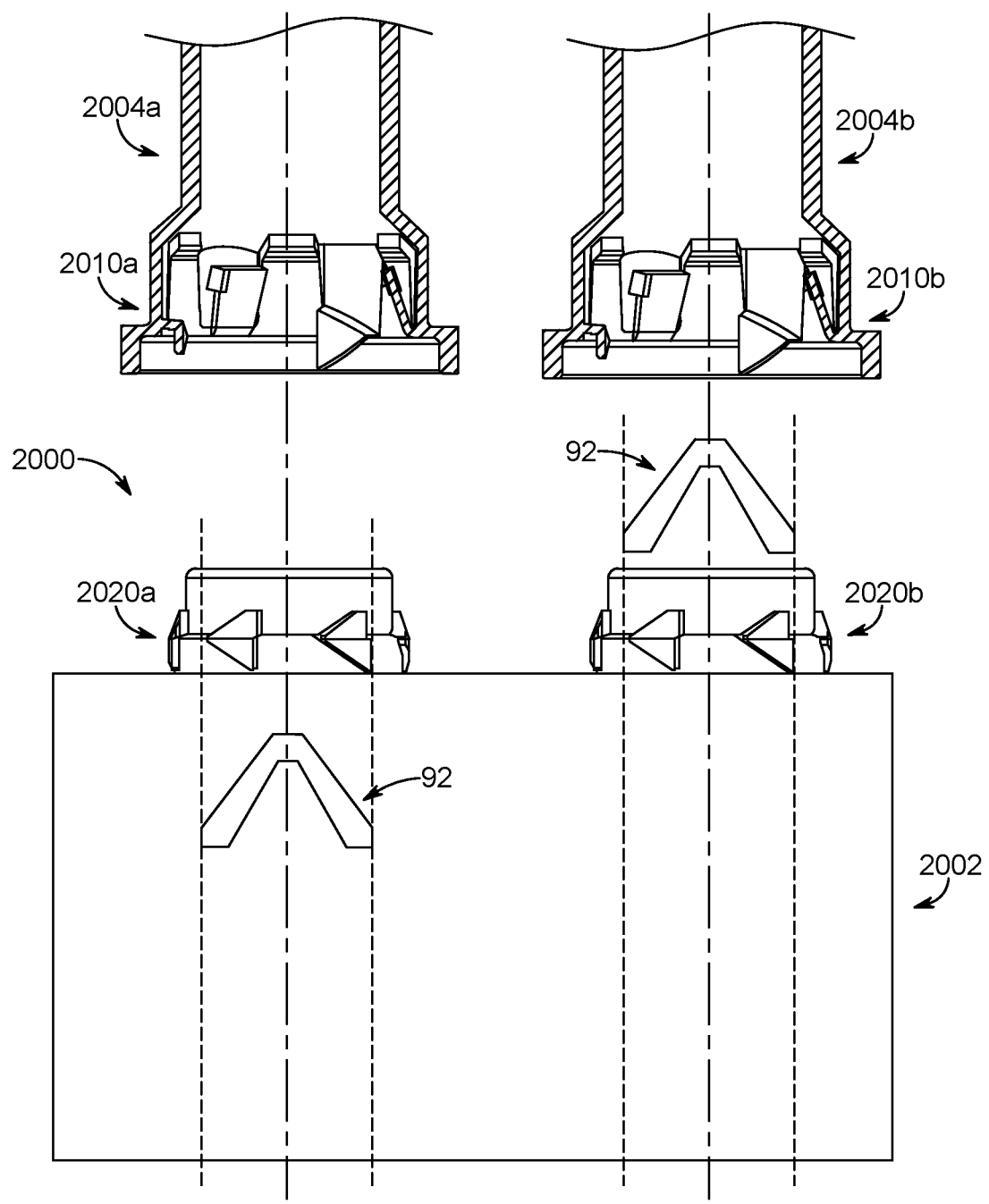
FIG. 25 is an exploded front view of a system including a fluid injector and a pair of pressure jackets in accordance with another aspect of the present disclosure.
Figure 26:
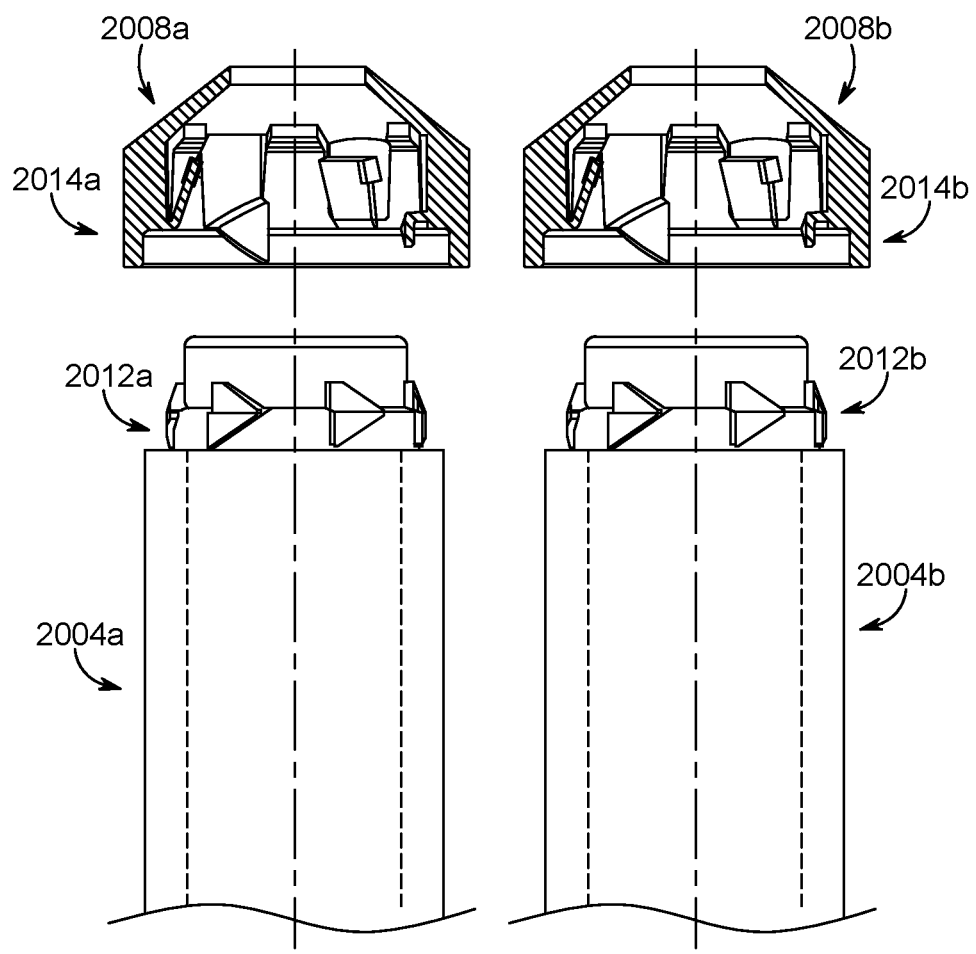
FIG. 26 is an exploded front view of a pair of pressure jackets in accordance with another aspect.
Figure 27:
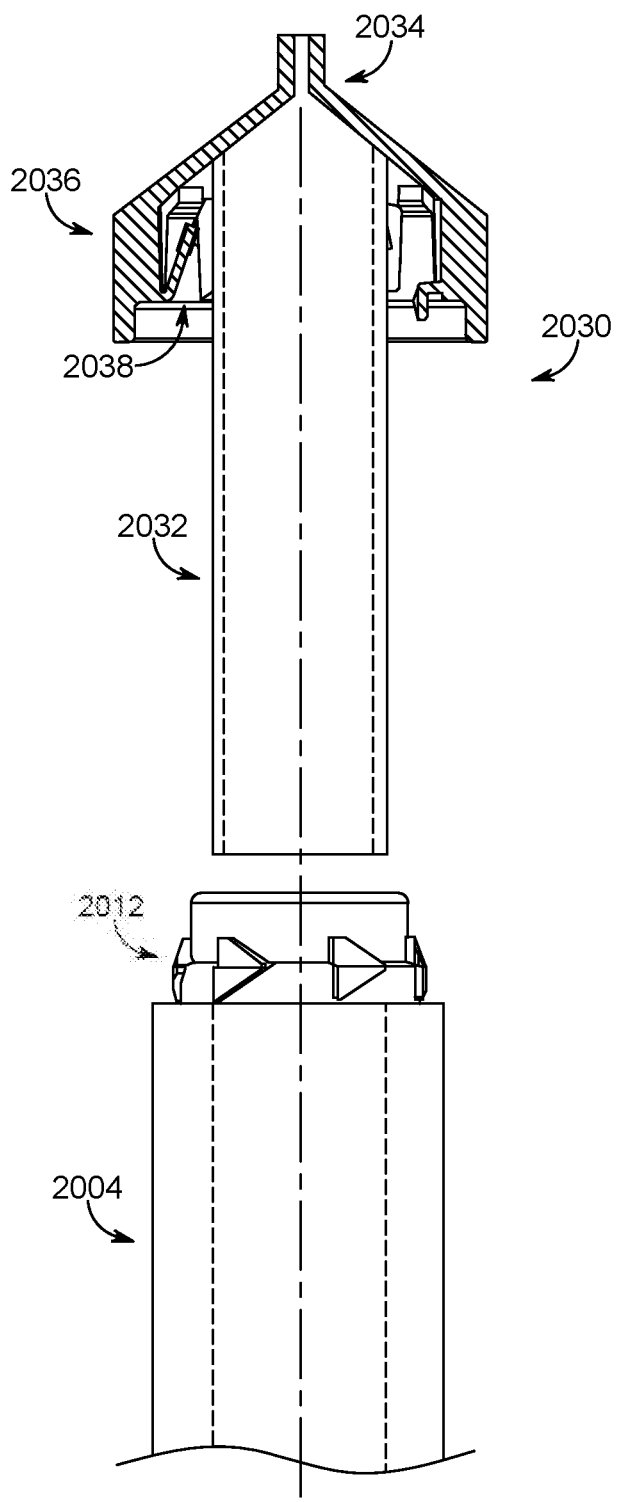
FIG. 27 is an exploded front view of a syringe assembly and a pressure jacket in accordance with another aspect.

Next, referring to FIGS. 25-27, an injector assembly 2000 in accordance with another aspect of the present disclosure is shown. Injector assembly 2000 comprises a housing 2002, which houses an automated or powered fluid injector. The fluid injector is adapted to interface with and actuate one or more syringes, wherein each syringe may be independently filled with a medical fluid such as contrast media, saline solution, or any desired medical fluid, as is similarly described above with respect to FIG. 1. For example, the injector housing 2002 is configured to accept and hold syringes 2006a, 2006b, each containing a medical fluid therein.

As is known in the art, syringes 2006a, 2006b are often made of polypropylene or a similar material having a certain minimum wall thickness. Syringes 2006a, 2006b are subject to pressures of up to 1200 psi when used to inject fluid into a patient, and thus wall thickness and resilience of the syringe are important in ensuring that the syringe does not burst or leak. To further combat possible radial expansion of syringes 2006a, 2006b when subject to high pressure injection, respective pressure jackets 2004a, 2004b may be utilized to enclose and retain syringes 2006a, 2006b. Pressure jackets 2004a, 2004b act to limit radial expansion of the syringe barrels. That is, during an injection procedure, exterior walls of syringes 2006a, 2006b expand against an interior wall of respective pressure jackets 2004a, 2004b, thereby limiting the radial expansion of the exterior walls of syringes that could otherwise lead to bursting or leakage.

Pressure jackets 2004a, 2004b may be separate elements or may be formed in a one-piece, monolithic design. Pressure jackets 2004a, 2004b are retained on an injector head of housing 2002 via respective attachment interfaces 2010a, 2010b.

In addition to radial forces acting on syringes 2006a, 2006b and pressure jackets 2004a, 2004b, significant axial movement during high pressure injection is also possible due to the elastic nature of the structural components restraining syringes 2006a, 2006b. For example, a single 150 ml syringe having a cross-sectional area of 1.6 in$^2$ at 1200 psi may require a force of 2400 psi to restrain forward motion of the syringe. To restrict this axial motion of syringes 2006a, 2006b, respective caps 2008a, 2008b may be used to partially encapsulate the distal end of syringes 2006a, 2006b and retain syringes 2006a, 2006b within the injector and within pressure jackets 2004a, 2004b during high-pressure injection. Caps 2008a, 2008b have an opening formed on a distal end thereof to allow at least a portion of a neck 2009a, 2009b of syringes 2006a, 2006b to protrude therethrough, thereby allowing syringes 2006a, 2006b to be connected to fluid lines leading to the patient.

Due to the axial forces imparted on syringes 2006a, 2006b, it is desirable for the attachment interfaces between the pressure jackets 2004a, 2004b and the housing 2002 and between the caps 2008a, 2008b and the pressure jackets 2004a, 2004b to be of sufficient strength to resist undo axial movement or inadvertent detachment. However, while strength is key, it is also important for an operator to be able to easily remove the caps 2008a, 2008b and/or pressure jackets 2004a, 2004b, as it is necessary to remove or insert syringes 2006a, 2006b. Accordingly, it is desirable for the connection interface between pressure jackets 2004a, 2004b and housing 2002 to be sufficiently secure, yet allow for easy attachment and removal. Similarly, it is desirable for a connection interface between caps 2008a, 2008b and pressure jackets 2004a, 2004b to also be secure, yet allow for easy attachment and removal.

In order to achieve these desired attributes, attachment interfaces 2020a, 2020b of the housing 2002 may have connector features similar to those of piston head 92 shown and described with respect to FIGS. 4A-4C, while attachment interfaces 2010a, 2010b of the pressure jackets 2004a, 2004b may have connector features similar to those of plunger 26 shown and described with respect to FIGS. 3A-3E. That is, attachment interfaces 2020a, 2020b of the housing 2002 may comprise one or more alignment members, similar to alignment members 113, disposed on a one-way rotation mechanism (similar to one-way rotation mechanism 99) that are positioned circumferentially about injector openings on the housing 2002. Each one-way rotation mechanism is preferably positioned about an injector opening of the housing 2002 so as to allow respective piston heads 92 to pass therethrough and into respective syringes 2006a, 2006b. Complementary to the connector features of the attachment interfaces 2020a, 2020b, attachment interfaces 2010a, 2010b of the pressure jackets 2004a, 2004b may comprise one or more retaining members, similar to retaining members 68 shown and described with respect FIGS. 3A-3E, as well as one or more alignment members, similar to alignment members 71, again shown and described with respect to FIGS. 3A-3E. Attachment interfaces 2010a, 2010b are configured to be circumferentially located about an opening on the proximal end of the pressure jackets 2004a, 2006b so as to allow respective syringes 2006a, 2006b to pass therethrough.

In operation, attachment interfaces 2010a, 2010b and attachment interfaces 2020a, 2020b are configured to interact in a manner substantially similar to the interaction between plunger 26 and piston head 92, as shown and described in detail with respect to FIGS. 5A-5D. That is, as attachment interfaces 2010a, 2010b are axially directed toward respective attachment interfaces 2020a, 2020b, alignment members (and corresponding alignment surfaces) on each of attachment interfaces 2010a, 2010b and attachment interfaces 2020a, 2020b interact, if necessary, to enable the pressure jackets 2004a, 2004b to be secured to the housing 2002. As described in detail above with respect to FIGS. 3A-5D, in the event that the alignment members of corresponding alignment interfaces contact one another during attachment, the alignment members disposed on the one-way rotation mechanism on attachment interfaces 2020a, 2020b are configured to ride along the corresponding alignment surfaces of the alignment members within attachment interfaces 2010a, 2010b until sufficient axial engagement has been achieved. One or more retaining members within attachment interfaces 2010a, 2010b, which preferably protrude inwardly from a proximal end of attachment interfaces 2010a, 2010b, are then configured to engage a radial lip or ledge within each of attachment interfaces 2020a, 2020b to securely attach the pressure jackets 2004a, 2004b to the housing 2002.

To detach pressure jackets 2004a, 2004b from housing 2002, pressure jackets 2004a, 2004b can be rotated (together or separately) relative to housing 2002 in a direction opposite the rotational direction of the one-way rotation mechanism. Rotation of pressure jackets 2004a, 2004b allows a cam surface on the alignment members of attachment interfaces 2020a, 2020b to interact with a cam surface on the at least one retaining member of attachment interfaces 2010a, 2010b, similar to that which is described above with respect to FIGS. 3A-5D. This interaction of cam surfaces acts to push the at least one retaining member radially outward such that the at least one retaining member no longer engages the radial lip or ledge within the attachment interfaces 2020a, 2020b, at which point the pressure jackets 2004a, 2004b can be axially detached from the housing 2002.

In accordance with an alternative aspect of the disclosure, the structural details of attachment interfaces 2010a, 2010b and 2020a, 2020b described above could be reversed. That is, attachment interfaces 2010a, 2010b of the housing 2002 could comprise, for example, the at least one retaining member and corresponding features, while the attachment interfaces 2010a, 2010b of the pressure jackets 2004a, 2004b could comprise the alignment members, one-way rotation mechanism, and radial lip or ledge.

Next, referring to FIG. 26, an alternative aspect of the disclosure is shown. As discussed above, it is preferable to have caps 2008a, 2008b disposed about a distal end of respective pressure jackets 2004a, 2004b so as to axially retain the respective syringes therein. Caps 2008a, 2008b preferably have respective attachment interfaces 2014a, 2014b for attachment to the pressure jackets 2004a, 2004b, as well as an opening formed therein to allow a portion of the syringe to extend therethrough.

To obtain a secure connection between pressure jackets 2004a, 2004b and caps 2008a, 2008b, it would be advantageous to configure the respective interfaces between pressure jackets 2004a, 2004b and caps 2008a, 2008b such that they interact in manner substantially similar to the interaction between piston head 92 and plunger 26, as shown and described in detail with respect to FIGS. 5A-5D. As shown in FIG. 26, pressure jackets 2004a, 2004b may have respective attachment interfaces 2012a, 2012b at distal ends thereof for engagement with respective caps 2008a, 2008b. Attachment interfaces 2014a, 2014b of the caps 2008a, 2008b may include one or more retaining members and one or more alignment members therein, as is shown and described with respect to FIGS. 3A-5D. Attachment interfaces 2012a, 2012b of the pressure jackets 2004a, 2004b may include one or more alignment members and a one-way rotation mechanism. The engagement between attachment interfaces 2012a, 2012b of the pressure jackets 2004a, 2004b and the attachment interfaces 2014a, 2014b of respective caps 2008a, 2008b may be identical or substantially similar to that described above with respect to FIGS. 3A-5D, and FIG. 25. In this manner, the caps 2008a, 2008b may be securely engageable with, and readily detachable from, the distal end of pressure jackets 2004a, 2004b.

As an alternative to a cap 2008 separate from and surrounding a portion of a syringe, FIG. 27 shows a syringe assembly 2030 having a syringe body 2032 with a cap 2036 integrated therewith. That is, the cap 2036 may be molded or formed directly with the syringe body 2032. A neck portion 2034 extends from a distal surface of the cap 2036 to provide a connection point for fluid lines leading to the patient. An attachment interface 2038, similar to attachment interfaces 2014a, 2014b shown and described with respect to FIG. 26, is formed in the cap 2036. As similarly described above with respect to FIG. 26, the attachment interface 2038 may include one or more retaining members and one or more alignment members therein which interact with the corresponding attachment interface 2012 of the pressure jackets 2004. Again, the engagement between attachment interface 2012 of the pressure jackets 2004 and the attachment interface 2038 of respective syringe assembly 2030 may be identical or substantially similar to that described above with respect to FIGS. 3A-5D, FIG. 25, and FIG. 26.

In accordance with an alternative aspect of the disclosure, the structural details of attachment interfaces 2012a, 2012b, and 2014a, 2014b described above could be reversed. That is, attachment interfaces 2012a, 2012b of pressure jackets 2004a, 2004b could comprise, for example, the at least one retaining member and corresponding features, while the attachment interfaces 2014a, 2014b of the caps 2008a, 2008b could comprise the alignment members, one-way rotation mechanism, and radial lip or ledge. Likewise, the structural details of the attachment interface 2012 and 2038 described above could be reversed, with attachment interfaces 2012 of the pressure jacket 2004 comprising, for example, the at least one retaining member and corresponding features, while the attachment interface 2038 of each syringe assembly 2030 could comprise the alignment members, one-way rotation mechanism, and radial lip or ledge.

While shown and described as being integrated with pressure jackets 2004a, 2004b, one or both of attachment interfaces 2010a, 2010b and 2012a, 2012b of pressure jackets 2004a, 2004b may alternatively be formed of a separate component attachable to the proximal or distal end of pressure jackets 2004a, 2004b. In this way, a conventional pressure jacket could be adapted with one or more separate attachment interfaces to enable the pressure jacket to securely interface with an appropriately-equipped housing, a cap similar to the cap 2008 discussed above, and/or a syringe assembly having an integrated cap, similar to syringe assembly 2030 discussed above.

Additionally, the respective engagements between attachment interfaces of housing 2002, pressure jackets 2004a, 2004b, caps 2008a, 2008b, and/or syringe assembly 2030 are not limited to the structural details shown and described with respect to FIGS. 3A-5D. Instead, the attachment interfaces could respectively utilize the structural details of the plunger/piston head engagement shown and described with respect to FIGS. 6A-12B, the details shown and described with respect to FIGS. 15A-15G, the details shown and described with respect to FIGS. 20-22D, the details shown and described with respect to FIGS. 23A-24C, or any combination thereof.

Although the disclosure has been described in detail for the purpose of illustration based on what are currently considered to be the most practical and preferred aspects, it is to be understood that such detail is solely for that purpose and that the disclosure is not limited to the disclosed aspects, but, on the contrary, is intended to cover modifications and equivalent arrangements. For example, it is to be understood that the present disclosure contemplates that, to the extent possible, one or more features of any aspect can be combined with one or more features of any other aspect.

We claim:

1. A pressure jacket for use with a fluid injector and syringe, the pressure jacket comprising:
    a pressure jacket body having a proximal end, a distal end, and a circumferential sidewall extending between the proximal end and the distal end along a longitudinal axis of a pressure jacket;
    at least one resiliently deflectable retaining member having a first segment attached to the pressure jacket body near the proximal end and a second segment protruding from the first segment toward the distal end of the pressure jacket body and deflectable radially outward relative to the first segment from an undeflected position to a radially deflected position; and
    at least one actuation member associated with the at least one resiliently deflectable retaining member,
    wherein the second segment is closer to the longitudinal axis of the pressure jacket in the undeflected position than in the radially deflected position, and
    wherein the at least one actuation member interacts with a housing of the fluid injector when the pressure jacket is connected to the housing to deflect the at least one resiliently deflectable retaining member radially outward to the radially deflected position upon rotation of the pressure jacket relative to the housing during disengagement of the pressure jacket from the housing of the fluid injector.

2. The pressure jacket according to claim 1, further comprising at least one alignment member associated with the proximal end of the pressure jacket body or the at least one resiliently deflectable retaining member, the at least one alignment member having an alignment surface for guiding the housing of the fluid injector into self-orienting alignment with the pressure jacket during engagement of the pressure jacket with the housing of the fluid injector.

3. The pressure jacket according to claim 2, wherein the at least one alignment member comprises a plurality of alignment members spaced apart around a circumference of the circumferential sidewall of the proximal end of the pressure jacket body.

4. The pressure jacket according to claim 3, wherein the plurality of alignment members are spaced apart at equal radial intervals around the circumference of the circumferential sidewall of the proximal end of the pressure jacket body.

5. The pressure jacket according to claim 1, wherein the second segment of the at least one resiliently deflectable retaining member is deflectable radially relative to the first segment away from the pressure jacket longitudinal axis.

6. The pressure jacket according to claim 1, wherein the at least one resiliently deflectable retaining member is linearly or curvilinearly contiguous between the first segment and the second segment.

7. The pressure jacket according to claim 1, wherein the second segment of the at least one resiliently deflectable retaining member is angled toward the longitudinal axis of the pressure jacket.

8. The pressure jacket according to claim 1, wherein the at least one actuation member is provided on a surface of the at least one resiliently deflectable retaining member.

9. The pressure jacket according to claim 8, wherein the at least one actuation member is at the second segment of the at least one resiliently deflectable retaining member.

10. The pressure jacket according to claim 1, wherein the at least one actuation member is angled relative to a plane defined by a body of the at least one resiliently deflectable retaining member.

* * * * *

UNITED STATES PATENT AND TRADEMARK OFFICE
CERTIFICATE OF CORRECTION

PATENT NO. : 11,291,766 B2
APPLICATION NO. : 15/769550
DATED : April 5, 2022
INVENTOR(S) : Swantner et al.

It is certified that error appears in the above-identified patent and that said Letters Patent is hereby corrected as shown below:

In the Specification
In Column 29, Line 12, delete "second cam member 121" and insert -- second cam member 98 --, therefor.
In Column 29, Line 26, delete "second cam member 121" and insert -- second cam member 98 --, therefor.
In Column 32, Line 8, delete "piston 92" and insert -- piston 88 --, therefor.
In Column 33, Line 67, delete "piston 92" and insert -- piston 88 --, therefor.
In Column 35, Line 46, delete "piston 92" and insert -- piston 88 --, therefor.
In Column 37, Line 15, delete "piston 92" and insert -- piston 88 --, therefor.
In Column 37, Line 23, delete "plunger 88" and insert -- plunger 26 --, therefor.
In Column 38, Line 66, delete "pressure jackets 2004a, 2006b" and insert -- pressure jackets 2004a, 2004b --, therefor.

Signed and Sealed this
Twenty-sixth Day of July, 2022

Katherine Kelly Vidal
*Director of the United States Patent and Trademark Office*